United States Patent
Fourrier et al.

(10) Patent No.: US 11,703,512 B2
(45) Date of Patent: Jul. 18, 2023

(54) METHOD FOR STABILIZING HEMOGLOBIN AND REAGENTS FOR PERFORMING THE SAME

(71) Applicant: Exact Sciences Corporation, Madison, WI (US)

(72) Inventors: Keith D. Fourrier, Madison, WI (US); Jacquelyn T. Hennek, Stoughton, WI (US); Michael J. Domanico, Middleton, WI (US); William G. Weisburg, San Diego, CA (US); Graham P. Lidgard, Middleton, WI (US); Kathleen S. Harings, Fitchburg, WI (US); Daniel J. Simpson, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 0 days.

(21) Appl. No.: 17/833,261

(22) Filed: Jun. 6, 2022

(65) Prior Publication Data

US 2022/0373564 A1 Nov. 24, 2022

Related U.S. Application Data

(63) Continuation of application No. 16/355,498, filed on Mar. 15, 2019, now Pat. No. 11,385,243.

(60) Provisional application No. 62/685,248, filed on Jun. 14, 2018, provisional application No. 62/648,874, filed on Mar. 27, 2018.

(51) Int. Cl.
*G01N 33/72* (2006.01)
*G01N 33/50* (2006.01)
*G01N 33/574* (2006.01)
*G01N 1/38* (2006.01)

(52) U.S. Cl.
CPC ............ *G01N 33/721* (2013.01); *G01N 1/38* (2013.01); *G01N 33/5094* (2013.01); *G01N 33/57419* (2013.01); *G01N 2333/805* (2013.01); *G01N 2800/50* (2013.01); *G01N 2800/52* (2013.01)

(58) Field of Classification Search
CPC .... G01N 33/721; G01N 1/38; G01N 33/5094; G01N 33/57419; G01N 2333/805; G01N 2800/50; G01N 2800/52
See application file for complete search history.

(56) References Cited

U.S. PATENT DOCUMENTS

| | | | |
|---|---|---|---|
| 3,252,762 A | 5/1966 | Adams et al. |
| 4,587,222 A | 5/1986 | Guffroy |
| 4,827,945 A | 5/1989 | Groman et al. |
| 4,971,914 A | 11/1990 | Lawrence |
| 9,211,112 B2 | 12/2015 | Lidgard et al. |
| 9,750,482 B2 | 9/2017 | Lidgard et al. |
| 2013/0004975 A1 | 1/2013 | Sugo |
| 2013/0157373 A1 | 6/2013 | Selinfreund et al. |
| 2013/0211286 A1 | 8/2013 | Lidgard et al. |
| 2016/0011225 A1 | 1/2016 | Holmes |
| 2016/0271164 A1 | 9/2016 | Zager et al. |
| 2019/0011462 A1 | 1/2019 | Shimada et al. |

FOREIGN PATENT DOCUMENTS

| | | |
|---|---|---|
| GB | 2069694 | 8/1981 |
| JP | H05281227 | 10/1993 |
| JP | H09224942 | 9/1997 |
| WO | WO 2010028382 | 3/2010 |
| WO | WO 2017104132 | 6/2017 |

OTHER PUBLICATIONS

Carozzi et al., (2013) "Fecal Collection and Stabilization Methods for Improved Fecal DNA Test for Colorectal Cancer in a Screening Setting", Journal of Cancer Research, 2013(818675): 1-8.
Gies et al., (2018) "Direct comparison of ten quantitative fecal immunochemical tests for hemoglobin stability in colorectal cancer screening", Clinical and Translational Gastroenterology, 9:168.

*Primary Examiner* — Jennifer Wecker
*Assistant Examiner* — Michael Paul Shimek
(74) *Attorney, Agent, or Firm* — Bozicevic, Field & Francis LLP; Shweta Chandra

(57) ABSTRACT

A stool resuspension solution comprising a hemoglobin stabilization reagent is provided. In some embodiments, the hemoglobin stabilization reagent may be an osmolyte, a polyvalent cation, a sugar or polysaccharide and, optionally, a polyvalent cation, a protoporphyrin, or an HRP stabilization component and, optionally, a polyvalent cation. A method of stabilizing hemoglobin in a stool sample in the solution is also provided, as well as a sample collection device containing the solution.

20 Claims, No Drawings

METHOD FOR STABILIZING HEMOGLOBIN AND REAGENTS FOR PERFORMING THE SAME

CROSS-REFERENCING

This application claims the benefit of U.S. provisional application Ser. No. 62/648,874, filed on Mar. 27, 2018, and 62/685,248, filed on Jun. 14, 2018, which applications are incorporated by reference herein.

BACKGROUND

Tests that detect hemoglobin (Hb) in a stool specimen are commonly used for colorectal cancer screening. The common procedures utilize a sample collection device that contains buffer to stabilize hemoglobin from the time of collection until the detection assay is conducted at the lab. The ability of the buffer to properly stabilize hemoglobin is critical for accurate test results and must stabilize hemoglobin during shipment over a range of environmental conditions. Increasing the ability of the buffer to stabilize hemoglobin would, for example, allow longer shipping durations and provide more flexibility to the patient and test lab for sample processing.

SUMMARY

Provided herein, among other things, is a stool resuspension solution that comprises a hemoglobin stabilization reagent. In some embodiments, the hemoglobin stabilization reagent in the solution may be an osmolyte, a polyvalent cation, a sugar or polysaccharide and, optionally, a polyvalent cation, a protoporphyrin, or an HRP stabilization component and, optionally, a polyvalent cation.

The solution finds use in methods that may benefit from stabilizing hemoglobin. In some embodiments, this method may comprise combining the stool sample with the stool resuspension solution to produce a suspension, and maintaining the suspension for a period of time. In some embodiments, this method may comprise shipping the suspension to a remote location. The hemoglobin stabilization reagent in the solution stabilizes the hemoglobin, thereby allowing the hemoglobin in the sample to be more accurately measured after several days in transit.

Compositions, methods and devices that employ the stool resuspension solution are provided.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

A stool resuspension solution comprising one or more hemoglobin stabilization reagents is provided. In some embodiments, the one or more hemoglobin stabilization reagents may be selected from, e.g., an osmolyte, a polyvalent cation, a sugar or polysaccharide and, optionally, a polyvalent cation, a protoporphyrin and an HRP stabilization component and, optionally, a polyvalent cation. Examples and concentrations of such reagents in the solution are set forth in the tables shown below and in the appendices.

In some embodiments, the solution may comprise an osmolyte, e.g., betaine. In these embodiments, the osmolyte (e.g., betaine) may be at a concentration in the range of 2 M to 5 M.

In some embodiments, the solution may comprise a sugar, e.g., sucrose or trehalose. In these embodiments, the sugar (e.g., sucrose or trehalose) may be at a concentration in the range of 0.1 M to 0.5 M. In either case, the solution may optionally contain a polyvalent cation, $Mg^{2+}$ or $Ca^{2+}$ In these embodiments, the polyvalent cation (e.g., calcium or magnesium ions) may be at a concentration in the range of 5 mM to 25 mM.

In some embodiments, the solution may comprise a polysaccharide, e.g., a substituted or unsubstituted polygalacturonic acid such as α-(1-4)-linked D-galacturonic acid. In these embodiments, the polysaccharide (e.g., the substituted or unsubstituted polygalacturonic acid) may be at a concentration in the range of 0.005% to 0.5% (e.g., 0.01% to 0.125%). In these embodiments, the solution may optionally contain a polyvalent cation. In embodiments in which the solution contains a polyvalent cation, the polyvalent cation may be at a concentration in the range of 5 mM to 25 mM. In some embodiments, the solution may comprise substituted or unsubstituted polygalacturonic acid and a multivalent cation (e.g., a calcium salt or magnesium salt) at a concentration in the range of 5 mM to 25 mM.

In some embodiments, the solution may comprise a protoporphyrin, e.g., a protoporphyrin IX or an analog thereof such as octaethylporphyrin ($H_2OEP$) or tetraphenylporphyrin ($H_2TPP$), complexed with a metal ion. In these embodiments, the protoporphyrin may be hemin (protoporphyrin IX containing a ferric iron ($Fe^t$) ion with a coordinating chloride ligand) or hematin. In other embodiments, the protoporphyrin may be protoporphyrin IX complexed with a divalent or trivalent cation (e.g., $Zn^{2+}$, $Cr^{3+}$, or $Co^{3+}$, for example). In these embodiments, the protoporhyrin may in the solution at a concentration in the range of 0.1 µM to 100 µM (e.g., 1 µM to 10 µM). In some embodiments, the solution may comprise an HRP stabilization component selected from HRP Conjugate Stabilizer (PN 85R-102; Fitzgerald Industries), HRP Conjugate Stabilizer (PN SZ02; Surmodics) and HRP Conjugate Stabilizer (PN ab171537; Abcam). Other HRP stabilization components, e.g., AbGuard (BioRad PN: BUF052; BioRad Laboratories Inc. 2000 Alfred Nobel Dr, Hercules, Calif. 94547) can potentially be used. If the solution comprises an HRP stabilization component, then the component may be at a concentration in the range of 1% to 20%, e.g., 5% to 15% or 5% to 20%.

In any embodiment, the solution may comprise a polyvalent cation, e.g., calcium or magnesium ions. In these embodiments, the polyvalent cation may be at a concentration in the range of 5 mM to 25 mM.

In any embodiment, the solution further comprises Tris buffer (e.g., 10 mM to 50 mM Tris, pH 7.5), bovine serum albumen (e.g., 5% to 20% BSA), polysorbate 20 (e.g., 0.05% to 0.2% polysorbate 20), a preservative such as sodium azide (e.g., 0.05% to 0.2% sodium azide), a salt such as sodium chloride (e.g., 50 mM to 250 mM sodium chloride), a chelator such as ethylenediaminetetraacetic acid (e.g., 5 mM to 20 mM ethylenediaminetetraacetic acid), and an antibiotic such as gentamicin (e.g., 5 ug/mL to 50 ug/mL).

A composition comprising: (a) a stool sample and (b) the stool resuspension solution, as described above, is also provided. The stool sample may be suspended in the solution. Some components of the stool may be dissolved in the solution, where other, insoluble components, may be suspended but not dissolved in the solution. In some embodiments, the stool sample may contain hemoglobin which may be dissolved in the solution. In these embodiments, the presence of the hemoglobin stabilization reagent may increase the amount of hemoglobin in the sample after it has been subjected to a real or simulated shipping stress, as described below, as compared to an otherwise identical control sample that has not been subjected to the stress, e.g., a "$T_0$" sample. In some embodiments, use of the hemoglobin stabilization reagent may increase the amount of hemoglobin in the sample by at least 10%, at least 20 or at least 30%, relative to a control stool sample that has been suspended in an otherwise identical solution that does not contain the hemoglobin stabilization reagent. The amount of hemoglobin in the sample may be determined by enzyme-linked immunosorbent assay (ELISA) although several other methods are known (see, generally, Haug et al, Am J. Gastroenterology 105: 682-690; Ahlquist et al, Ann Intern Med 1984; 101:297-302; Ahlquist et al, JAMA 1993 269:1262-1267; Young et al Dig Dis Sci. 2015 60: 609-622; and Harewood et al Mayo Clin. Proc. 2002 77: 23-28).

Also provided is a method of stabilizing stool hemoglobin. In some embodiments, this method may comprise combining the stool sample with the stool resuspension solution as described above, i.e., a solution comprising one or more hemoglobin stabilization reagents selected from: an osmolyte, a polyvalent cation, a sugar or polysaccharide and, optionally, a polyvalent cation; a protoporphyrin; and an HRP stabilization component and, optionally, a polyvalent cation, to produce a suspension; and maintaining the suspension for a period of time. Details of the identities of the reagents that can be in the solution as well as their concentrations are described above, below and in the accompanying appendices. In some embodiments, the method may comprise obtaining the stool sample from a larger mass of stool by scraping or scooping, e.g., using a stool sampling implement.

In some embodiments, the method may comprise shipping the sample to a remote location, e.g., to another town, city, state or country, for testing. In these embodiments, the sample may be waiting to be shipped, en route, or waiting to be tested at a remote location for several days, e.g., 3, 4, 5, 6, or 7 days, thereby subjecting the sample to stresses that potentially reduce the amount of hemoglobin in the sample.

Also provided is a method that comprises receiving a composition that comprises: (a) a stool sample and (b) a stool resuspension solution comprising one or more hemoglobin stabilization reagents selected from, e.g., an osmolyte, a polyvalent cation, a sugar or polysaccharide and, optionally, a polyvalent cation, a protoporphyrin, and an HRP stabilization component and, optionally, a polyvalent cation. Examples and concentrations of such reagents in the solution are set forth above, below and in the accompanying appendices. In certain embodiments, this method may further comprise performing an assay on the sample after it has been received. For example, the concentration of hemoglobin in the solution may be measured, methods for performing which are described above. In addition, the amount of one or more colorectal cancer tumor markers in the sample may be tested after it has been received (see, generally, Lech et al, World J Gastroenterol. 2016 22: 1745-1755 and Scheruders et al, Curr. Treat. Options Gastroenterol. 2016 14: 152-162). These embodiments may further comprise forwarding test results to a remote location by, e.g., fax or e-mail, etc., or via the internet via a portal, so that the results can be obtained by a medical practitioner (e.g., an MD or a nurse, etc.), in advance of providing a diagnosis to the patient from which the stool sample was obtained.

Also provided is a sample collection device that comprises: (a) a sample collection container having an open end; (b) a stool resuspension solution that is within the container, where the solution comprises one or more hemoglobin stabilization reagents selected from: an osmolyte, a polyvalent cation, a sugar or polysaccharide and, optionally, a polyvalent cation, a protoporphyrin, and an HRP stabilization component and, optionally, a polyvalent cation, as described herein; and (c) a stool sampling rod comprising a distal beveled tip for scooping and/or scraping a sample of stool. In this device, the distal end of the sampling rod is dimensioned to be inserted into the sample collection container and the proximal end of the sampling rod is adapted to connect with the open end of the sample collection container, thereby sealing distal end of the sampling rod within the device. In some embodiments, the sample collection container and sampling rod may connect via a screw fit. With the exception of the hemoglobin stabilization reagent, details, options and the design of an example of such a sample collection device can be found in U.S. Pat. No. 9,211,112, for example. In some embodiments, the device may comprise a) a body comprising a sample collection chamber bounded on a distal end by a penetrable seal affixed to a recessed sealing surface of the distal end of the body and bounded on a proximal end by a septum comprising an aperture, said penetrable seal being penetrable by a pipette tip or needle; b) a flexible sampling rod comprising a proximal portion and a distal portion, said sampling rod adapted to fit through and seal said aperture when said distal portion is in said sample collection chamber, wherein said distal portion comprises: i) an asymmetrical beveled tip at a distal end, said beveled tip having an apex at the circumference of the flexible sampling rod and configured to bend the flexible sampling rod away from collisions and/or to deflect collisions with an inserted pipette tip or needle; and ii) a plurality of stacked coaxial frusta of cones to form a plurality of metering ridges; and c) the stool resuspension solution described above in the sample collection chamber, as described in U.S. Pat. No. 9,211,112.

Embodiments

Embodiment 1. A composition comprising: (a) a stool sample; and (b) a stool resuspension solution comprising one or more hemoglobin stabilization reagents selected from: a protoporphyrin; a polyvalent cation; a sugar or polysaccharide and, optionally, a polyvalent cation; an osmolyte; and an HRP stabilization component and, optionally, a polyvalent cation.

Embodiment 2. The composition of embodiment 1, wherein the stool sample contains hemoglobin.

Embodiment 3. The composition of embodiment 1, wherein the solution comprises betaine.

Embodiment 4. The composition of embodiment 2, wherein the betaine is at a concentration in the range of 2 M to 5 M.

Embodiment 5. The composition of embodiment 1, wherein the solution comprises sucrose or trehalose, and, optionally, a polyvalent cation.

Embodiment 6. The composition of embodiment 5, wherein the sucrose or trehalose is at a concentration in the range of 0.1 M to 0.5 M and the solution, optionally comprises, a polyvalent cation.

Embodiment 7. The composition of embodiment 1, wherein the solution comprises substituted or unsubstituted polygalacturonic acid and, optionally, a polyvalent cation.

Embodiment 8. The composition of embodiment 1 or 7, wherein the solution comprises α-(1-4)-linked D-galacturonic acid and, optionally, a polyvalent cation.

Embodiment 9. The composition of embodiment 7, wherein the substituted or unsubstituted polygalacturonic acid is at a concentration in the range of 0.005% to 0.5%.

Embodiment 10. The composition of embodiment 1, wherein the solution comprises substituted or unsubstituted polygalacturonic acid and a multivalent cation (e.g., a calcium salt or magnesium salt) at a concentration in the range of 5 mM to 25 mM.

Embodiment 11. The composition of embodiment 1, wherein the solution comprises a protoporphyrin.

Embodiment 12. The composition of embodiment 11, wherein the protoporphyrin is hemin or hematin.

Embodiment 13. The composition of embodiment 11, wherein the protoporphyrin comprises protoporphyrin IX complexed with a divalent or trivalent cation (e.g., $Zn^{2+}$, $Cr^{3+}$ or $Co^{3}\pm$).

Embodiment 14. The composition of any of embodiments 11-13, wherein the protoporphyrin is at a concentration in the range of 0.1 μM to 100 μM (e.g., 1 μM to 10 μM).

Embodiment 15. The composition of embodiment 1, wherein the solution comprises an HRP stabilization component selected from HRP Conjugate Stabilizer (PN 85R-102; Fitzgerald Industries), HRP Conjugate Stabilizer (PN SZ02; Surmodics) and HRP Conjugate Stabilizer (PN ab171537; Abcam)

Embodiment 16. The composition of embodiment 15, wherein the HRP stabilization component is at a concentration in the range of 1% to 20%.

Embodiment 17. The composition of any prior embodiment, wherein the solution comprises one or more cations selected from iron, cobalt, chromium, zinc, calcium or magnesium ions.

Embodiment 18. The composition of embodiment 17, wherein the cations are at a concentration in the range of 5 mM to 25 mM.

Embodiment 19. The composition of any prior embodiment, wherein the stool sample is suspended in the solution.

Embodiment 20. The composition of any prior embodiment, wherein the solution further comprises Tris buffer, bovine serum albumen, polysorbate 20, sodium azide, sodium chloride, ethylenediaminetetraacetic acid, and gentamicin.

Embodiment 21. A method of stabilizing hemoglobin in a stool sample, comprising: combining the stool sample with a stool resuspension solution comprising one or more hemoglobin stabilization reagents selected from: a protoporphyrin; a polyvalent cation; a sugar or polysaccharide and, optionally, a polyvalent cation; an osmolyte; and an HRP stabilization component and, optionally, a polyvalent cation; to produce a suspension; and maintaining the suspension for a period of time.

Embodiment 22. The method of embodiment 17, wherein the method comprises shipping the suspension to a remote location.

Embodiment 23. A method of analyzing a stool sample, comprising: (a) receiving, from a remote location, a composition comprising: (i) a stool sample; and (ii) a stool resuspension solution comprising one or more hemoglobin stabilization reagents selected from: a protoporphyrin; a polyvalent cation; a sugar or polysaccharide and, optionally, a polyvalent cation; an osmolyte; and an HRP stabilization component and, optionally, a polyvalent cation, wherein the stool sample is suspended in the solution; and (b) measuring the amount of hemoglobin in the composition.

Embodiment 24. The method of embodiment 19, further comprising measuring the amount of one or more colorectal cancer tumor markers in the sample.

Embodiment 25. A sample collection device comprising: a sample collection container having an open end; a stool resuspension solution that is within the container, comprising one or more hemoglobin stabilization reagents selected from: a protoporphyrin; a polyvalent cation; a sugar or polysaccharide and, optionally, a polyvalent cation; an osmolyte; and an HRP stabilization component and, optionally, a polyvalent cation; and a stool sampling rod comprising a distal beveled tip for scooping and/or scraping a sample of stool, wherein the distal end of the sampling rod is dimensioned to be inserted into the sample collection container and the proximal end of the sampling rod is adapted to connect with the open end of the sample collection container, thereby sealing distal end of the sampling rod within the device.

Embodiment 26. The sample collection device of embodiment 25, wherein the sample collection container and sampling rod connect via a screw fit.

Embodiment 27. A method of stabilizing hemoglobin in a stool sample, comprising: combining the stool sample with a stool resuspension solution comprising protoporphyrin IX complexed with a multivalent cation to produce a suspension; and maintaining the suspension for a period of time.

Embodiment 28. The method of embodiment 27, wherein the method comprises shipping the suspension to a remote location.

Embodiment 29. A method of analyzing a stool sample, comprising: (a) receiving, from a remote location, a composition comprising: (i.) a stool sample; and (ii.) a stool resuspension solution comprising protoporphyrin IX complexed with a multivalent cation, wherein the stool sample is suspended in the solution; and (b) measuring the amount of hemoglobin in the composition.

Embodiment 30. The method of any of embodiments 27-29, further comprising measuring the amount of one or more colorectal cancer tumor markers in the sample.

Embodiment 31. The method of any of embodiments 27-30, wherein the multivalent cation is $Cr^{3+}$ or $Co^{3+}$.

Embodiment 32. The method of any of embodiments 27-31, wherein the solution has a pH in the range of pH 6.5 to pH 7.4.

Embodiment 33. The method of any of embodiments 27-32, wherein the multivalent cation is $Cr^{3+}$ and the pH of the solution is in the range of pH 6.9 to pH 7.4.

Embodiment 34. The method of any of embodiments 27-32, wherein the multivalent cation is $Co^{3+}$ and the pH of the solution is in the range of pH 6.5 to pH 7.0.

Embodiment 35. The method of any of embodiments 27-34, wherein the protoporphyrin IX is at a concentration in the range of 0.5 μM to 10 μM.

Embodiment 36. A sample collection device comprising: a sample collection container having an open end; a stool resuspension solution comprising protoporphyrin IX complexed with a multivalent cation; and a stool sampling rod comprising a distal beveled tip for scooping and/or scraping a sample of stool, wherein the distal end of the sampling rod is dimensioned to be inserted into the sample collection container and the proximal end of the sampling rod is adapted to connect with the open end of the sample collection container, thereby sealing distal end of the sampling rod within the device.

Embodiment 37. The sample collection device of embodiment 36, wherein the sample collection container and sampling rod connect via a screw fit.

Embodiment 38. The sample collection device of embodiment 36 or 37, wherein the multivalent cation is $Cr^{3+}$ or $Co^{3+}$.

Embodiment 39. The sample collection device of any of embodiments 36-38, wherein the solution has a pH in the range of pH 6.5 to pH 7.4.

Embodiment 40. The sample collection device of any of embodiments 36-39, wherein the multivalent cation is $Cr^{3+}$ and the pH of the solution is in the range of pH 6.9 to pH 7.4.

Embodiment 41. The sample collection device of any of embodiments 36-39, wherein the multivalent cation is $Co^{3+}$ and the pH of the solution is in the range of pH 6.5 to pH 7.0.

Embodiment 42. The sample collection device of any of embodiments 16-21, wherein the protoporphyrin IX is at a concentration in the range of 0.5 μM to 10 μM.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1

Simulated Shipping Stress

To assess the stability of hemoglobin in stool samples, samples were exposed to simulated shipping stress conditions using a thermal cycler. Table 1 shows the time and temperature profile for a 3-Day (72 hour) shipping simulation. An ELISA based detection method is used to determine the hemoglobin concentrations of samples before and after exposure to the shipping simulation. Hemoglobin stability is calculated as a % recovery of hemoglobin after the samples have been exposed to the shipping simulation.

TABLE 1

3-Day Shipping Simulation

| Simulated Shipping Condition | Duration (hrs) | Total time (hrs) | Temp (° C.) |
| --- | --- | --- | --- |
| Pre-shipping hold at ambient temperature | 24 | 24 | 22 |
| Ambient, overnight shipping | 9 | 33 | 22 |
| | 3 | 36 | 35 |
| | 4 | 40 | 22 |
| | 5 | 45 | 35 |
| | 5 | 50 | 22 |
| | 4 | 54 | 35 |
| Post-shipping hold at ambient temperature | 18 | 72 | 22 |

An accelerated shipping simulation profile was created to mimic the 3-Day shipping simulation but in a shortened amount of time. Table 2 shows the time and temperature profile for an accelerated shipping simulation. Samples exposed to the accelerated shipping simulation exhibit similar levels of Hb stability as when exposed to the 3-Day shipping simulation.

TABLE 2

Accelerated Shipping Simulation

| Simulated Shipping Condition | Duration (hrs) | Temp (° C.) |
| --- | --- | --- |
| Incubation at Temperature | 16 | 35 |

To assess the stability of hemoglobin in stool samples beyond 3 days, a 7-Day shipping simulation was created. Table 3 shows the time and temperature profile for a 7-Day shipping simulation.

TABLE 3

7-Day Shipping Simulation

| Simulated Shipping Condition | Duration (hrs) | Total time (hrs) | Temp (° C.) |
|---|---|---|---|
| Pre-shipping hold at ambient temperature | 40 | 40 | 22 |
| Ambient, overnight shipping | 9 | 49 | 22 |
| | 3 | 52 | 35 |
| | 4 | 56 | 22 |
| | 5 | 61 | 35 |
| | 5 | 66 | 22 |
| | 4 | 70 | 35 |
| Post-shipping hold at ambient temperature | 2 | 72 | 22 |
| | 48 | 120 | 22 |
| | 48 | 168 | 22 |

As an additional challenge, a shipping simulation meant to represent a "worst case" scenario was created using extreme temperatures. Table 4 show the time and temperature profile for a 3-Day extreme temperature shipping simulation.

TABLE 4

3-Day Extreme Temperature Shipping Simulation

| Simulated Shipping Condition | Duration (hrs) | Total time (hrs) | Temp (° C.) |
|---|---|---|---|
| Pre-shipping hold at ambient temperature | 16 | 16 | 22 |
| Extreme High Temperature overnight shipping | 2.17 | 18.17 | 43.5 |
| | 6.17 | 24.34 | 33 |
| | 5 | 29.34 | 34 |
| | 1.83 | 31.17 | 32.5 |
| | 1.5 | 32.67 | 27.5 |
| | 1.67 | 34.34 | 38.5 |
| | 2.83 | 37.17 | 33 |
| | 2.83 | 40 | 37 |
| Post-shipping hold at ambient temperature | 32 | 72 | 22 |

Assay Results

The performance of the existing buffer formulation (shown below) was tested. The average percent hemoglobin recovery across all samples was determined for days 3, 5, and 7 of the 7-Day shipping simulation. These results are shown below.

| Final Concentration | Component |
|---|---|
| N/A | Water |
| 20 mM | 1M Tris pH 7.5 |
| 10% | BSA |
| 0.10% | 20% Tween 20 |
| 0.095% | 5% Sodium Azide |
| 140 mM | Sodium Chloride |
| 10 mM | 0.5M EDTA |
| 15 µg/mL | 50 mg/mL Gentamicin |

Results are listed in the table below.

| Timepoint | % Hb Recovery |
|---|---|
| Day 3 | 71 |
| Day 5 | 68 |
| Day 7 | 63 |

The desired % Hb Recovery at 7 days is minimally 70%. As such, the existing buffer formulation does not achieve the desired level of stability beyond 3 days (72 hours).

In an effort to improve hemoglobin stability, several classes of compounds (see Appendix A) were evaluated as additives to the base buffer formulation (also referred to herein as the existing buffer formulation) described above.

These compounds were tested at various concentrations and in combination. A list of the compounds tested using the accelerated shipping simulation and the results of these assays are found in Appendix B. A list of the compounds tested using the 3-day shipping simulation and their results are found in Appendix C. A list of the combinations of compounds that were tested is shown in Appendix D.

Of the compounds evaluated, several were identified that show potential in enhancing the stability of hemoglobin as additives to the existing buffer formulation. These compounds are listed in the table below:

| Compound Classification | Compound |
|---|---|
| Sugars/Saccharides | Trehalose |
| | Sucrose |
| | Polygalacturonic Acid (Pectic Acid) |
| Osmolytes/ Extremolytes | Betaine |
| | Trimethylamine N-oxide |
| Polyvalent Ions/ Metal Salts | Magnesium Sulfate |
| | Calcium Chloride |
| HRP Stabilizer Components | HRP Conjugate Stabilizer (PN 85R-102) |
| | HRP Conjugate Stabilizer (PN SZ02) |
| | HRP Conjugate Stabilizer (PN ab171537) |

The compounds demonstrating the most potential for enhancing Hb stability from the accelerated shipping and other simulations were tested on three stool samples in several different shipping simulations. These results are shown below.

In a 3-Day (72 hour) shipping simulation the potential additives demonstrate improved stability over the existing formulation (Hb Collection Buffer). See the following table:

3-Day Shipping Simulation

| Compound Classification | Additive | Additive Concentration | % Hb Recovery | Notes |
|---|---|---|---|---|
| Hb Collection Buffer | | NA | 75 | Current formulation |
| Polymedco (Eiken) Buffer | | NA | 81 | |
| Osmolytes | Betaine | 3.5M | 78 | Improved Hb Stability |

| 3-Day Shipping Simulation | | | | |
|---|---|---|---|---|
| Compound Classification | Additive | Additive Concentration | % Hb Recovery | Notes |
| Sugars/Saccharides | Sucrose | 0.24M | 75 | Improved Hb Stability |
| Sugars/Saccharides | Trehalose | 0.3M | 77 | Improved Hb Stability |
| Polyvalent Ions/Metal Salts | Calcium Chloride | 10 mM | 77 | Improved Hb Stability |
| Polyvalent Ions/Metal Salts | Magnesium Sulfate | 10 mM | 79 | Improved Hb Stability |
| HRP Stabilization Components | HRP Conjugate Stabilizer (PN 85R-102) | 15% | 77 | Improved Hb Stability |
| HRP Stabilization Components + Polyvalent Ions | HRP Conjugate Stabilizer (PN 85R-102) + CaCl2 | 15% + 10 mM | 97 | Improved Hb Stability |
| HRP Stabilization Components + Polyvalent Ions | HRP Conjugate Stabilizer (PN 85R-102) + MgSO4 | 15% + 10 mM | 87 | Improved Hb Stability |
| HRP Stabilization Components | HRP Conjugate Stabilizer (PN SZ02) | 15% | 76 | Improved Hb Stability |
| HRP Stabilization Components + Polyvalent Ions | HRP Conjugate Stabilizer (PN SZ02) + CaCl2 | 15% + 10 mM | 88 | Improved Hb Stability |
| HRP Stabilization Components + Polyvalent Ions | HRP Conjugate Stabilizer (PN SZ02) + MgSO4 | 15% + 10 mM | 92 | Improved Hb Stability |

The HRP (horse radish peroxidase) stabilizers tested and shown in the tables are:

HRP Conjugate Stabilizer (PN 85R-102), Fitzgerald Industries International, 30 Sudbury Road, Suite 1A North, Acton, Mass., 01720 USA HRP Conjugate Stabilizer (PN SZ02), Surmodics, Inc., 9924 West 74th Street, Eden Prairie, Minn. 55344 USA HRP Conjugate Stabilizer (PN ab171537), Abcam, 1 Kendall Square, Cambridge, Mass. 02139 USA In a 7-Day shipping simulation the potential additives demonstrate improved stability over the existing formulation (Hb Collection Buffer). See the following Table:

| 7-Day Shipping Simulation | | | | | | |
|---|---|---|---|---|---|---|
| Compound Classification | Additive | Additive Concentration | % Hb Recovery Day 3 | % Hb Recovery Day 5 | % Hb Recovery Day 7 | Notes |
| Hb Collection Buffer | | NA | 71 | 68 | 63 | Current formulation |
| Polymedco Buffer | | NA | 83 | 83 | 80 | |
| Polyvalent Ions/Metal Salts | Calcium Chloride | 10 mM | 77 | 75 | 73 | Improved Hb Stability |
| Polyvalent Ions/Metal Salts | Magnesium Sulfate | 10 mM | 76 | 74 | 71 | Improved Hb Stability |
| Osmolytes | Betaine | 3.5M | 78 | 74 | 70 | Improved Hb Stability |
| HRP Stabilization Components | HRP Conjugate Stabilizer (PN 85R-102) | 15% | 80 | 75 | 69 | Improved Hb Stability |
| HRP Stabilization Components + Polyvalent Ions | HRP Conjugate Stabilizer (PN 85R-102) + CaCl2 | 15% + 10 mM | 89 | 88 | 82 | Improved Hb Stability |
| HRP Stabilization Components + Polyvalent Ions | HRP Conjugate Stabilizer (PN 85R-102) + MgSO4 | 15% + 10 mM | 89 | 88 | 82 | Improved Hb Stability |
| HRP Stabilization Components | HRP Conjugate Stabilizer (PN SZ02) | 15% | 80 | 70 | 61 | Improved Hb Stability |
| HRP Stabilization Components + Polyvalent Ions | HRP Conjugate Stabilizer (PN SZ02) + CaCl2 | 15% + 10 mM | 86 | 83 | 78 | Improved Hb Stability |
| HRP Stabilization Components + Polyvalent Ions | HRP Conjugate Stabilizer (PN SZ02) + MgSO4 | 15% + 10 mM | 90 | 85 | 79 | Improved Hb Stability |

In a 3-Day extreme temperature shipping simulation the potential additives demonstrate improved stability over the existing formulation (Hb Collection Buffer). Additives containing HRP stabilization buffer and Calcium Chloride or Magnesium Sulfate also demonstrate improved Hb stability compared to the Polymedco buffer. See following Table:

| 3-Day Extreme Temperature Shipping Simulation | | | | |
|---|---|---|---|---|
| Compound Classification | Additive | Additive Concentration | % Hb Recovery | Notes |
| Hb Collection Buffer | NA | NA | 47 | Current formulation |
| Polymedco Buffer | NA | NA | 67 | |
| Polyvalent Ions/ Metal Salts | Calcium Chloride | 10 mM | 58 | Improved Hb Stability |
| Polyvalent Ions/ Metal Salts | Magnesium Sulfate | 10 mM | 54 | Improved Hb Stability |
| Osmolytes | Betaine | 3.5M | 61 | Improved Hb Stability |
| HRP Stabilization Components | HRP Conjugate Stabilizer (PN 85R-102) | 15% | 56 | Improved Hb Stability |
| HRP Stabilization Components + Polyvalent Ions | HRP Conjugate Stabilizer (PN 85R-102) + CaCl2 | 15% and 10 mM | 77 | Improved Hb Stability |
| HRP Stabilization Components + Polyvalent Ions | HRP Conjugate Stabilizer (PN 85R-102) + MgSO4 | 15% and 10 mM | 71 | Improved Hb Stability |

In an accelerated shipping simulation, the additive polygalacturonic acid (with calcium chloride) is demonstrating improved Hb stability over the existing formulation (Hb Collection Buffer) at different concentrations. See the following table:

| Accelerated Shipping Simulation | | | | |
|---|---|---|---|---|
| Compound Classification | Additive | Additive Concentration | % Hb Recovery | Notes |
| Hb Collection Buffer | NA | NA | 72 | Current formulation |
| Sugars/ Saccharides | Polygalacturonic Acid + Calcium Chloride | 0.01% + 10 mM | 83 | Improved Hb Stability |
| | Polygalacturonic Acid + Calcium Chloride | 0.025% + 10 mM | 91 | Improved Hb Stability |
| | Polygalacturonic Acid + Calcium Chloride | 0.05% + 10 mM | 86 | Improved Hb Stability |
| | Polygalacturonic Acid + Calcium Chloride | 0.075% + 10 mM | 79 | Improved Hb Stability |
| | Polygalacturonic Acid + Calcium Chloride | 0.1% + 10 mM | 64 | No Improvement |
| | Polygalacturonic Acid + Calcium Chloride | 0.125% + 10 mM | 86 | Improved Hb Stability |

Another class of compounds called protoporphyrins was tested and can enhance the stability of hemoglobin when added to the existing buffer formulation. The protoporphyrins tested are shown in the table below. Note that in some test cases the pH was altered as solubility of protoporphyrins is known to be sensitive to pH.

TABLE 14

| Additional Potential Compounds | |
|---|---|
| Compound Classification | Compound |
| Protoporphyrins | Protoporphyrin IX Zinc |
| | Protoporphyrin IX Cobalt |
| | Protoporphyrin IX Chromium |
| | Hemin (Protoporphyrin IX Iron) |
| | Hematin (Protoporphyrin IX Iron) |

In a 3-Day (72 hour) shipping simulation the existing formulation with added protoporphyrin provided improved stability over the existing formulation without any protoporphyrin). These results are shown in the table below.

| Compound Classification | Additive | Additive Concentration | % Hb Recovery | Notes |
|---|---|---|---|---|
| Hb Collection Buffer | | NA | 70 | Current formulation |
| Polymedco (Eiken) Buffer | | NA | 80 | |
| Protoporphyrin | Hemin (Buffer pH 6.5) | 0.0003% (4.8 μM) | 88 | Improved Hb Stability |
| Protoporphyrin | Hemin (Buffer pH 7.4) | 0.0003% (4.8 μM) | 78 | Improved Hb Stability |
| Protoporphyrin | Protoporphyrin IX Zn (Buffer pH 6.5) | 1 μM | 89 | Improved Hb Stability |
| Protoporphyrin | Protoporphyrin IX Zn (Buffer pH 7.4) | 1 μM | 75 | Improved Hb Stability |
| Protoporphyrin | Protoporphyrin IX Cr (Buffer pH 6.5) | 2.5 μM | 117 | Improved Hb Stability |
| Protoporphyrin | Protoporphyrin IX Cr (Buffer pH 7.4) | 2.5 μM | 102 | Improved Hb Stability |
| Protoporphyrin | Protoporphyrin IX Co (Buffer pH 6.5) | 5 μM | 109 | Improved Hb Stability |
| Protoporphyrin | Protoporphyrin IX Co (Buffer pH 7.4) | 5 μM | 111 | Improved Hb Stability |

In a 7-day shipping simulation the existing formulation with added protoporphyrin provided improved stability over the existing formulation without any protoporphyrin. These results are shown in the table below.

7-Day Shipping Simulation

| Compound Classification | Additive | Additive Concentration | % Hb Recovery Day 3 | % Hb Recovery Day 5 | % Hb Recovery Day 7 | Notes |
|---|---|---|---|---|---|---|
| Hb Collection Buffer | | NA | 70 | 64 | 60 | Current formulation |
| Polymedco (Eiken) Buffer | | NA | 83 | 82 | 80 | |
| Protoporphyrin | Hemin (Buffer pH 6.5) | 0.0003% (4.8 μM) | 85 | 81 | 80 | Improved Hb Stability |
| Protoporphyrin | Hemin (Buffer pH 7.4) | 0.0003% (4.8 μM) | 78 | 77 | 68 | Improved Hb Stability |
| Protoporphyrin | Protoporphyrin IX Zn (Buffer pH 6.5) | 1 μM | 84 | 83 | 80 | Improved Hb Stability |
| Protoporphyrin | Protoporphyrin IX Zn (Buffer pH 7.4) | 1 μM | 73 | 70 | 65 | Improved Hb Stability |
| Protoporphyrin | Protoporphyrin IX Cr (Buffer pH 6.5) | 2.5 μM | 109 | 113 | 110 | Improved Hb Stability |
| Protoporphyrin | Protoporphyrin IX Cr (Buffer pH 7.4) | 2.5 μM | 93 | 91 | 90 | Improved Hb Stability |
| Protoporphyrin | Protoporphyrin IX Co (Buffer pH 6.5) | 5 μM | 101 | 104 | 104 | Improved Hb Stability |
| Protoporphyrin | Protoporphyrin IX Co (Buffer pH 7.4) | 5 μM | 103 | 99 | 93 | Improved Hb Stability |

Adding protoporphyrins to the existing formulation (Hb Collection Buffer) also improves Hb stability in 3-Day extreme temperature shipping simulation. In addition, additives containing protoporphyrin cobalt (Co) or protoporphyrin chromium (Cr) demonstrate improved Hb stability compared to the Polymedco buffer. See the table below:

3-Day Extreme Temperature Shipping Simulation

| Compound Classification | Additive | Additive Concentration | % Hb Recovery | Notes |
|---|---|---|---|---|
| Hb Collection Buffer | NA | NA | 46 | Current formulation |
| Polymedco Buffer | NA | NA | 69 | |
| Protoporphyrin | Hemin (Buffer pH 6.5) | 0.0003% (4.8 μM) | 67 | Improved Hb Stability |
| Protoporphyrin | Hemin (Buffer pH 7.4) | 0.0003% (4.8 μM) | 54 | Improved Hb Stability |
| Protoporphyrin | Protoporphyrin IX Zn (Buffer pH 6.5) | 1 μM | 64 | Improved Hb Stability |
| Protoporphyrin | Protoporphyrin IX Cr (Buffer pH 6.5) | 2.5 μM | 92 | Improved Hb Stability |
| Protoporphyrin | Protoporphyrin IX Cr (Buffer pH 7.4) | 2.5 μM | 68 | Improved Hb Stability |
| Protoporphyrin | Protoporphyrin IX Co (Buffer pH 6.5) | 5 μM | 81 | Improved Hb Stability |
| Protoporphyrin | Protoporphyrin IX Co (Buffer pH 7.4) | 5 μM | 73 | Improved Hb Stability |

Further Testing of Protoporphyrin

Protoporphyrin IX was tested at various concentrations and pHs using the 7-Day Modified Shipping Simulation conditions listed below as well as other conditions.

7-Day Modified Shipping Simulation

| Simulated Shipping Condition | Duration (hrs) | Total Time (hrs) | Temp (° C.) |
|---|---|---|---|
| Pre-shipping hold at ambient temperature | 72 | 72 | 22 |
| Pre-shipping temperature spike | 8 | 80 | 35 |
| Pre-shipping hold at ambient temperature | 16 | 96 | 22 |
| Ambient, overnight shipping | 24 | 120 | 22 |
| | 9 | 129 | 22 |
| | 3 | 132 | 35 |
| | 4 | 136 | 22 |
| | 5 | 141 | 35 |
| | 5 | 146 | 22 |
| | 4 | 150 | 35 |
| Post-shipping hold at ambient temperature | 18 | 168 | 22 |

The following table shows that buffers containing Cobalt (III) PPIX (Protoporphyrin IX) at concentrations of 3-6 μM at an adjusted pH range of 6.4-7.0 provide increased Hb stability in the 7-Day Modified Shipping Simulation.

7-Day Modified Shipping Simulation

| Compound Classification | Additive | Additive Conc. | Buffer pH | % Hb Recovery | Notes |
|---|---|---|---|---|---|
| Hb Collection Buffer | NA | NA | 7.4 | 59.4 | Current Formulation |
| Polymedco Buffer (Eiken) | NA | NA | NA | 70 | |
| Protoporphyrins | Protoporphyrin IX Co | 3 μM | 6.9 | 75.0 | Improved Hb Stability |
| | Protoporphyrin IX Co | 3.5 μM | 6.9 | 82.2 | Improved Hb Stability |
| | Protoporphyrin IX Co | 4 μM | 6.4 | 100.0 | Improved Hb Stability |
| | Protoporphyrin IX Co | 4 μM | 6.6 | 94.8 | Improved Hb Stability |
| | Protoporphyrin IX Co | 4 μM | 6.8 | 93.3 | Improved Hb Stability |
| | Protoporphyrin IX Co | 4 μM | 6.9 | 84.8 | Improved Hb Stability |
| | Protoporphyrin IX Co | 4 μM | 7.0 | 87.7 | Improved Hb Stability |
| | Protoporphyrin IX Co | 4.5 μM | 6.9 | 84.6 | Improved Hb Stability |
| | Protoporphyrin IX Co | 5 μM | 6.4 | 105.0 | Improved Hb Stability |
| | Protoporphyrin IX Co | 5 μM | 6.6 | 102.0 | Improved Hb Stability |
| | Protoporphyrin IX Co | 5 μM | 6.8 | 95.5 | Improved Hb Stability |

| 7-Day Modified Shipping Simulation | | | | | |
|---|---|---|---|---|---|
| Compound Classification | Additive | Additive Conc. | Buffer pH | % Hb Recovery | Notes |
| | Protoporphyrin IX Co | 5 μM | 6.9 | 84.1 | Improved Hb Stability |
| | Protoporphyrin IX Co | 5 μM | 7.0 | 95.7 | Improved Hb Stability |
| | Protoporphyrin IX Co | 6 μM | 6.4 | 110.0 | Improved Hb Stability |
| | Protoporphyrin IX Co | 6 μM | 6.6 | 106.0 | Improved Hb Stability |
| | Protoporphyrin IX Co | 6 μM | 6.8 | 101.0 | Improved Hb Stability |
| | Protoporphyrin IX Co | 6 μM | 7.0 | 95.0 | Improved Hb Stability |

The following table shows that buffers containing Cobalt (III) PPIX (Protoporphyrin IX) at concentrations of 2.5-10 μM at an adjusted pH of 6.8 provide increased Hb stability in the 3 and 7 day Shipping Simulations.

The following table shows that buffers containing Chromium(III) PPIX (Protoporphyrin IX) at concentrations of 0.5-10 μM at an adjusted pH of 7.1 provide increased Hb stability in the 3 and 7 day Shipping Simulations.

| 3-Day and 7-Day Shipping Simulation | | | | | | |
|---|---|---|---|---|---|---|
| Compound Class | Additive | Additive Conc. | Buffer pH | 3-Day % Hb Recovery | 7-Day % Hb Recovery | Notes |
| Hb Collection Buffer | NA | NA | 7.4 | 61.5 | 54.8 | Current Formulation |
| Protoporphyrin | Protoporphyrin IX Co | 2.5 μM | 6.8 | 80.2 | 79.5 | Improved Hb Stability |
| | | 3 μM | 6.8 | 76.0 | 73.4 | Improved Hb Stability |
| | | 5 μM | 6.8 | 82.8 | 82.7 | Improved Hb Stability |
| | | 7 μM | 6.8 | 86.5 | 83.7 | Improved Hb Stability |
| | | 7.5 μM | 6.8 | 92.9 | 94.8 | Improved Hb Stability |
| | | 10 μM | 6.8 | 95.5 | 101.3 | Improved Hb Stability |
| | Protoporphyrin IX Cr | 0.5 μM | 7.1 | 75.0 | 65.6 | Improved Hb Stability |
| | | 2.5 μM | 7.1 | 86.3 | 78.9 | Improved Hb Stability |
| | | 4.5 μM | 7.1 | 94.5 | 86.4 | Improved Hb Stability |
| | | 5 μM | 7.1 | 97.0 | 99.4 | Improved Hb Stability |
| | | 7.5 μM | 7.1 | 108.7 | 112.7 | Improved Hb Stability |
| | | 10 μM | 7.1 | 116.8 | 113.8 | Improved Hb Stability |

The following table shows that buffers containing Cobalt (III) PPIX (Protoporphyrin IX) at concentrations of 2.5-10 μM at an adjusted pH range of 6.2-7.4 provide increased Hb stability in the 35 C 16 hour challenge.

The following table shows that buffers containing Chromium(III) PPIX (Protoporphyrin IX) at concentrations of 1.25-5 μM at an adjusted pH range of 6.2-7.4 provide increased Hb stability in the 35 C 16 hour challenge.

| 35C 16 hour challenge | | | | | |
|---|---|---|---|---|---|
| Compound Class. | Additive | Additive Conc. | Buffer PH | % Recovery | Notes |
| Hb Collection Buffer | NA | NA | 7.4 | 71.2 | Current Formulation |

-continued

| Compound Class. | Additive | Additive Conc. | Buffer PH | % Recovery | Notes |
|---|---|---|---|---|---|
| | | 35C 16 hour challenge | | | |
| Protoporphyrin | Protoporphyrin IX Co | 2.5 µM | 6.2 | 76.0 | Improved Hb Stability |
| | | 2.5 µM | 6.5 | 84.1 | Improved Hb Stability |
| | | 2.5 µM | 6.8 | 82.3 | Improved Hb Stability |
| | | 2.5 µM | 7.1 | 80.4 | Improved Hb Stability |
| | | 5.0 µM | 6.2 | 104.3 | Improved Hb Stability |
| | | 5.0 µM | 6.5 | 105.5 | Improved Hb Stability |
| | | 5.0 µM | 6.8 | 93.8 | Improved Hb Stability |
| | | 5.0 µM | 7.1 | 85.1 | Improved Hb Stability |
| | | 5.0 µM | 7.4 | 78.4 | Improved Hb Stability |
| | | 10 µM | 6.2 | 116.0 | Improved Hb Stability |
| | | 10 µM | 6.8 | 107.6 | Improved Hb Stability |
| | | 10 µM | 7.1 | 112.9 | Improved Hb Stability |
| | | 10 µM | 7.4 | 98.5 | Improved Hb Stability |
| Protoporphyrin | Protoporphyrin IX Cr | 1.25 µM | 6.2 | 74.0 | Improved Hb Stability |
| | | 1.25 µM | 6.5 | 77.0 | Improved Hb Stability |
| | | 1.25 µM | 6.8 | 105.0 | Improved Hb Stability |
| | | 1.25 µM | 7.1 | 77.5 | Improved Hb Stability |
| | | 1.25 µM | 7.4 | 73.5 | Improved Hb Stability |
| | | 2.5 µM | 6.2 | 79.8 | Improved Hb Stability |
| | | 2.5 µM | 6.5 | 86.3 | Improved Hb Stability |
| | | 2.5 µM | 6.8 | 85.0 | Improved Hb Stability |
| | | 2.5 µM | 7.1 | 81.8 | Improved Hb Stability |
| | | 2.5 µM | 7.4 | 73.1 | Improved Hb Stability |
| | | 5 µM | 6.2 | 87.5 | Improved Hb Stability |
| | | 5 µM | 6.5 | 89.6 | Improved Hb Stability |
| | | 5 µM | 7.1 | 86.0 | Improved Hb Stability |
| | | 5 µM | 7.4 | 75.5 | Improved Hb Stability |

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

APPENDIX A

| Compound Classification | Compound |
|---|---|
| Metal Chelators | Nitrilotriacetic acid (NTA) |
| | Ethylenediamine-N,N'-disuccinic acid (EDDS) |
| | diethylenetriaminepentaacetic acid (DTPA) |
| | Iminodisuccinic acid (IDS; ISA) |
| | N,N-bis-(Carboxymethyl)-L-glutamic acid tetrasodiumn salt (GLDA) |
| | Trisodium N-(1-Carboxylatoethyl)iminodiacetate Hydrate (MGDA) |
| | Phytic Acid (IP6) |
| | ATMP - Amino tris (methylene phosphonic acid) |
| | Iminodiacetic Acid (IDA) |
| | sodium tripolyphosphate |
| | ethylenediamine-N,N,N',N'-4-acetic acid (EDTA) |
| Flavoniods | quercetin |
| | chrysin-pyridine |
| | daidzein - DMSO |
| | 7,8-Dihydroxyflavone |
| Protease/ Phosphatase Inhibitors | aurintircarboxylic acid ammonium salt |
| | methylisothiazolone |
| | Proclin 300 |
| | sodium fluoride |
| Crosslinkers | poly(acrylic acid) |
| | 4arm-PEG20K-Maleimide |
| | mPEG-Maleimide, 5K |
| | glutaraldehyde |
| | Dimethyl 3,3'-dithiopropionimidate dihydrochloride |
| | bis(3,5-dibromosalicyl) fumarate |
| | formaldehyde solution |
| | magnesium gluconate |
| | cysteamine |
| | methylglyoxal |
| Similar to Drabkin's Reagent (cyanide) | Imidazole |
| | hydroxylamine |
| | Histidine |
| Non-covalent Hb interactions | polysufonated polymers (dextran sulphate) |
| | heparin |
| | PEG 2000 |
| | PEG 20000 |
| | PEG 8000 |
| | Bovine Serum Albumin |
| | Poly viny alcohol |
| Sulfonic Acids | methanedisulfonic acid dipotassium salt |
| | propanedisulfonic acid disodium sat |
| | piperazine-N-N'-bis (2-ethanesulfonic acid) (PIPES) |
| Preservatives with thiol groups | Sodium Thiosulfate |
| | Cysteine |
| | glutathione |
| | dithiothreitol |
| | TCEP |
| Sugars/Saccharides | trehalose |
| | Glucose |
| | raffinose |
| | corn starch |
| | potato starch |
| | Gum arabic |
| | xanthan gum |
| | Lactose |
| | Maltose |
| | Fructose |
| | Galactose |
| | Isomaltotriose |
| | Maltotriose |
| | Melezitose |
| | Kestose |
| | Stachyose |
| | Glucose Tetrasaccharide |
| | Erlose |
| | Mannose |
| | Polygalacturonic Acid |
| | Galacturonic Acid (monomer) |
| | Sodium Alginate (synthetic) |
| | Sodium Alginate (Medium Viscosity) |
| | Sodium Alginate (Low Viscosity) |

APPENDIX A

| Compound Classification | Compound |
|---|---|
| Redox/antioxidants | lipoic acid |
| | mPEG2K-Thioctic acid |
| | ascorbic acid |
| | glutathione |
| | Deferoxamine mesylate salt |
| | uric acid |
| | urea |
| Formaldehyde Releasers | Imidazolidinyl Urea |
| | Bronopol |
| | Diazolidinyl Urea |
| | DMDM Hydantoin |
| | Sodium hydroxymethyl glycinate |
| | Tris(Hydroxymethyl)nitromethane |
| | 5-bromo-5-nitro-1,3-dioxane |
| | 2-bromo-2-nitro-1,3-propanediol |
| | 1,3-Bis(hydroxymethyl)-5,5-dimethylimidazolidine-2,4-dione |
| | Streck Cell Preservative Solution |
| | 1-(cis-3-Chloroallyl)-3,5,7-triaza-1-azoniaadamantane chloride |
| Substrates | Styrene Glycol |
| | Styrene Oxide |
| | Sodium Bicarbonate |
| | DPG, diphospho glycerate |
| | Arginine |
| | Lysine |
| | Resveratrol |
| Protoporphyrins | Protoporphyrin IX Zn |
| | Protoporphyrin IX |
| | Protoporphyrin IX Cobalt |
| | Protoporphyrin IX Chromium |
| | Protoporphyrin IX Magnesium |
| | Protoporphyrin IX Manganese |
| | Protoporphyrin IX Tin |
| | Protoporphyrin IX Gallium |
| | Hemin, Bovine |
| | Hematin |
| | Bilirubin |
| | Biliverdin |
| Osmolytes/Extremolytes | Betaine |
| | Trimethylamine N-oxide |
| | Ectoine |
| | Firoin |
| Formaldehyde + Ammonium Salt Complexes | paraformaldehyde |
| | formaldehyde solution |
| | ammonium chloride |
| | ammonium sulfate |
| | ammonium acetate |
| | ammonium oxalate |
| | hexamethylenetetramine |
| Ionic Liquids | 1-Allyl-3-methylimidazolium chloride |
| | 1-Butyl-3-methylimidazolium chloride |
| | 1-butyl-2,3-dimethylimidazolium tetrafluoroborate |
| | 1-butyl-3-methylimidazoliumtetrafluoroborate |
| | 1-Ethyl-3-methylimidazolium chloride |
| | 2-(Diethylamino)ethanol |
| | Methyl hexanoate |
| | 1-hexyl-3-methylimidazolium chloride |
| | 1-decyl-3-methylimidazolium chloride |
| | Sodium Bromide |
| Deep Eutectic Solvents | Choline Chloride |
| | Tetrabutylammonium bromide |
| | urea |
| | Imidazole |
| | Glycerol |
| | Ethylene Glycol |
| | D-glucose |
| Polyvalent Ions/ Metal Salts | Fe (III) Chloride |
| | Cobalt |
| | Nickel |
| | Copper |
| | Zinc |
| | Sodium Bisulfite |
| | Sodium Carbonate |
| | Sodium Perchlorate |
| | Sodium Phosphate |

APPENDIX A

| Compound Classification | Compound |
|---|---|
| | Sodium Acetate |
| | Potassium Chloride |
| | Magnesium Chloride |
| | Potassium Acetate |
| | Lithium Chloride |
| | Iron (II) Sulfate |
| | Magnesium Sulfate |
| | Zinc chloride |
| | Calcium Chloride |
| | Calcium Gluconate |
| | Calcium Propoinate |
| HRP Stabilizer Components | Calcium Propoinate |
| | 8-anilino-1-napthalene sulfonic acid ammonium salt |
| | aluminum chloride hexahydrate |
| | 4-bromophenol |
| | 2-methyl-4-isothiazolin-3-one-hydrochloride |
| | 5-bromo-5-nitro-1,3-dioxane |
| | AAT Bioquest HRP Stabilization Buffer |
| | Azobenzene |
| | Phenol Red |
| | Proclin 300 |
| | Candor HRP Stabilization Buffer |
| | Innova HRP Stabilization Buffer |
| | Surmodics HRP Stabilization Buffer |
| | BioRad HRP Stabilization Buffer |
| | Sigma HRP Stabilization Buffer |
| | Guardian Peroxidase Conjugate Buffer |
| | Fitzgerald HRP Conjugate Buffer |
| | Sigma HRP Stabilization Buffer |
| Vitamins | Pyridoxal 5'-phosphate hydrate (B6) |
| | NAD |
| | Vitamin B12 |
| | NADH |
| | Nicotinic Acid (B3) |
| | Folic Acid (M) |
| | Nicotinamide (B3) |
| | Vitamin E (alpha tocopherol) |
| Preservatives | Sodium Nitrate |
| | Sodium Nitrite |
| | Sodium Citrate |
| | Sodium Benzoate |
| Preservatives/Parabens | Ethyl 4-hydroxybenzoate |
| | Methyl 4-hydroxybenzoate |
| | Propyl 4-hydroxybenzoate |
| | Benzyl 4-hydroxybenzoate |
| Aldehydes | formaldehyde solution |
| | paraformaldehyde |
| | Glutaraldehyde |
| | Furfural |
| | p-Tolualdehyde |
| | Cinnamaldehyde |
| | Butyraldehyde |
| | Glycolaldehyde Dimer |
| | Glyceraldehyde |
| | Formamide |
| | 4-Isobutylbenzaldehyde |
| | Benzaldehyde |
| | Acetylaldehyde |
| | Vanillin |
| Plasma | Human Plasma |
| | Albumin |
| | Glycine |
| | HDL |
| | LDL |
| | Phosphatidylcholine |
| | Cohns Fraction II/III |
| | Cohns Fraction IV |
| | Fetal Bovine Serum |
| | Bovine Plasma |
| | Gamma Globulins |

APPENDIX A

| Compound Classification | Compound |
|---|---|
| Gelatins | Gelatin - Bovine Type B (225 g bloom) |
| | Gelatin - Porcine Type A (90-110 g bloom) |
| | Gelatin - Porcine Type A (175 g bloom) |
| | Gelatin - Porcine Type A (300 g bloom) |
| | Gelatin - Cold Water Fish Skin |
| Detergents | Brij 35 |
| | Tween 20 |
| | Triton X-100 |
| Solvents | 1N HCl |
| | 1M NaOH |
| | 1M Tris, pH 7.5 |
| | pyridine |
| | DMSO |

APPENDIX B

| Compound aassification | Additive | Additive Concentration | % Hb Recovery | Results |
|---|---|---|---|---|
| None | Hb Collection Buffer - No additive | NA | 68 | Current Buffer Formulation |
| None | Polymedco Buffer - No additive | NA | 80 | |
| Ionic Liquids | 1-ethyl-3-methylimidazolium chloride | 1 mM | 68 | No Improvement |
| Ionic Liquids | 1-ethyl-3-methylimidazolium chloride | 10 mM | 69 | No Improvement |
| Ionic Liquids | 1-ethyl-3-methylimidazolium chloride | 100 mM | 65 | No Improvement |
| Ionic Liquids | 1-hexyl-3-methylimidazolium chloride | 0.02% | 67 | No Improvement |
| Ionic Liquids | 1-hexyl-3-methylimidazolium chloride | 0.20% | 61 | No Improvement |
| Ionic Liquids | 1-hexyl-3-methylimidazolium chloride | 1% | 42 | No Improvement |
| Protoporphyrin | Protoprophyrin IX | 0.001 mM | 65 | No Improvement |
| Protoporphyrin | Protoprophyrin IX | 0.01 mM | 62 | No Improvement |
| Protoporphyrin | Protoprophyrin IX | 0.1 mM | 63 | No Improvement |
| Protoporphyrin | Protoprophyrin IX Zn | 0.001 mM | 68 | No Improvement |
| Protoporphyrin | Protoprophyrin IX Zn | 0.01 mM | 59 | No Improvement |
| Protoporphyrin | Protoprophyrin IX Zn | 0.1 mM | 53 | No Improvement |
| Formaldehyde Releaser | Sodium hydroxylmethyl glycinate | 0.1 mM | 70 | No Improvement |
| Formaldehyde Releaser | Sodium hydroxylmethyl glycinate | 1 mM | 64 | No Improvement |
| Formaldehyde Releaser | Sodium hydroxylmethyl glycinate | 10 mM | 66 | No Improvement |
| Osmolytes | Trimethylamine N-oxide (TMANO) | 50 mM | 76 | No Improvement |
| Osmolytes | Trimethylamine N-oxide (TMANO) | 100 mM | 72 | No Improvement |
| Osmolytes | Trimethylamine N-oxide (TMANO) | 200 mM | 74 | No Improvement |
| Protoporphyrin | Protoprophyrin IX + FeCl3 | 0.1 mM + 0.1 mM | 62 | No Improvement |
| Protoporphyrin | Protoprophyrin IX + FeCl3 | 1 mM + 1 mM | 53 | No Improvement |
| Protoporphyrin | Protoprophyrin IX + FeCl3 | 10 mM + 10 mM | 40 | No Improvement |
| Crosslinkers | Poly Acrylic Acid | 1 mM | 64 | No Improvement |
| Crosslinkers | Poly Acrylic Acid | 5 mM | 56 | No Improvement |
| Crosslinkers | Poly Acrylic Acid | 7 mM | 58 | No Improvement |
| Crosslinkers | 4arm-PEG2K-Maleimide + Iminothiolane hydrochloride | 0.062 mM + 1 mM | 67 | No Improvement |
| Crosslinkers | 4arm-PEG2K-Maleimide + Iminothiolane hydrochloride | 0.125 mM + 2 mM | 66 | No Improvement |
| Crosslinkers | 4arm-PEG2K-Maleimide + Iminothiolane hydrochloride | 2.5 mM + 10 mM | 27 | No Improvement |
| Crosslinkers | mPEG-Mal, 5K + Iminothiolane hydrochloride | 0.5 mM + 1 mM | 65 | No Improvement |
| Crosslinkers | mPEG-Mal, 5K + Iminothiolane hydrochloride | 1 mM + 2 mM | 58 | No Improvement |
| Crosslinkers | mPEG-Mal, 5K + Iminothiolane hydrochloride | 5 mM + 10 mM | 56 | No Improvement |
| Plasma | Human Plasma, lyopholyzed | 1% | 97 | High Background Signal |
| Plasma | Human Plasma, lyopholyzed | 5% | 98 | High Background Signal |
| Plasma | Human Plasma, lyopholyzed | 10% | 97 | High Background Signal |
| Plasma | Human Plasma, lyopholyzed | 25% | 94 | High Background Signal |
| Plasma | Human Plasma, lyopholyzed | 50% | 95 | High Background Signal |
| Plasma | Human Plasma, lyopholyzed | 1% | 96 | High Background Signal |
| Plasma | Human Plasma, lyopholyzed | 5% | 97 | High Background Signal |
| Plasma | Human Plasma, lyopholyzed | 10% | 96 | High Background Signal |
| Plasma | Human Plasma, lyopholyzed | 25% | 98 | High Background Signal |
| Plasma | Human Plasma, lyopholyzed | 50% | 99 | High Background Signal |
| Plasma | Human Plasma, lyopholyzed | 1% | 97 | High Background Signal |
| Plasma | Human Plasma, lyopholyzed | 0.50% | 92 | High Background Signal |
| Plasma | Human Plasma, lyopholyzed | 0.10% | 99 | High Background Signal |

APPENDIX B

| Compound aassification | Additive | Additive Concentration | % Hb Recovery | Results |
|---|---|---|---|---|
| Plasma | Human Plasma, lyopholyzed | 0.05% | 101 | High Background Signal |
| Plasma | Human Plasma, lyopholyzed | 0.01% | 81 | High Background Signal |
| Plasma | Human Plasma, lyopholyzed | 0.005% | 81 | High Background Signal |
| Plasma | Human Plasma, lyopholyzed | 0.001% | 71 | High Background Signal |
| Plasma | Human Plasma, lyopholyzed | 0.005% | 77 | High Background Signal |
| Plasma | Human Plasma, lyopholyzed | 0.01% | 80 | High Background Signal |
| Plasma | Human Plasma, lyopholyzed | 0.02% | 88 | High Background Signal |
| Plasma | Human Plasma, lyopholyzed | 0.03% | 93 | High Background Signal |
| Plasma | Human Plasma, lyopholyzed | 0.04% | 97 | High Background Signal |
| Plasma | Human Plasma, lyopholyzed | 0.05% | 95 | High Background Signal |
| Plasma | Human Plasma, lyopholyzed | 0.10% | 99 | High Background Signal |
| Plasma | Albumin, Human | 0.0025 mg/mL | 71 | No Improvement |
| Plasma | Albumin, Human | 0.025 mg/mL | 90 | No Improvement |
| Plasma | Albumin, Human | 0.25 mg/mL | 98 | No Improvement |
| Plasma | Albumin, Human | 2.5 mg/mL | 99 | No Improvement |
| Plasma | Albumin, Human | 25 mg/mL | 98 | No Improvement |
| Plasma | Glycine | 0.0002 mg/mL | 68 | No Improvement |
| Plasma | Glycine | 0.002 mg/mL | 68 | No Improvement |
| Plasma | Glycine | 0.02 mg/mL | 71 | No Improvement |
| Plasma | Cohn's Fraction II/III | 0.005 mg/mL | 70 | High Background Signal |
| Plasma | Cohn's Fraction II/III | 0.05 mg/mL | 80 | High Background Signal |
| Plasma | Cohn's Fraction II/III | 0.5 mg/mL | 99 | High Background Signal |
| Plasma | Cohn's Fraction II/III | 5 mg/mL | 100 | High Background Signal |
| Plasma | Cohn's Fraction II/III | 50 mg/mL | 97 | High Background Signal |
| Plasma | Cohn's Fraction IV | 0.005 mg/mL | 106 | High Background Signal |
| Plasma | Cohn's Fraction IV | 0.05 mg/mL | 100 | High Background Signal |
| Plasma | Cohn's Fraction IV | 0.5 mg/mL | 98 | High Background Signal |
| Plasma | Cohn's Fraction IV | 5 mg/mL | 96 | High Background Signal |
| Plasma | Cohn's Fraction IV | 50 mg/mL | 98 | High Background Signal |
| Plasma | HDL | 0.0025 mg/mL | 69 | No Improvement |
| Plasma | HDL | 0.025 mg/mL | 69 | No Improvement |
| Plasma | HDL | 0.25 mg/mL | 70 | No Improvement |
| Plasma | LDL | 0.0025 mg/mL | 69 | No Improvement |
| Plasma | LDL | 0.025 mg/mL | 70 | No Improvement |
| Plasma | LDL | 0.25 mg/mL | 67 | No Improvement |
| Plasma | phosphatidylcholine | 0.01 mg/mL | 67 | No Improvement |
| Plasma | phosphatidylcholine | 0.1 mg/mL | 66 | No Improvement |
| Plasma | phosphatidylcholine | 1 mg/mL | 62 | No Improvement |
| Polyvalent Ions/Metal Salts | Calcium Chloride | 1 mM | 74 | Calcium cation shows improvement in % Hb Recovery at 10 mM |
| Polyvalent Ions/Metal Salts | Calcium Chloride | 10 mM | 78 | Calcium cation shows improvement in % Hb Recovery at 10 mM |
| Polyvalent Ions/Metal Salts | Calcium Chloride | 100 mM | 119 | Calcium cation shows improvement in % Hb Recovery at 10 mM |
| Deep Eutectic Solvents | Ethylene Glycol | 5% | 69 | No Improvement |
| Deep Eutectic Solvents | Ethylene Glycol | 10% | 63 | No Improvement |
| Deep Eutectic Solvents | Ethylene Glycol | 20% | 54 | No Improvement |
| Polyvalent Ions/Metal Salts | Ethylene Glycol + Calcium Chloride | 10% + 10 mM | 70 | No Improvement |
| Polyvalent Ions/Metal Salts | Ethylene Glycol + Calcium Chloride | 2.5% + 2.5 mM | 70 | No Improvement |
| Polyvalent Ions/Metal Salts | Ethylene Glycol + Calcium Chloride | 5% + 5 mM | 72 | No Improvement |
| Non-covalent Hb interactions | Dextran Sulphate | 3.75% | 67 | No Improvement |
| Non-covalent Hb interactions | Dextran Sulphate | 7.50% | 63 | No Improvement |
| Non-covalent Hb interactions | Dextran Sulphate | 15% | 70 | No Improvement |
| Osmolytes | Betaine | 125 mM | 72 | Betaine shows improvement in % Hb Recovery at high concentrations |
| Osmolytes | Betaine | 250 mM | 76 | Betaine shows improvement in % Hb Recovery at high concentrations |
| Osmolytes | Betaine | 500 mM | 78 | Betaine shows improvement in % Hb Recovery at high concentrations |
| Sugars/Saccharides | Trehalose + Betaine | 125 mM + 62.5 mM | 77 | Slight Improvement with Sugars. Needs further assay optimization |
| Sugars/Saccharides | Trehalose + Betaine | 250 mM + 125 mM | 78 | Slight Improvement with Sugars. Needs further assay optimization |
| Sugars/Saccharides | Trehalose + Betaine | 500 mM + 250 mM | 79 | Slight Improvement with Sugars. Needs further assay optimization |

APPENDIX B

| Compound aassification | Additive | Additive Concentration | % Hb Recovery | Results |
|---|---|---|---|---|
| Sugars/Saccharides | Glucose + Betaine | 250 mM + 62.5 mM | 72 | Slight Improvement with Sugars. Needs further assay optimization |
| Sugars/Saccharides | Glucose + Betaine | 500 mM + 125 mM | 76 | Slight Improvement with Sugars. Needs further assay optimization |
| Sugars/Saccharides | Glucose + Betaine | 1M + 250 mM | 78 | Slight Improvement with Sugars. Needs further assay optimization |
| Sugars/Saccharides | Glucose + Glycerol | 250 mM + 2.5% | 73 | Slight Improvement with Sugars. Needs further assay optimization |
| Sugars/Saccharides | Glucose + Glycerol | 500 mM + 5% | 71 | Slight Improvement with Sugars. Needs further assay optimization |
| Sugars/Saccharides | Glucose + Glycerol | 1M + 10% | 73 | Slight Improvement with Sugars. Needs further assay optimization |
| Sugars/Saccharides | Glucose + Glycine | 250 mM + 62.5 mM | 72 | Slight Improvement with Sugars. Needs further assay optimization |
| Sugars/Saccharides | Glucose + Glycine | 500 mM + 125 mM | 78 | Slight Improvement with Sugars. Needs further assay optimization |
| Sugars/Saccharides | Glucose + Glycine | 1M + 250 mM | 77 | Slight Improvement with Sugars. Needs further assay optimization |
| Sugars/Saccharides | Trehalose + Glycerol | 125 mM + 2.5% | 71 | Slight Improvement with Sugars. Needs further assay optimization |
| Sugars/Saccharides | Trehalose + Glycerol | 250 mM + 5% | 72 | Slight Improvement with Sugars. Needs further assay optimization |
| Sugars/Saccharides | Trehalose + Glycine | 125 mM + 62.5 mM | 70 | Slight Improvement with Sugars. Needs further assay optimization |
| Sugars/Saccharides | Trehalose + Glycine | 250 mM + 125 mM | 72 | Slight Improvement with Sugars. Needs further assay optimization |
| Sugars/Saccharides | Trehalose + Glycine | 500 mM + 250 mM | 79 | Slight Improvement with Sugars. Needs further assay optimization |
| Sugars/Saccharides | Trehalose | 1M | 77 | Slight Improvement with Sugars. Needs further assay optimization |
| Polyvalent Ions/Metal Salts | Calcium Chloride | 5 mM | 74 | Calcium cation shows improvement in % Hb Recovery at 10 mM |
| Polyvalent Ions/Metal Salts | Calcium Chloride | 10 mM | 67 | Calcium cation shows improvement in % Hb Recovery at 10 mM |
| Polyvalent Ions/Metal Salts | Calcium Chloride | 25 mM | 75 | Calcium cation shows improvement in % Hb Recovery at 10 mM |
| Polyvalent Ions/Metal Salts | Calcium Chloride | 50 mM | 68 | Calcium cation shows improvement in % Hb Recovery at 10 mM |
| Polyvalent Ions/Metal Salts | Calcium Chloride | 100 mM | 51 | Calcium cation shows improvement in % Hb Recovery at 10 mM |
| Polyvalent Ions/Metal Salts | Calcium Chloride + PEG 2000 | 0.075% + 1% | 74 | Calcium cation shows improvement in % Hb Recovery at 10 mM |
| Polyvalent Ions/Metal Salts | Calcium Chloride + PEG 2000 | 0.15% + 2% | 71 | Calcium cation shows improvement in % Hb Recovery at 10 mM |
| Polyvalent Ions/Metal Salts | Calcium Chloride + PEG 2000 | 0.3% + 4% | 62 | Calcium cation shows improvement in % Hb Recovery at 10 mM |
| Polyvalent Ions/Metal Salts | Calcium Chloride + PEG 20000 | 0.075% + 1% | 74 | Calcium cation shows improvement in % Hb Recovery at 10 mM |

-continued

APPENDIX B

| Compound aassification | Additive | Additive Concentration | % Hb Recovery | Results |
|---|---|---|---|---|
| Polyvalent Ions/Metal Salts | Calcium Chloride + PEG 20000 | 0.15% + 2% | 72 | Calcium cation shows improvementin % Hb Recovery at 10 mM |
| Polyvalent Ions/Metal Salts | Calcium Chloride + PEG 20000 | 0.3% + 4% | 66 | Calcium cation shows improvement in % Hb Recovery at 10 mM |
| Polyvalent Ions/Metal Salts | Calcium Chloride + PEG 8000 | 0.075% + 1% | 75 | Calcium cation shows improvement in % Hb Recovery at 10 mM |
| Polyvalent Ions/Metal Salts | Calcium Chloride + PEG 8000 | 0.15% + 2% | 75 | Calcium cation shows improvement in % Hb Recovery at 10 mM |
| Polyvalent Ions/Metal Salts | Calcium Chloride + PEG 8000 | 0.3% + 4% | 67 | Calcium cation shows improvement in % Hb Recovery at 10 mM |
| Formaldehyde + Ammonium Salt Complexes | Ammonium Acetate | 100 mM | 58 | No Improvement |
| Formaldehyde + Ammonium Salt Complexes | Ammonium Acetate | 25 mM | 58 | No Improvement |
| Formaldehyde + Ammonium Salt Complexes | Ammonium Acetate | 50 mM | 59 | No Improvement |
| Formaldehyde + Ammonium Salt Complexes | Ammonium Chloride | 100 mM | 58 | No Improvement |
| Formaldehyde + Ammonium Salt Complexes | Ammonium Chloride | 25 mM | 104 | No Improvement |
| Formaldehyde + Ammonium Salt Complexes | Ammonium Chloride | 50 mM | 58 | No Improvement |
| Formaldehyde + Ammonium Salt Complexes | Ammonium Oxalate | 10 mM | 62 | No Improvement |
| Formaldehyde + Ammonium Salt Complexes | Ammonium Oxalate | 2.5 mM | 60 | No Improvement |
| Formaldehyde + Ammonium Salt Complexes | Ammonium Oxalate | 5 mM | 59 | No Improvement |
| Formaldehyde + Ammonium Salt Complexes | Ammonium Sulfate | 100 mM | 61 | No Improvement |
| Formaldehyde + Ammonium Salt Complexes | Ammonium Sulfate | 25 mM | 60 | No Improvement |
| Formaldehyde + Ammonium Salt Complexes | Ammonium Sulfate | 50 mM | 58 | No Improvement |
| Polyvalent Ions/Metal Salts | Calcium Gluconate | 100 mM | 57 | No Improvement |
| Polyvalent Ions/Metal Salts | Calcium Gluconate | 25 mM | 66 | No Improvement |
| Polyvalent Ions/Metal Salts | Calcium Gluconate | 50 mM | 65 | No Improvement |
| Sugars/Saccharides | Glucose + Calcium Chloride | 0.5M + 0.5% | 65 | No Improvement |
| Sugars/Saccharides | Glucose + Calcium Chloride | 1M + 1% | 65 | No Improvement |
| Sugars/Saccharides | Glucose + Calcium Chloride | 2M + 2% | 61 | No Improvement |
| Polyvalent Ions/Metal Salts | Magnesium Gluconate | 100 mM | 58 | No Improvement |
| Polyvalent Ions/Metal Salts | Magnesium Gluconate | 25 mM | 69 | No Improvement |
| Polyvalent Ions/Metal Salts | Magnesium Gluconate | 50 mM | 65 | No Improvement |
| Polyvalent Ions/Metal Salts | Calcium Chloride (anhydrous) | 0.1 mM | 73 | Calcium cation shows improvement in % Hb Recovery at 10 mM |
| Polyvalent Ions/Metal Salts | Calcium Chloride (anhydrous) | 1 mM | 71 | Calcium cation shows improvement in % Hb Recovery at 10 mM |
| Polyvalent Ions/Metal Salts | Calcium Chloride (anhydrous) | 2 mM | 72 | Calcium cation shows improvement in % Hb Recovery at 10 mM |
| Polyvalent Ions/Metal Salts | Calcium Chloride (anhydrous) | 4 mM | 73 | Calcium cation shows improvement in % Hb Recovery at 10 mM |
| Polyvalent Ions/Metal Salts | Calcium Chloride (anhydrous) | 6 mM | 77 | Calcium cation shows improvement in % Hb Recovery at 10 mM |
| Polyvalent Ions/Metal Salts | Calcium Chloride (anhydrous) | 8 mM | 75 | Calcium cation shows improvement in % Hb Recovery at 10 mM |
| Polyvalent Ions/Metal Salts | Calcium Chloride (anhydrous) | 10 mM | 79 | Calcium cation shows improvement in % Hb Recovery at 10 mM |
| Polyvalent Ions/Metal Salts | Calcium Chloride (anhydrous) | 20 mM | 76 | Calcium cation shows improvement in % Hb Recovery at 10 mM |

-continued

APPENDIX B

| Compound aassification | Additive | Additive Concentration | % Hb Recovery | Results |
|---|---|---|---|---|
| Polyvalent Ions/Metal Salts | Calcium Chloride (dihydrate) | 0.1 mM | 71 | Calcium cation shows improvement in % Hb Recovery at 10 mM |
| Polyvalent Ions/Metal Salts | Calcium Chloride (dihydrate) | 1 mM | 70 | Calcium cation shows improvement in % Hb Recovery at 10 mM |
| Polyvalent Ions/Metal Salts | Calcium Chloride (dihydrate) | 2 mM | 71 | Calcium cation shows improvement in % Hb Recovery at 10 mM |
| Polyvalent Ions/Metal Salts | Calcium Chloride (dihydrate) | 4 mM | 74 | Calcium cation shows improvement in % Hb Recovery at 10 mM |
| Polyvalent Ions/Metal Salts | Calcium Chloride (dihydrate) | 6 mM | 74 | Calcium cation shows improvemen in % Hb Recovery at 10 mM |
| Polyvalent Ions/Metal Salts | Calcium Chloride (dihydrate) | 8 mM | 72 | Calcium cation shows improvement in % Hb Recovery at 10 mM |
| Polyvalent Ions/Metal Salts | Calcium Chloride (dihydrate) | 10 mM | 77 | Calcium cation shows improvement in % Hb Recovery at 10 mM |
| Polyvalent Ions/Metal Salts | Calcium Chloride (dihydrate) | 20 mM | 73 | Calcium cation shows improvement in % Hb Recovery at 10 mM |
| Formaldehyde Releaser | 5-bromo-5-nitro-1,3-dioxane | 0.0002% | 69 | No Improvement |
| Formaldehyde Releaser | 5-bromo-5-nitro-1,3-dioxane | 0.001% | 68 | No Improvement |
| Formaldehyde Releaser | 5-bromo-5-nitro-1,3-dioxane | 0.002% | 70 | No Improvement |
| Enzyme Inhibitor | 2-methyl-4-isothiazolin-3-one-hydrochloride | 0.0002% | 71 | No Improvement |
| Enzyme Inhibitor | 2-methyl-4-isothiazolin-3-one-hydrochloride | 0.001% | 68 | No Improvement |
| Enzyme Inhibitor | 2-methyl-4-isothiazolin-3-one-hydrochloride | 0.002% | 63 | No Improvement |
| HRP Stabilizer Components | Phenol Red | 0.01% | 70 | No Improvement |
| HRP Stabilizer Components | Phenol Red | 0.03% | 71 | No Improvement |
| HRP Stabilizer Components | Phenol Red | 0.05% | 70 | No Improvement |
| Preservatives | Sodium Benzoate | 0.10% | 67 | No Improvement |
| Preservatives | Sodium Benzoate | 0.50% | 60 | No Improvement |
| Preservatives | Sodium Benzoate | 1% | 54 | No Improvement |
| HRP Stabilizer Components | Sigma HRP Stabilization Buffer | 5% | 71 | No Improvement |
| HRP Stabilizer Components | Sigma HRP Stabilization Buffer | 10% | 70 | No Improvement |
| HRP Stabilizer Components | Sigma HRP Stabilization Buffer | 25% | 68 | No Improvement |
| HRP Stabilizer Components | HRP Conjugate Stabilizer (PN SZ02) | 5% Additive | 83 | Improvement in % Hb Recovery |
| HRP Stabilizer Components | HRP Conjugate Stabilizer (PN SZ02) | 5% Component | 71 | Improvement in % Hb Recovery |
| Polyvalent Ions/Metal Salts | Calcium Gluconate | 100 mM | 57 | No Improvement |
| Polyvalent Ions/Metal Salts | Calcium Gluconate | 25 mM | 66 | No Improvement |
| Polyvalent Ions/Metal Salts | Calcium Gluconate | 50 mM | 65 | No Improvement |
| Sugars/Saccharides | Glucose + Calcium Chloride | 0.5M + 0.5% | 65 | Slight Improvement with Sugars. Needs further assay optimization |
| Sugars/Saccharides | Glucose + Calcium Chloride | 1M + 1% | 65 | Slight Improvement with Sugars. Needs further assay optimization |
| Sugars/Saccharides | Glucose + Calcium Chloride | 2M + 2% | 61 | Slight Improvement with Sugars. Needs further assay optimization |
| Polyvalent Ions/Metal Salts | Magnesium Gluconate | 100 mM | 58 | No Improvement |
| Polyvalent Ions/Metal Salts | Magnesium Gluconate | 25 mM | 69 | No Improvement |
| Polyvalent Ions/Metal Salts | Magnesium Gluconate | 50 mM | 65 | No Improvement |
| Polyvalent Ions/Metal Salts | Iron (2) Chloride | 36 mM | 60 | No Improvement |
| Polyvalent Ions/Metal Salts | Iron (2) Chloride | 43.2 mM | 51 | No Improvement |
| Polyvalent Ions/Metal Salts | Iron (2) Chloride | 48 mM | 27 | No Improvement |
| Polyvalent Ions/Metal Salts | Lithium Chloride | 100 mM | 68 | No Improvement |
| Polyvalent Ions/Metal Salts | Lithium Chloride | 150 mM | 66 | No Improvement |
| Polyvalent Ions/Metal Salts | Lithium Chloride | 260 mM | 66 | No Improvement |
| Polyvalent Ions/Metal Salts | Magnesium Chloride | 100 mM | 62 | Magnesium Cation shows improvement in % Hb Recovery around 10 mM |
| Polyvalent Ions/Metal Salts | Magnesium Chloride | 150 mM | 61 | Magnesium Cation shows improvement in % Hb Recovery around 10 mM |
| Polyvalent Ions/Metal Salts | Magnesium Chloride | 192 mM | 57 | Magnesium Cation shows improvement in % Hb Recovery around 10 mM |

APPENDIX B

| Compound aassification | Additive | Additive Concentration | % Hb Recovery | Results |
|---|---|---|---|---|
| Polyvalent Ions/Metal Salts | Potassium Acetate | 100 mM | 65 | No Improvement |
| Polyvalent Ions/Metal Salts | Potassium Acetate | 150 mM | 69 | No Improvement |
| Polyvalent Ions/Metal Salts | Potassium Acetate | 260 mM | 67 | No Improvement |
| Polyvalent Ions/Metal Salts | Potassium Chloride | 100 mM | 53 | No Improvement |
| Polyvalent Ions/Metal Salts | Potassium Chloride | 150 mM | 63 | No Improvement |
| Polyvalent Ions/Metal Salts | Potassium Chloride | 260 mM | 66 | No Improvement |
| Polyvalent Ions/Metal Salts | Sodium Acetate | 100 mM | 55 | No Improvement |
| Polyvalent Ions/Metal Salts | Sodium Acetate | 150 mM | 40 | No Improvement |
| Polyvalent Ions/Metal Salts | Sodium Acetate | 260 mM | 45 | No Improvement |
| Substrates | Sodium Bicarbonate | 100 mM | 46 | No Improvement |
| Substrates | Sodium Bicarbonate | 150 mM | 43 | No Improvement |
| Substrates | Sodium Bicarbonate | 260 mM | 42 | No Improvement |
| Polyvalent Ions/Metal Salts | Sodium Bisulfite | 101.055 mM | 38 | No Improvement |
| Polyvalent Ions/Metal Salts | Sodium Bisulfite | 75.791 mM | 46 | No Improvement |
| Polyvalent Ions/Metal Salts | Sodium Bisulfite | 90.95 mM | 41 | No Improvement |
| Polyvalent Ions/Metal Salts | Sodium Bromide | 100 mM | 65 | No Improvement |
| Polyvalent Ions/Metal Salts | Sodium Bromide | 150 mM | 64 | No Improvement |
| Polyvalent Ions/Metal Salts | Sodium Bromide | 192 mM | 59 | No Improvement |
| Polyvalent Ions/Metal Salts | Sodium Carbonate | 38.207 mM | 28 | No Improvement |
| Polyvalent Ions/Metal Salts | Sodium Carbonate | 45.848 mM | 24 | No Improvement |
| Polyvalent Ions/Metal Salts | Sodium Carbonate | 50.942 mM | 25 | No Improvement |
| Polyvalent Ions/Metal Salts | Sodium Perchlorate | 100 mM | 47 | No Improvement |
| Polyvalent Ions/Metal Salts | Sodium Perchlorate | 150 mM | 43 | No Improvement |
| Polyvalent Ions/Metal Salts | Sodium Perchlorate | 260 mM | 38 | No Improvement |
| Polyvalent Ions/Metal Salts | Sodium Phosphate | 100 mM | 65 | No Improvement |
| Polyvalent Ions/Metal Salts | Sodium Phosphate | 150 mM | 65 | No Improvement |
| Polyvalent Ions/Metal Salts | Sodium Phosphate | 260 mM | 66 | No Improvement |
| HRP Stabilizer Components | BioRad AbGuard HRP Stabilization Buffer | 10% | 78 | Slight Improvement. Needs further assay optimization |
| HRP Stabilizer Components | BioRad AbGuard HRP Stabilization Buffer | 11% | 77 | Slight Improvement. Needs further assay optimization |
| HRP Stabilizer Components | BioRad AbGuard HRP Stabilization Buffer | 12% | 78 | Slight Improvement. Needs further assay optimization |
| HRP Stabilizer Components | BioRad AbGuard HRP Stabilization Buffer | 13% | 81 | Slight Improvement. Needs further assay optimization |
| HRP Stabilizer Components | BioRad AbGuard HRP Stabilization Buffer | 14% | 80 | Slight Improvement. Needs further assay optimization |
| HRP Stabilizer Components | BioRad AbGuard HRP Stabilization Buffer | 15% | 81 | Slight Improvement. Needs further assay optimization |
| HRP Stabilizer Components | BioRad AbGuard HRP Stabilization Buffer | 16% | 90 | Slight Improvement. Needs further assay optimization |
| HRP Stabilizer Components | BioRad AbGuard HRP Stabilization Buffer | 17% | 81 | Slight Improvement. Needs further assay optimization |
| HRP Stabilizer Components | BioRad AbGuard HRP Stabilization Buffer | 18% | 87 | Slight Improvement. Needs further assay optimization |
| HRP Stabilizer Components | BioRad AbGuard HRP Stabilization Buffer | 19% | 85 | Slight Improvement. Needs further assay optimization |
| HRP Stabilizer Components | BioRad AbGuard HRP Stabilization Buffer | 20% | 83 | Slight Improvement. Needs further assay optimization |
| HRP Stabilizer Components | BioRad AbGuard HRP Stabilization Buffer | 21% | 86 | Slight Improvement. Needs further assay optimization |
| HRP Stabilizer Components | BioRad AbGuard HRP Stabilization Buffer | 22% | 86 | Slight Improvement. Needs further assay optimization |
| HRP Stabilizer Components | BioRad AbGuard HRP Stabilization Buffer | 23% | 89 | Slight Improvement. Needs further assay optimization |
| HRP Stabilizer Components | BioRad AbGuard HRP Stabilization Buffer | 24% | 86 | Slight Improvement. Needs further assay optimization |
| HRP Stabilizer Components | BioRad AbGuard HRP Stabilization Buffer | 25% | 84 | Slight Improvement. Needs further assay optimization |
| Formaldehyde Releaser | Diazolidinyl Urea + DMSO + Zinc Chloride | 1% (50 g/mL, 100 mL/L, 5.8 g/L) | 34 | No Improvement |
| Formaldehyde Releaser | Diazolidinyl Urea + DMSO + Zinc Chloride | 5% (50 g/mL, 100 mL/L, 5.8 g/L) | 62 | No Improvement |
| Formaldehyde Releaser | Diazolidinyl Urea + DMSO + Zinc Chloride | 10% (50 g/mL, 100 mL/L, 5.8 g/L) | 58 | No Improvement |
| Formaldehyde Releaser | Diazolidinyl Urea + DMSO + Zinc Chloride | 25% (50 g/mL, 100 mL/L, 5.8 g/L) | 62 | No Improvement |
| Formaldehyde Releaser | Diazolidinyl Urea + DMSO + Zinc Chloride | 50% (50 g/mL, 100 mL/L, 5.8 g/L) | 30 | No Improvement |
| Plasma | Bovine B | 1 g/L | 68 | No Improvement |
| Plasma | Bovine B | 2 g/L | 65 | No Improvement |
| Plasma | Bovine B | 4 g/L | 68 | No Improvement |
| Gelatins | CW Fish Skin | 1 g/L | 67 | No Improvement |
| Gelatins | CW Fish Skin | 2 g/L | 68 | No Improvement |

APPENDIX B

| Compound aassification | Additive | Additive Concentration | % Hb Recovery | Results |
|---|---|---|---|---|
| Gelatins | CW Fish Skin | 4 g/L | 71 | No Improvement |
| Gelatins | Procine A (110 g) | 1 g/L | 74 | No Improvement |
| Gelatins | Procine A (110 g) | 2 g/L | 83 | No Improvement |
| Gelatins | Procine A (110 g) | 4 g/L | 69 | No Improvement |
| Gelatins | Procine A (175 g) | 1 g/L | 72 | No Improvement |
| Gelatins | Procine A (175 g) | 2 g/L | 76 | No Improvement |
| Gelatins | Procine A (175 g) | 4 g/L | 67 | No Improvement |
| Gelatins | Procine A (300 g) | 1 g/L | 67 | No Improvement |
| Gelatins | Procine A (300 g) | 2 g/L | 66 | No Improvement |
| Gelatins | Procine A (300 g) | 4 g/L | 65 | No Improvement |
| Polyvalent Ions/Metal Salts | Magnesium Chloride | 5 mM | 76 | Magnesium Cation shows improvement in % Hb Recovery around 10 mM |
| Polyvalent Ions/Metal Salts | Magnesium Chloride | 10 mM | 74 | Magnesium Cation shows improvement in % Hb Recovery around 10 mM |
| Polyvalent Ions/Metal Salts | Magnesium Chloride | 20 mM | 77 | Magnesium Cation shows improvement in % Hb Recovery around 10 mM |
| Polyvalent Ions/Metal Salts | Magnesium Chloride | 30 mM | 74 | Magnesium Cation shows improvement in % Hb Recovery around 10 mM |
| Polyvalent Ions/Metal Salts | Magnesium Chloride | 40 mM | 74 | Magnesium Cation shows improvement in % Hb Recovery around 10 mM |
| Polyvalent Ions/Metal Salts | Magnesium Chloride | 50 mM | 72 | Magnesium Cation shows improvement in % Hb Recovery around 10 mM |
| Polyvalent Ions/Metal Salts | Magnesium Gluconate | 5 mM | 77 | Magnesium Cation shows improvement in % Hb Recovery around 10 mM |
| Polyvalent Ions/Metal Salts | Magnesium Gluconate | 10 mM | 75 | Magnesium Cation shows improvement in % Hb Recovery around 10 mM |
| Polyvalent Ions/Metal Salts | Magnesium Gluconate | 20 mM | 78 | Magnesium Cation shows improvement in % Hb Recovery around 10 mM |
| Polyvalent Ions/Metal Salts | Magnesium Gluconate | 30 mM | 73 | Magnesium Cation shows improvement in % Hb Recovery around 10 mM |
| Polyvalent Ions/Metal Salts | Magnesium Gluconate | 40 mM | 77 | Magnesium Cation shows improvement in % Hb Recovery around 10 mM |
| Polyvalent Ions/Metal Salts | Magnesium Gluconate | 50 mM | 73 | Magnesium Cation shows improvement in % Hb Recovery around 10 mM |
| Polyvalent Ions/Metal Salts | Magnesium Sulfate | 5 mM | 74 | Magnesium Cation shows improvement in % Hb Recovery around 10 mM |
| Polyvalent Ions/Metal Salts | Magnesium Sulfate | 10 mM | 74 | Magnesium Cation shows improvement in % Hb Recovery around 10 mM |
| Polyvalent Ions/Metal Salts | Magnesium Sulfate | 20 mM | 77 | Magnesium Cation shows improvement in % Hb Recovery around 10 mM |
| Polyvalent Ions/Metal Salts | Magnesium Sulfate | 30 mM | 73 | Magnesium Cation shows improvement in % Hb Recovery around 10 mM |
| Polyvalent Ions/Metal Salts | Magnesium Sulfate | 40 mM | 78 | Magnesium Cation shows improvement in % Hb Recovery around 10 mM |
| Polyvalent Ions/Metal Salts | Magnesium Sulfate | 50 mM | 76 | Magnesium Cation shows improvement in % Hb Recovery around 10 mM |
| Aldehydes | Formaldehyde Solution | 0.010% | 54 | No Improvement |
| Aldehydes | Formaldehyde Solution | 0.015% | 52 | No Improvement |
| Aldehydes | Formaldehyde Solution | 0.020% | 55 | No Improvement |
| Aldehydes | Formaldehyde Solution | 0.025% | 53 | No Improvement |
| Aldehydes | Formaldehyde Solution | 0.030% | 53 | No Improvement |
| Aldehydes | Formaldehyde Solution | 0.035% | 54 | No Improvement |
| Aldehydes | Formaldehyde Solution | 0.040% | 55 | No Improvement |
| Aldehydes | Formaldehyde Solution | 0.045% | 54 | No Improvement |
| Aldehydes | Formaldehyde Solution | 0.050% | 52 | No Improvement |
| Aldehydes | Formaldehyde Solution | 0.055% | 53 | No Improvement |

APPENDIX B

| Compound aassification | Additive | Additive Concentration | % Hb Recovery | Results |
|---|---|---|---|---|
| Aldehydes | Formaldehyde Solution | 0.060% | 56 | No Improvement |
| Aldehydes | Formaldehyde Solution | 0.065% | 53 | No Improvement |
| Aldehydes | Formaldehyde Solution | 0.070% | 53 | No Improvement |
| Aldehydes | Formaldehyde Solution | 0.075% | 54 | No Improvement |
| Aldehydes | Formaldehyde Solution | 0.080% | 55 | No Improvement |
| Aldehydes | Formaldehyde Solution | 0.085% | 55 | No Improvement |
| Aldehydes | Formaldehyde Solution | 0.090% | 54 | No Improvement |
| Aldehydes | Formaldehyde Solution | 0.095% | 53 | No Improvement |
| Aldehydes | Formaldehyde Solution | 0.100% | 53 | No Improvement |
| Aldehydes | Paraformaldehyde Solution | 0.010% | 46 | No Improvement |
| Aldehydes | Paraformaldehyde Solution | 0.015% | 39 | No Improvement |
| Aldehydes | Paraformaldehyde Solution | 0.020% | 32 | No Improvement |
| Aldehydes | Paraformaldehyde Solution | 0.025% | 33 | No Improvement |
| Aldehydes | Paraformaldehyde Solution | 0.030% | 29 | No Improvement |
| Aldehydes | Paraformaldehyde Solution | 0.035% | 27 | No Improvement |
| Aldehydes | Paraformaldehyde Solution | 0.040% | 24 | No Improvement |
| Aldehydes | Paraformaldehyde Solution | 0.045% | 21 | No Improvement |
| Aldehydes | Paraformaldehyde Solution | 0.050% | 16 | No Improvement |
| Aldehydes | Paraformaldehyde Solution | 0.055% | 15 | No Improvement |
| Aldehydes | Paraformaldehyde Solution | 0.060% | 14 | No Improvement |
| Aldehydes | Glutaraldehyde Solution | 0.010% | 59 | No Improvement |
| Aldehydes | Glutaraldehyde Solution | 0.015% | 61 | No Improvement |
| Aldehydes | Glutaraldehyde Solution | 0.020% | 62 | No Improvement |
| Aldehydes | Glutaraldehyde Solution | 0.025% | 60 | No Improvement |
| Aldehydes | Glutaraldehyde Solution | 0.030% | 56 | No Improvement |
| Aldehydes | Glutaraldehyde Solution | 0.035% | 60 | No Improvement |
| Aldehydes | Glutaraldehyde Solution | 0.040% | 61 | No Improvement |
| Aldehydes | Glutaraldehyde Solution | 0.045% | 60 | No Improvement |
| Aldehydes | Glutaraldehyde Solution | 0.050% | 57 | No Improvement |
| Aldehydes | Glutaraldehyde Solution | 0.055% | 107 | Assay Interference |
| Aldehydes | Glutaraldehyde Solution | 0.060% | 102 | Assay Interference |
| Aldehydes | Glutaraldehyde Solution | 0.065% | 82 | Assay Interference |
| Aldehydes | Glutaraldehyde Solution | 0.070% | 100 | Assay Interference |
| Aldehydes | Glutaraldehyde Solution | 0.075% | 53 | No Improvement |
| Aldehydes | Glutaraldehyde Solution | 0.080% | 54 | No Improvement |
| Aldehydes | Glutaraldehyde Solution | 0.085% | 54 | No Improvement |
| Aldehydes | Glutaraldehyde Solution | 0.090% | 53 | No Improvement |
| Aldehydes | Glutaraldehyde Solution | 0.095% | 51 | No Improvement |
| Aldehydes | Glutaraldehyde Solution | 0.100% | 48 | No Improvement |
| Formaldehyde Releaser | Diazolidinyl Urea + DMSO + Zinc Chloride | 0.1% (50 g/mL, 100 mL/L, 5.8 g/L) | 66 | No Improvement |
| Formaldehyde Releaser | Diazolidinyl Urea + DMSO + Zinc Chloride | 0.25% (50 g/mL, 100 mL/L, 5.8 g/L) | 65 | No Improvement |
| Formaldehyde Releaser | Diazolidinyl Urea + DMSO + Zinc Chloride | 0.5% (50 g/mL, 100 mL/L, 5.8 g/L) | 63 | No Improvement |
| Formaldehyde Releaser | Diazolidinyl Urea + DMSO + Zinc Chloride | 0.75% (50 g/mL, 100 mL/L, 5.8 g/L) | 69 | No Improvement |
| Formaldehyde Releaser | Diazolidinyl Urea + DMSO + Zinc Chloride | 1% (50 g/mL, 100 mL/L, 5.8 g/L) | 64 | No Improvement |
| Formaldehyde Releaser | Diazolidinyl Urea + DMSO + Zinc Chloride | 2% (50 g/mL, 100 mL/L, 5.8 g/L) | 64 | No Improvement |
| Formaldehyde Releaser | Diazolidinyl Urea + DMSO + Zinc Chloride | 3% (50 g/mL, 100 mL/L, 5.8 g/L) | 63 | No Improvement |
| Formaldehyde Releaser | Diazolidinyl Urea + DMSO + Zinc Chloride | 4% (50 g/mL, 100 mL/L, 5.8 g/L) | 64 | No Improvement |
| Formaldehyde Releaser | Diazolidinyl Urea + DMSO + Zinc Chloride | 5% (50 g/mL, 100 mL/L, 5.8 g/L) | 59 | No Improvement |
| Formaldehyde Releaser | Imidazolidinyl Urea + DMSO + Zinc Chloride | 0.1% (50 g/mL, 100 mL/L, 5.8 g/L) | 70 | No Improvement |
| Formaldehyde Releaser | Imidazolidinyl Urea + DMSO + Zinc Chloride | 0.25% (50 g/mL, 100 mL/L, 5.8 g/L) | 66 | No Improvement |
| Formaldehyde Releaser | Imidazolidinyl Urea + DMSO + Zinc Chloride | 0.5% (50 g/mL, 100 mL/L, 5.8 g/L) | 69 | No Improvement |
| Formaldehyde Releaser | Imidazolidinyl Urea + DMSO + Zinc Chloride | 0.75% (50 g/mL, 100 mL/L, 5.8 g/L) | 62 | No Improvement |
| Formaldehyde Releaser | Imidazolidinyl Urea + DMSO + Zinc Chloride | 1% (50 g/mL, 100 mL/L, 5.8 g/L) | 70 | No Improvement |
| Formaldehyde Releaser | Imidazolidinyl Urea + DMSO + Zinc Chloride | 2% (50 g/mL, 100 mL/L, 5.8 g/L) | 65 | No Improvement |
| Formaldehyde Releaser | Imidazolidinyl Urea + DMSO + Zinc Chloride | 3% (50 g/mL, 100 mL/L, 5.8 g/L) | 66 | No Improvement |
| Formaldehyde Releaser | Imidazolidinyl Urea + DMSO + Zinc Chloride | 4% (50 g/mL, 100 mL/L, 5.8 g/L) | 63 | No Improvement |

-continued

APPENDIX B

| Compound aassification | Additive | Additive Concentration | % Hb Recovery | Results |
|---|---|---|---|---|
| Formaldehyde Releaser | Imidazolidinyl Urea + DMSO + Zinc Chloride | 5% (50 g/mL, 100 mL/L, 5.8 g/L) | 65 | No Improvement |
| Formaldehyde Releaser | Diazolidinyl Urea | 10 mM | 60 | No Improvement |
| Formaldehyde Releaser | Diazolidinyl Urea | 25 mM | 61 | No Improvement |
| Formaldehyde Releaser | Diazolidinyl Urea | 50 mM | 49 | No Improvement |
| Formaldehyde Releaser | Diazolidinyl Urea | 75 mM | 58 | No Improvement |
| Formaldehyde Releaser | Diazolidinyl Urea | 100 mM | 50 | No Improvement |
| Formaldehyde Releaser | Imidazolidinyl Urea | 10 mM | 61 | No Improvement |
| Formaldehyde Releaser | Imidazolidinyl Urea | 25 mM | 62 | No Improvement |
| Formaldehyde Releaser | Imidazolidinyl Urea | 50 mM | 57 | No Improvement |
| Formaldehyde Releaser | Imidazolidinyl Urea | 75 mM | 55 | No Improvement |
| Formaldehyde Releaser | Imidazolidinyl Urea | 100 mM | 51 | No Improvement |
| Formaldehyde Releaser | Soduim hyrdoxylmethyl glycinate | 10 mM | 48 | No Improvement |
| Formaldehyde Releaser | Soduim hyrdoxylmethyl glycinate | 25 mM | 43 | No Improvement |
| Formaldehyde Releaser | Soduim hyrdoxylmethyl glycinate | 50 mM | 74 | No Improvement |
| Formaldehyde Releaser | Soduim hyrdoxylmethyl glycinate | 75 mM | 53 | No Improvement |
| Formaldehyde Releaser | Soduim hyrdoxylmethyl glycinate | 90 mM | 36 | No Improvement |
| Osmolytes | Betaine | 0.05M | 70 | Betaine shows improvement in % Hb Recovery at high concentrations |
| Osmolytes | Betaine | 0.5M | 70 | Betaine shows improvement in % Hb Recovery at high concentrations |
| Osmolytes | Betaine | 1.25M | 75 | Betaine shows improvement in % Hb Recovery at high concentrations |
| Osmolytes | Betaine | 2.5M | 73 | Betaine shows improvement in % Hb Recovery at high concentrations |
| Osmolytes | Betaine | 3.75M | 82 | Betaine shows improvement in % Hb Recovery at high concentrations |
| Osmolytes | Betaine | 5M | 80 | Betaine shows improvement in % Hb Recovery at high concentrations |
| Osmolytes | Trimethylamine N-oxide (TMANO) | 0.043M | 70 | Slight Improvement |
| Osmolytes | Trimethylamine N-oxide (TMANO) | 0.43M | 70 | Slight Improvement |
| Osmolytes | Trimethylamine N-oxide (TMANO) | 1.1M | 74 | Slight Improvement |
| Osmolytes | Trimethylamine N-oxide (TMANO) | 2.15M | 72 | Slight Improvement |
| Osmolytes | Trimethylamine N-oxide (TMANO) | 3.2M | 74 | Slight Improvement |
| Osmolytes | Trimethylamine N-oxide (TMANO) | 4.3M | 68 | Slight Improvement |
| Osmolytes | Betaine | 2.5M | 72 | Betaine shows improvement in % Hb Recovery at high concentrations |
| Osmolytes | Betaine | 3M | 73 | Betaine shows improvement in % Hb Recovery at high concentrations |
| Osmolytes | Betaine | 3.5M | 79 | Betaine shows improvement in % Hb Recovery at high concentrations |
| Osmolytes | Betaine | 4M | 78 | Betaine shows improvement in % Hb Recovery at high concentrations |
| Osmolytes | Betaine | 4.5M | 80 | Betaine shows improvement in % Hb Recovery at high concentrations |
| Osmolytes | Betaine | 5M | 83 | Betaine shows improvement in % Hb Recovery at high concentrations |
| Osmolytes | Trimethylamine N-oxide (TMANO) | 2.5M | 65 | No Improvement |
| Osmolytes | Trimethylamine N-oxide (TMANO) | 3M | 64 | No Improvement |
| Osmolytes | Trimethylamine N-oxide (TMANO) | 3.5M | 73 | No Improvement |
| Osmolytes | Trimethylamine N-oxide (TMANO) | 4M | 69 | No Improvement |
| Osmolytes | Trimethylamine N-oxide (TMANO) | 4.3M | 58 | No Improvement |
| Detergent | Brij 35 (Component) | 0.005% | 63 | No Improvement |
| Detergent | Brij 35 (Component) | 0.010% | 59 | No Improvement |
| Detergent | Brij 35 (Component) | 0.050% | 69 | No Improvement |
| Detergent | Brij 35 (Component) | 0.100% | 62 | No Improvement |
| Detergent | Brij 35 (Component) | 0.200% | 57 | No Improvement |
| Detergent | Brij 58 (Component) | 0.005% | 63 | No Improvement |
| Detergent | Brij 58 (Component) | 0.010% | 67 | No Improvement |
| Detergent | Brij 58 (Component) | 0.050% | 65 | No Improvement |
| Detergent | Brij 58 (Component) | 0.100% | 63 | No Improvement |
| Detergent | Brij 58 (Component) | 0.200% | 49 | No Improvement |

-continued

APPENDIX B

| Compound aassification | Additive | Additive Concentration | % Hb Recovery | Results |
| --- | --- | --- | --- | --- |
| Detergent | Brij 35 (Spike) | 0.010% | 61 | No Improvement |
| Detergent | Brij 35 (Spike) | 0.050% | 59 | No Improvement |
| Detergent | Brij 35 (Spike) | 0.080% | 59 | No Improvement |
| Detergent | Brij 35 (Spike) | 0.100% | 58 | No Improvement |
| Detergent | Brij 58 (Spike) | 0.010% | 65 | No Improvement |
| Detergent | Brij 58 (Spike) | 0.050% | 61 | No Improvement |
| Detergent | Brij 58 (Spike) | 0.080% | 59 | No Improvement |
| Detergent | Brij 58 (Spike) | 0.100% | 53 | No Improvement |
| Polyvalent Ions/Metal Salts | Cobalt Chloride | 0.001M | 62 | No Improvement |
| Polyvalent Ions/Metal Salts | Cobalt Chloride | 0.01M | 68 | No Improvement |
| Polyvalent Ions/Metal Salts | Cobalt Chloride | 0.05M | 16 | No Improvement |
| Polyvalent Ions/Metal Salts | Cobalt Chloride + Sucrose | 0.001M + 2% | 73 | Slight Improvement with Sugars. Needs further assay optimization |
| Polyvalent Ions/Metal Salts | Cobalt Chloride + Sucrose | 0.01M + 2% | 77 | Slight Improvement with Sugars. Needs further assay optimization |
| Polyvalent Ions/Metal Salts | Cobalt Chloride + Sucrose | 0.05M + 2% | 17 | Slight Improvement with Sugars. Needs further assay optimization |
| Polyvalent Ions/Metal Salts | Magnesium Sulfate | 0.001M | 66 | Magnesium Cation shows improvement in % Hb Recovery around 10 mM |
| Polyvalent Ions/Metal Salts | Magnesium Sulfate | 0.01M | 75 | Magnesium Cation shows improvement in % Hb Recovery around 10 mM |
| Polyvalent Ions/Metal Salts | Magnesium Sulfate | 0.05M | 78 | Magnesium Cation shows improvement in % Hb Recovery around 10 mM |
| Polyvalent Ions/Metal Salts | Magnesium Sulfate + Sucrose | 0.001M + 2% | 72 | Magnesium Cation shows improvement in % Hb Recovery around 10 mM |
| Polyvalent Ions/Metal Salts | Magnesium Sulfate + Sucrose | 0.01M + 2% | 81 | Magnesium Cation shows improvement in % Hb Recovery around 10 mM |
| Polyvalent Ions/Metal Salts | Magnesium Sulfate + Sucrose | 0.05M + 2% | 80 | Magnesium Cation shows improvement in % Hb Recovery around 10 mM |
| Polyvalent Ions/Metal Salts | Copper Chloride | 1 mM | 64 | No Improvement |
| Polyvalent Ions/Metal Salts | Copper Chloride | 10 mM | 63 | No Improvement |
| Polyvalent Ions/Metal Salts | Copper Chloride | 25 mM | 42 | No Improvement |
| Polyvalent Ions/Metal Salts | Copper Chloride + Sucrose | 1 mM + 2% | 69 | No Improvement |
| Polyvalent Ions/Metal Salts | Copper Chloride + Sucrose | 10 mM + 2% | 69 | No Improvement |
| Polyvalent Ions/Metal Salts | Copper Chloride + Sucrose | 25 mM + 2% | 47 | No Improvement |
| Polyvalent Ions/Metal Salts | Iron (3) Chloride | 1 mM | 60 | No Improvement |
| Polyvalent Ions/Metal Salts | Iron (3) Chloride | 5 mM | 61 | No Improvement |
| Polyvalent Ions/Metal Salts | Iron (3) Chloride | 10 mM | 66 | No Improvement |
| Polyvalent Ions/Metal Salts | Iron (3) Chloride + Sucrose | 1 mM + 2% | 65 | No Improvement |
| Polyvalent Ions/Metal Salts | Iron (3) Chloride + Sucrose | 5 mM + 2% | 65 | No Improvement |
| Polyvalent Ions/Metal Salts | Iron (3) Chloride + Sucrose | 10 mM + 2% | 59 | No Improvement |
| Polyvalent Ions/Metal Salts | Nickel Chloride | 1 mM | 59 | No Improvement |
| Polyvalent Ions/Metal Salts | Nickel Chloride | 10 mM | 68 | No Improvement |
| Polyvalent Ions/Metal Salts | Nickel Chloride | 25 mM | 32 | No Improvement |
| Polyvalent Ions/Metal Salts | Nickel Chloride + Sucrose | 1 mM + 2% | 63 | No Improvement |
| Polyvalent Ions/Metal Salts | Nickel Chloride + Sucrose | 10 mM + 2% | 68 | No Improvement |
| Polyvalent Ions/Metal Salts | Nickel Chloride + Sucrose | 25 mM + 2% | 33 | No Improvement |
| Polyvalent Ions/Metal Salts | Zinc Chloride | 1 mM | 65 | No Improvement |
| Polyvalent Ions/Metal Salts | Zinc Chloride | 10 mM | 61 | No Improvement |
| Polyvalent Ions/Metal Salts | Zinc Chloride | 25 mM | 33 | No Improvement |
| Polyvalent Ions/Metal Salts | Zinc Chloride + Sucrose | 1 mM + 2% | 68 | No Improvement |
| Polyvalent Ions/Metal Salts | Zinc Chloride + Sucrose | 10 mM + 2% | 75 | No Improvement |
| Polyvalent Ions/Metal Salts | Zinc Chloride + Sucrose | 25 mM + 2% | 36 | No Improvement |
| Polyvalent Ions/Metal Salts | Calcium Chloride | 5 mM | 66 | Calcium cation shows improvement in % Hb Recovery at 10 mM |
| Polyvalent Ions/Metal Salts | Calcium Chloride | 10 mM | 65 | Calcium cation shows improvement in % Hb Recovery at 10 mM |
| Polyvalent Ions/Metal Salts | Calcium Chloride | 20 mM | 69 | Calcium cation shows improvement in % Hb Recovery at 10 mM |
| Polyvalent Ions/Metal Salts | Calcium Chloride | 30 mM | 59 | Calcium cation shows improvement in % Hb Recovery at 10 mM |

APPENDIX B

| Compound aassification | Additive | Additive Concentration | % Hb Recovery | Results |
|---|---|---|---|---|
| Polyvalent Ions/Metal Salts | Calcium Chloride | 40 mM | 62 | Calcium cation shows improvement in % Hb Recovery at 10 mM |
| Polyvalent Ions/Metal Salts | Calcium Chloride | 50 mM | 52 | Calcium cation shows improvement in % Hb Recovery at 10 mM |
| Polyvalent Ions/Metal Salts | Calcium Propionate | 5 mM | 62 | Calcium cation shows improvement in % Hb Recovery at 10 mM |
| Polyvalent Ions/Metal Salts | Calcium Propionate | 10 mM | 61 | Calcium cation shows improvement in % Hb Recovery at 10 mM |
| Polyvalent Ions/Metal Salts | Calcium Propionate | 20 mM | 70 | Calcium cation shows improvement in % Hb Recovery at 10 mM |
| Polyvalent Ions/Metal Salts | Calcium Propionate | 30 mM | 66 | Calcium cation shows improvement in % Hb Recovery at 10 mM |
| Polyvalent Ions/Metal Salts | Calcium Propionate | 40 mM | 62 | Calcium cation shows improvement in % Hb Recovery at 10 mM |
| Polyvalent Ions/Metal Salts | Calcium Propionate | 50 mM | 62 | Calcium cation shows improvement in % Hb Recovery at 10 mM |
| Polyvalent Ions/Metal Salts | Calcium Chloride + Cobalt Chloride | 5 mM + 5 mM | 68 | Calcium cation shows improvement in % Hb Recovery at 10 mM |
| Polyvalent Ions/Metal Salts | Calcium Chloride + Cobalt Chloride | 10 mM + 5 mM | 60 | Calcium cation shows improvement in % Hb Recovery at 10 mM |
| Polyvalent Ions/Metal Salts | Calcium Chloride + Cobalt Chloride | 5 mM + 10 mM | 58 | Calcium cation shows improvement in % Hb Recovery at 10 mM |
| Polyvalent Ions/Metal Salts | Calcium Chloride + Copper Chloride | 5 mM + 5 mM | 66 | Calcium cation shows improvement in % Hb Recovery at 10 mM |
| Polyvalent Ions/Metal Salts | Calcium Chloride + Copper Chloride | 10 mM + 5 mM | 50 | Calcium cation shows improvement in % Hb Recovery at 10 mM |
| Polyvalent Ions/Metal Salts | Calcium Chloride + Copper Chloride | 5 mM + 10 mM | 59 | Calcium cation shows improvement in % Hb Recovery at 10 mM |
| Polyvalent Ions/Metal Salts | Calcium Chloride + Iron (3) Chloride | 5 mM + 5 mM | 76 | Calcium cation shows improvement in % Hb Recovery at 10 mM |
| Polyvalent Ions/Metal Salts | Calcium Chloride + Iron (3) Chloride | 5 mM + 2.5 mM | 63 | Calcium cation shows improvement in % Hb Recovery at 10 mM |
| Polyvalent Ions/Metal Salts | Calcium Chloride + Iron (3) Chloride | 2.5 mM + 5 mM | 63 | Calcium cation shows improvement in % Hb Recovery at 10 mM |
| Polyvalent Ions/Metal Salts | Calcium Chloride + Magnesium Sulfate | 5 mM + 5 mM | 71 | Calcium cation shows improvement in % Hb Recovery at 10 mM |
| Polyvalent Ions/Metal Salts | Calcium Chloride + Magnesium Sulfate | 10 mM + 5 mM | 67 | Calcium cation shows improvement in % Hb Recovery at 10 mM |
| Polyvalent Ions/Metal Salts | Calcium Chloride + Magnesium Sulfate | 5 mM + 10 mM | 61 | Calcium cation shows improvement in % Hb Recovery at 10 mM |
| Polyvalent Ions/Metal Salts | Calcium Chloride + Nickel Chloride | 5 mM + 5 mM | 69 | Calcium cation shows improvement in % Hb Recovery at 10 mM |
| Polyvalent Ions/Metal Salts | Calcium Chloride + Nickel Chloride | 10 mM + 5 mM | 64 | Calcium cation shows improvement in % Hb Recovery at 10 mM |
| Polyvalent Ions/Metal Salts | Calcium Chloride + Nickel Chloride | 5 mM + 10 mM | 73 | Calcium cation shows improvement in % Hb Recovery at 10 mM |
| Polyvalent Ions/Metal Salts | Calcium Chloride + Zinc Chloride | 5 mM + 5 mM | 68 | Calcium cation shows improvement in % Hb Recovery at 10 mM |

APPENDIX B

| Compound aassification | Additive | Additive Concentration | % Hb Recovery | Results |
|---|---|---|---|---|
| Polyvalent Ions/Metal Salts | Calcium Chloride + Zinc Chloride | 10 mM + 5 mM | 66 | Calcium cation shows improvement in % Hb Recovery at 10 mM |
| Polyvalent Ions/Metal Salts | Calcium Chloride + Zinc Chloride | 5 mM + 10 mM | 63 | Calcium cation shows improvement in % Hb Recovery at 10 mM |
| Polyvalent Ions/Metal Salts | Cobalt Chloride + Copper Chloride | 5 mM + 5 mM | 59 | No Improvement |
| Polyvalent Ions/Metal Salts | Cobalt Chloride + Copper Chloride | 10 mM + 5 mM | 47 | No Improvement |
| Polyvalent Ions/Metal Salts | Cobalt Chloride + Copper Chloride | 5 mM + 10 mM | 40 | No Improvement |
| Polyvalent Ions/Metal Salts | Cobalt Chloride + Iron (3) Chloride | 5 mM + 5 mM | 66 | No Improvement |
| Polyvalent Ions/Metal Salts | Cobalt Chloride + Iron (3) Chloride | 5 mM + 2.5 mM | 68 | No Improvement |
| Polyvalent Ions/Metal Salts | Cobalt Chloride + Iron (3) Chloride | 2.5 mM + 5 mM | 65 | No Improvement |
| Polyvalent Ions/Metal Salts | Cobalt Chloride + Magnesium Sulfate | 5 mM + 5 mM | 74 | No Improvement |
| Polyvalent Ions/Metal Salts | Cobalt Chloride + Magnesium Sulfate | 10 mM + 5 mM | 66 | No Improvement |
| Polyvalent Ions/Metal Salts | Cobalt Chloride + Magnesium Sulfate | 5 mM + 10 mM | 70 | No Improvement |
| Polyvalent Ions/Metal Salts | Cobalt Chloride + Nickel Chloride | 5 mM + 5 mM | 75 | No Improvement |
| Polyvalent Ions/Metal Salts | Cobalt Chloride + Nickel Chloride | 10 mM + 5 mM | 49 | No Improvement |
| Polyvalent Ions/Metal Salts | Cobalt Chloride + Nickel Chloride | 5 mM + 10 mM | 43 | No Improvement |
| Polyvalent Ions/Metal Salts | Cobalt Chloride + Zinc Chloride | 5 mM + 5 mM | 71 | No Improvement |
| Polyvalent Ions/Metal Salts | Cobalt Chloride + Zinc Chloride | 10 mM + 5 mM | 35 | No Improvement |
| Polyvalent Ions/Metal Salts | Cobalt Chloride + Zinc Chloride | 5 mM + 10 mM | 34 | No Improvement |
| Polyvalent Ions/Metal Salts | Copper Chloride + Iron (3) Chloride | 5 mM + 5 mM | 67 | No Improvement |
| Polyvalent Ions/Metal Salts | Copper Chloride + Iron (3) Chloride | 5 mM + 2.5 mM | 61 | No Improvement |
| Polyvalent Ions/Metal Salts | Copper Chloride + Iron (3) Chloride | 2.5 mM + 5 mM | 70 | No Improvement |
| Polyvalent Ions/Metal Salts | Copper Chloride + Magnesium Sulfate | 5 mM + 5 mM | 70 | No Improvement |
| Polyvalent Ions/Metal Salts | Copper Chloride + Magnesium Sulfate | 10 mM + 5 mM | 63 | No Improvement |
| Polyvalent Ions/Metal Salts | Copper Chloride + Magnesium Sulfate | 5 mM + 10 mM | 68 | No Improvement |
| Polyvalent Ions/Metal Salts | Copper Chloride + Nickel Chloride | 5 mM + 5 mM | 68 | No Improvement |
| Polyvalent Ions/Metal Salts | Copper Chloride + Nickel Chloride | 10 mM + 5 mM | 42 | No Improvement |
| Polyvalent Ions/Metal Salts | Copper Chloride + Nickel Chloride | 5 mM + 10 mM | 44 | No Improvement |
| Polyvalent Ions/Metal Salts | Copper Chloride + Zinc Chloride | 5 mM + 5 mM | 68 | No Improvement |
| Polyvalent Ions/Metal Salts | Copper Chloride + Zinc Chloride | 10 mM + 5 mM | 38 | No Improvement |
| Polyvalent Ions/Metal Salts | Copper Chloride + Zinc Chloride | 5 mM + 10 mM | 55 | No Improvement |
| Polyvalent Ions/Metal Salts | Iron (3) Chloride + Magnsium Sulfate | 5 mM + 5 mM | 71 | No Improvement |
| Polyvalent Ions/Metal Salts | Iron (3) Chloride + Magnsium Sulfate | 5 mM + 2.5 mM | 68 | No Improvement |
| Polyvalent Ions/Metal Salts | Iron (3) Chloride + Magnsium Sulfate | 2.5 mM + 5 mM | 63 | No Improvement |
| Polyvalent Ions/Metal Salts | Iron (3) Chloride + Nickel Chloride | 5 mM + 5 mM | 63 | No Improvement |
| Polyvalent Ions/Metal Salts | Iron (3) Chloride + Nickel Chloride | 5 mM + 2.5 mM | 58 | No Improvement |
| Polyvalent Ions/Metal Salts | Iron (3) Chloride + Nickel Chloride | 2.5 mM + 5 mM | 71 | No Improvement |
| Polyvalent Ions/Metal Salts | Iron (3) Chloride + Zinc Chloride | 5 mM + 5 mM | 61 | No Improvement |
| Polyvalent Ions/Metal Salts | Iron (3) Chloride + Zinc Chloride | 5 mM + 2.5 mM | 56 | No Improvement |
| Polyvalent Ions/Metal Salts | Iron (3) Chloride + Zinc Chloride | 2.5 mM + 5 mM | 66 | No Improvement |
| Polyvalent Ions/Metal Salts | Magnesium Sulfate + Nickel Chloride | 5 mM + 5 mM | 73 | Magnesium Cation shows improvement in % Hb Recovery around 10 mM |
| Polyvalent Ions/Metal Salts | Magnesium Sulfate + Nickel Chloride | 10 mM + 5 mM | 68 | Magnesium Cation shows improvement in % Hb Recovery around 10 mM |
| Polyvalent Ions/Metal Salts | Magnesium Sulfate + Nickel Chloride | 5 mM + 10 mM | 70 | Magnesium Cation shows improvement in % Hb Recovery around 10 mM |
| Polyvalent Ions/Metal Salts | Magnesium Sulfate + Zinc Chloride | 5 mM + 5 mM | 74 | Magnesium Cation shows improvement in % Hb Recovery around 10 mM |
| Polyvalent Ions/Metal Salts | Magnesium Sulfate + Zinc Chloride | 10 mM + 5 mM | 73 | Magnesium Cation shows improvement in % Hb Recovery around 10 mM |
| Polyvalent Ions/Metal Salts | Magnesium Sulfate + Zinc Chloride | 5 mM + 10 mM | 74 | Magnesium Cation shows improvement in % Hb Recovery around 10 mM |
| Polyvalent Ions/Metal Salts | Nickel Chloride + Zinc Chloride | 5 mM + 5 mM | 74 | No Improvement |
| Polyvalent Ions/Metal Salts | Nickel Chloride + Zinc Chloride | 10 mM + 5 mM | 47 | No Improvement |
| Polyvalent Ions/Metal Salts | Nickel Chloride + Zinc Chloride | 5 mM + 10 mM | 35 | No Improvement |
| HRP Stabilizer Components | HRP Conjugate Stabilizer (PN ab171537) (spike) | 5% | 82 | Improvement in % Hb Recovery |
| HRP Stabilizer Components | HRP Conjugate Stabilizer (PN ab171537) (spike) | 10% | 77 | Improvement in % Hb Recovery |
| HRP Stabilizer Components | HRP Conjugate Stabilizer (PN ab171537) (spike) | 25% | 76 | Improvement in % Hb Recovery |
| HRP Stabilizer Components | BioRad AbGuard HRP Stabilization Buffer (spike) | 5% | 72 | Slight Improvement. Needs further assay optimization |
| HRP Stabilizer Components | BioRad AbGuard HRP Stabilization Buffer (spike) | 10% | 78 | Slight Improvement. Needs further assay optimization |

APPENDIX B

| Compound aassification | Additive | Additive Concentration | % Hb Recovery | Results |
|---|---|---|---|---|
| HRP Stabilizer Components | BioRad AbGuard HRP Stabilization Buffer (spike) | 25% | 85 | Slight Improvement. Needs further assay optimization |
| HRP Stabilizer Components | Fisher HRP Sol (spike) | 5% | 65 | No Improvement |
| HRP Stabilizer Components | Fisher HRP Sol (spike) | 10% | 62 | No Improvement |
| HRP Stabilizer Components | Fisher HRP Sol (spike) | 25% | 57 | No Improvement |
| HRP Stabilizer Components | IC Tech (spike) | 5% | 64 | No Improvement |
| HRP Stabilizer Components | IC Tech (spike) | 10% | 68 | No Improvement |
| HRP Stabilizer Components | IC Tech (spike) | 25% | 65 | No Improvement |
| HRP Stabilizer Components | HRP Conjugate Stabilizer (PN SZ02) (spike) | 5% | 78 | Improvement in % Hb Recovery |
| HRP Stabilizer Components | HRP Conjugate Stabilizer (PN SZ02) (spike) | 10% | 86 | Improvement in % Hb Recovery |
| HRP Stabilizer Components | HRP Conjugate Stabilizer (PN SZ02) (spike) | 25% | 82 | Improvement in % Hb Recovery |
| HRP Stabilizer Components | HRP Conjugate Stabilizer (PN ab171537) (component) | 1% | 69 | Improvement in % Hb Recovery |
| HRP Stabilizer Components | HRP Conjugate Stabilizer (PN ab171537) (component) | 2.50% | 67 | Improvement in % Hb Recovery |
| HRP Stabilizer Components | HRP Conjugate Stabilizer (PN ab171537) (component) | 5% | 70 | Improvement in % Hb Recovery |
| HRP Stabilizer Components | HRP Conjugate Stabilizer (PN SZ02) (comp) | 1% | 67 | Improvement in % Hb Recovery |
| HRP Stabilizer Components | HRP Conjugate Stabilizer (PN 5Z02) (comp) | 2.50% | 69 | Improvement in % Hb Recovery |
| HRP Stabilizer Components | HRP Conjugate Stabilizer (PN SZ02) (comp) | 5% | 69 | Improvement in % Hb Recovery |
| HRP Stabilizer Components | Fisher HRP Sol (comp) | 1% | 65 | No Improvement |
| HRP Stabilizer Components | Fisher HRP Sol (comp) | 2.50% | 65 | No Improvement |
| HRP Stabilizer Components | Fisher HRP Sol (comp) | 5% | 64 | No Improvement |
| HRP Stabilizer Components | ID Stabilization Buffer (comp) | 1% | 67 | No Improvement |
| HRP Stabilizer Components | ID Stabilization Buffer (comp) | 2.50% | 66 | No Improvement |
| HRP Stabilizer Components | ID Stabilization Buffer (comp) | 5% | 65 | No Improvement |
| HRP Stabilizer Components | BioRad AbGuard HRP Stabilization Buffer (comp) | 10% | 74 | Slight Improvement. Needs further assay optimization |
| HRP Stabilizer Components | BioRad AbGuard HRP Stabilization Buffer (comp) | 25% | 83 | Slight Improvement. Needs further assay optimization |
| HRP Stabilizer Components | BioRad AbGuard HRP Stabilization Buffer (comp) | 40% | 90 | Slight Improvement. Needs further assay optimization |
| HRP Stabilizer Components | IC Tech (comp) | 1% | 67 | No Improvement |
| HRP Stabilizer Components | IC Tech (comp) | 5% | 67 | No Improvement |
| HRP Stabilizer Components | IC Tech (comp) | 10% | 67 | No Improvement |
| Polyvalent Ions/Metal Salts | Calcium Propionate + PEG 8000 | 0.1% + 3% | 64 | No Improvement |
| Polyvalent Ions/Metal Salts | Calcium Propionate + PEG 8000 | 0.2% + 3% | 63 | No improvement |
| Polyvalent Ions/Metal Salts | Calcium Propionate + PEG 8000 | 0.3% + 3% | 66 | No improvement |
| Polyvalent Ions/Metal Salts | Calcium Propionate + Calcium Chloride + PEG 8000 | 0.1% + 3% | 65 | No improvement |
| Polyvalent Ions/Metal Salts | Calcium Propionate + Calcium Chloride + PEG 8000 | 0.2% + 3% | 68 | No improvement |
| Polyvalent Ions/Metal Salts | Calcium Propionate + Calcium Chloride + PEG 8000 | 0.3% + 3% | 62 | No improvement |
| HRP Stabilizer Components | 4-Bromophenol | 0.001% | 59 | No Improvement |
| HRP Stabilizer Components | 4-Bromophenol | 0.005% | 59 | No Improvement |
| HRP Stabilizer Components | 4-Bromophenol | 0.01% | 48 | No Improvement |
| HRP Stabilizer Components | 4-Bromophenol | 0.05% | 54 | No Improvement |
| HRP Stabilizer Components | 8-anilino-1-napthalene sulfonic acid (ANSA) | 0.01% | 61 | No Improvement |
| HRP Stabilizer Components | 8-anilino-1-napthalene sulfonic acid (ANSA) | 0.05% | 68 | No Improvement |
| HRP Stabilizer Components | 8-anilino-1-napthalene sulfonic acid (ANSA) | 0.10% | 59 | No Improvement |
| HRP Stabilizer Components | 8-anilino-1-napthalene sulfonic acid (ANSA) | 0.50% | 42 | No Improvement |
| HRP Stabilizer Components | Proclin 300 | 0.00005% | 61 | No Improvement |
| HRP Stabilizer Components | Proclin 300 | 0.0001% | 61 | No Improvement |
| HRP Stabilizer Components | Proclin 300 | 0.0002% | 55 | No Improvement |
| Polyvalent Ions/Metal Salts | Cobalt Chloride | 0.1 mM | 67 | No Improvement |
| Polyvalent Ions/Metal Salts | Cobalt Chloride | 1 mM | 71 | No Improvement |
| Polyvalent Ions/Metal Salts | Cobalt Chloride | 10 mM | 63 | No Improvement |
| Polyvalent Ions/Metal Salts | Cobalt Chloride + Sucrose | 0.1 mM + 2% | 69 | No Improvement |
| Polyvalent Ions/Metal Salts | Cobalt Chloride + Sucrose | 1 mM + 2% | 69 | No Improvement |
| Polyvalent Ions/Metal Salts | Cobalt Chloride + Sucrose | 10 mM + 2% | 74 | No Improvement |
| Polyvalent Ions/Metal Salts | Magnesium Sulfate | 0.1 mM | 73 | Magnesium Cation shows improvement in % Hb Recovery around 10 mM |

-continued

APPENDIX B

| Compound aassification | Additive | Additive Concentration | % Hb Recovery | Results |
|---|---|---|---|---|
| Polyvalent Ions/Metal Salts | Magnesium Sulfate | 1 mM | 73 | Magnesium Cation shows improvement in % Hb Recovery around 10 mM |
| Polyvalent Ions/Metal Salts | Magnesium Sulfate | 10 mM | 56 | Magnesium Cation shows improvement in % Hb Recovery around 10 mM |
| Polyvalent Ions/Metal Salts | Magnesium Sulfate + Sucrose | 0.1 mM + 2% | 79 | Magnesium Cation shows improvement in % Hb Recovery around 10 mM |
| Polyvalent Ions/Metal Salts | Magnesium Sulfate + Sucrose | 1 mM + 2% | 68 | Magnesium Cation shows improvement in % Hb Recovery around 10 mM |
| Polyvalent Ions/Metal Salts | Magnesium Sulfate + Sucrose | 10 mM + 2% | 71 | Magnesium Cation shows improvement in % Hb Recovery around 10 mM |
| HRP Stabilizer Components | Candor HRP Protector (spike) | 25% | 65 | No Improvement |
| HRP Stabilizer Components | Candor HRP Protector (spike) | 10% | 61 | No Improvement |
| HRP Stabilizer Components | Candor HRP Protector (spike) | 5% | 62 | No Improvement |
| HRP Stabilizer Components | Innova LifeXtend Stabilizer (spike) | 25% | 62 | No Improvement |
| HRP Stabilizer Components | Innova LifeXtend Stabilizer (spike) | 10% | 68 | No Improvement |
| HRP Stabilizer Components | Innova LifeXtend Stabilizer (spike) | 5% | 63 | No Improvement |
| Aldehydes | Acetaldehyde | 10 mM | 56 | No Improvement |
| Aldehydes | Acetaldehyde | 25 mM | 48 | No Improvement |
| Aldehydes | Acetaldehyde | 50 mM | 43 | No Improvement |
| Aldehydes | Benzaldehyde | 10 mM | 46 | No Improvement |
| Aldehydes | Benzaldehyde | 25 mM | 28 | No Improvement |
| Aldehydes | Benzaldehyde | 50 mM | 53 | No Improvement |
| Aldehydes | Butyraldehyde | 10 mM | 47 | No Improvement |
| Aldehydes | Butyraldehyde | 25 mM | 34 | No Improvement |
| Aldehydes | Butyraldehyde | 50 mM | 30 | No Improvement |
| Aldehydes | Cinnamaldehyde | 10 mM | 25 | No Improvement |
| Aldehydes | Cinnamaldehyde | 25 mM | 32 | No Improvement |
| Aldehydes | Cinnamaldehyde | 50 mM | 21 | No Improvement |
| Aldehydes | Formamide | 10 mM | 62 | No Improvement |
| Aldehydes | Formamide | 25 mM | 62 | No Improvement |
| Aldehydes | Formamide | 50 mM | 62 | No Improvement |
| Aldehydes | Furfural | 10 mM | 58 | No Improvement |
| Aldehydes | Furfural | 25 mM | 37 | No Improvement |
| Aldehydes | Furfural | 50 mM | 38 | No Improvement |
| Aldehydes | D-(+)-Glyceraldehyde | 10 mM | 61 | No Improvement |
| Aldehydes | D-(+)-Glyceraldehyde | 25 mM | 33 | No Improvement |
| Aldehydes | D-(+)-Glyceraldehyde | 50 mM | 16 | No Improvement |
| Aldehydes | Glycolaldehyde Dimer | 10 mM | 37 | No Improvement |
| Aldehydes | Glycolaldehyde Dimer | 25 mM | 11 | No Improvement |
| Aldehydes | Glycolaldehyde Dimer | 50 mM | 2 | No Improvement |
| Aldehydes | 4-Isobutylbenzaldehyde | 10 mM | 57 | No Improvement |
| Aldehydes | 4-Isobutylbenzaldehyde | 25 mM | 44 | No Improvement |
| Aldehydes | 4-Isobutylbenzaldehyde | 50 mM | 48 | No Improvement |
| Aldehydes | p-Tolualdehyde | 10 mM | 51 | No Improvement |
| Aldehydes | p-Tolualdehyde | 25 mM | 35 | No Improvement |
| Aldehydes | p-Tolualdehyde | 50 mM | 71 | No Improvement |
| Aldehydes | Vanillin | 10 mM | 40 | No Improvement |
| Aldehydes | Vanillin | 25 mM | 32 | No Improvement |
| Aldehydes | Vanillin | 50 mM | 34 | No Improvement |
| Aldehydes | Acetaldehyde | 0.01 mM | 55 | No Improvement |
| Aldehydes | Acetaldehyde | 0.1 mM | 62 | No Improvement |
| Aldehydes | Acetaldehyde | 1 mM | 66 | No Improvement |
| Aldehydes | Acetaldehyde | 10 mM | 56 | No Improvement |
| Aldehydes | Acetaldehyde | 25 mM | 48 | No Improvement |
| Aldehydes | Acetaldehyde | 50 mM | 43 | No Improvement |
| Aldehydes | Benzaldehyde | 0.01 mM | 55 | No Improvement |
| Aldehydes | Benzaldehyde | 0.1 mM | 50 | No Improvement |
| Aldehydes | Benzaldehyde | 1 mM | 19 | No Improvement |
| Aldehydes | Benzaldehyde | 10 mM | 46 | No Improvement |
| Aldehydes | Benzaldehyde | 25 mM | 28 | No Improvement |
| Aldehydes | Benzaldehyde | 50 mM | 53 | No Improvement |
| Aldehydes | Butyraldehyde | 0.01 mM | 60 | No Improvement |
| Aldehydes | Butyraldehyde | 0.1 mM | 57 | No Improvement |
| Aldehydes | Butyraldehyde | 1 mM | 29 | No Improvement |
| Aldehydes | Butyraldehyde | 10 mM | 47 | No Improvement |
| Aldehydes | Butyraldehyde | 25 mM | 34 | No Improvement |
| Aldehydes | Butyraldehyde | 50 mM | 30 | No Improvement |
| Aldehydes | Cinnamaldehyde | 0.01 mM | 49 | No Improvement |
| Aldehydes | Cinnamaldehyde | 0.1 mM | 53 | No Improvement |

APPENDIX B (continued)

| Compound aassification | Additive | Additive Concentration | % Hb Recovery | Results |
|---|---|---|---|---|
| Aldehydes | Cinnamaldehyde | 1 mM | 25 | No Improvement |
| Aldehydes | Cinnamaldehyde | 10 mM | 25 | No Improvement |
| Aldehydes | Cinnamaldehyde | 25 mM | 32 | No Improvement |
| Aldehydes | Cinnamaldehyde | 50 mM | 21 | No Improvement |
| Aldehydes | D-(+)-Glyceraldehyde | 0.01 mM | 66 | No Improvement |
| Aldehydes | D-(+)-Glyceraldehyde | 0.1 mM | 60 | No Improvement |
| Aldehydes | D-(+)-Glyceraldehyde | 1 mM | 30 | No Improvement |
| Aldehydes | D-(+)-Glyceraldehyde | 10 mM | 61 | No Improvement |
| Aldehydes | D-(+)-Glyceraldehyde | 25 mM | 33 | No Improvement |
| Aldehydes | D-(+)-Glyceraldehyde | 50 mM | 16 | No Improvement |
| Aldehydes | Glycolaldehyde Dimer | 0.01 mM | 61 | No Improvement |
| Aldehydes | Glycolaldehyde Dimer | 0.1 mM | 68 | No Improvement |
| Aldehydes | Glycolaldehyde Dimer | 1 mM | 50 | No Improvement |
| Aldehydes | Glycolaldehyde Dimer | 10 mM | 37 | No Improvement |
| Aldehydes | Glycolaldehyde Dimer | 25 mM | 11 | No Improvement |
| Aldehydes | Glycolaldehyde Dimer | 50 mM | 2 | No Improvement |
| Aldehydes | Formamide | 0.01 mM | 58 | No Improvement |
| Aldehydes | Formamide | 0.1 mM | 67 | No Improvement |
| Aldehydes | Formamide | 1 mM | 69 | No Improvement |
| Aldehydes | Formamide | 10 mM | 62 | No Improvement |
| Aldehydes | Formamide | 25 mM | 62 | No Improvement |
| Aldehydes | Formamide | 50 mM | 62 | No Improvement |
| Aldehydes | Furfural | 0.01 mM | 63 | No Improvement |
| Aldehydes | Furfural | 0.1 mM | 65 | No Improvement |
| Aldehydes | Furfural | 1 mM | 34 | No Improvement |
| Aldehydes | Furfural | 10 mM | 58 | No Improvement |
| Aldehydes | Furfural | 25 mM | 37 | No Improvement |
| Aldehydes | Furfural | 50 mM | 38 | No Improvement |
| Aldehydes | 4-Isobutylbenzaldehyde | 0.01 mM | 69 | No Improvement |
| Aldehydes | 4-Isobutylbenzaldehyde | 0.1 mM | 61 | No Improvement |
| Aldehydes | 4-sobutylbenzaldehyde | 1 mM | 31 | No Improvement |
| Aldehydes | 4-Isobutylbenzaldehyde | 10 mM | 57 | No Improvement |
| Aldehydes | 4-Isobutylbenzaldehyde | 25 mM | 44 | No Improvement |
| Aldehydes | 4-Isobutylbenzaldehyde | 50 mM | 48 | No Improvement |
| Aldehydes | p-Tolualdehyde | 0.01 mM | 65 | No Improvement |
| Aldehydes | p-Tolualdehyde | 0.1 mM | 62 | No Improvement |
| Aldehydes | p-Tolualdehyde | 1 mM | 35 | No Improvement |
| Aldehydes | p-Tolualdehyde | 10 mM | 51 | No Improvement |
| Aldehydes | p-Tolualdehyde | 25 mM | 35 | No Improvement |
| Aldehydes | p-Tolualdehyde | 50 mM | 71 | No Improvement |
| Aldehydes | Vanillin | 0.01 mM | 66 | No Improvement |
| Aldehydes | Vanillin | 0.1 mM | 58 | No Improvement |
| Aldehydes | Vanillin | 1 mM | 32 | No Improvement |
| Aldehydes | Vanillin | 10 mM | 40 | No Improvement |
| Aldehydes | Vanillin | 25 mM | 32 | No Improvement |
| Aldehydes | Vanillin | 50 mM | 34 | No Improvement |
| HRP Stabilizer Components | HRP Conjugate Stabilizer (PN 85R-102) | 5% | 78 | Improvement in % Hb Recovery |
| HRP Stabilizer Components | HRP Conjugate Stabilizer (PN 85R-102) | 10% | 80 | Improvement in % Hb Recovery |
| HRP Stabilizer Components | HRP Conjugate Stabilizer (PN 85R-102) | 25% | 77 | Improvement in % Hb Recovery |
| Formaldehyde Releaser | Bronidox | 5 mM | 47 | No Improvement |
| Formaldehyde Releaser | Bronidox | 10 mM | 27 | No Improvement |
| Formaldehyde Releaser | Bronidox | 25 mM | 37 | No Improvement |
| Formaldehyde Releaser | Bronopol | 5 mM | 34 | No Improvement |
| Formaldehyde Releaser | Bronopol | 10 mM | 31 | No Improvement |
| Formaldehyde Releaser | Bronopol | 25 mM | 24 | No Improvement |
| Preservatives/Parabens | Benzyl 4-hydroxybenzoate | 5 mM | 63 | No Improvement |
| Preservatives/Parabens | Benzyl 4-hydroxybenzoate | 10 mM | 35 | No Improvement |
| Preservatives/Parabens | Benzyl 4-hydroxybenzoate | 25 mM | 26 | No Improvement |
| Preservatives/Parabens | Ethyl 4-hydroxybenzoate | 5 mM | 54 | No Improvement |
| Preservatives/Parabens | Ethyl 4-hydroxybenzoate | 10 mM | 43 | No Improvement |
| Preservatives/Parabens | Ethyl 4-hydroxybenzoate | 25 mM | 30 | No Improvement |
| Preservatives/Parabens | Methyl 4-hydroxybenzoate | 5 mM | 58 | No Improvement |
| Preservatives/Parabens | Methyl 4-hydroxybenzoate | 10 mM | 44 | No Improvement |
| Preservatives/Parabens | Methyl 4-hydroxybenzoate | 25 mM | 34 | No Improvement |
| Preservatives/Parabens | Propyl 4-hydroxybenzoate | 5 mM | 55 | No Improvement |
| Preservatives/Parabens | Propyl 4-hydroxybenzoate | 10 mM | 37 | No Improvement |
| Preservatives/Parabens | Propyl 4-hydroxybenzoate | 25 mM | 28 | No Improvement |
| HRP Stabilizer Components | HRP Conjugate Stabilizer (PN 85R-102) | 1% | 69 | Improvement in % Hb Recovery |
| HRP Stabilizer Components | HRP Conjugate Stabilizer (PN 85R-102) | 5% | 79 | Improvement in % Hb Recovery |

APPENDIX B

| Compound aassification | Additive | Additive Concentration | % Hb Recovery | Results |
|---|---|---|---|---|
| HRP Stabilizer Components | HRP Conjugate Stabilizer (PN 85R-102) | 10% | 76 | Improvement in % Hb Recovery |
| HRP Stabilizer Components | HRP Conjugate Stabilizer (PN 85R-102) | 15% | 81 | Improvement in % Hb Recovery |
| HRP Stabilizer Components | HRP Conjugate Stabilizer (PN 85R-102) | 20% | 75 | Improvement in % Hb Recovery |
| HRP Stabilizer Components | HRP Conjugate Stabilizer (PN 85R-102) | 25% | 76 | Improvement in % Hb Recovery |
| HRP Stabilizer Components | HRP Conjugate Stabilizer (PN 85R-102) | 30% | 70 | Improvement in % Hb Recovery |
| HRP Stabilizer Components | HRP Conjugate Stabilizer (PN 85R-102) | 40% | 71 | Improvement in % Hb Recovery |
| Polyvalent Ions/Metal Salts | Aluminum Chloride | 2.5 mM | 69 | No Improvement |
| Polyvalent Ions/Metal Salts | Aluminum Chloride | 5 mM | 70 | No Improvement |
| Polyvalent Ions/Metal Salts | Aluminum Chloride | 10 mM | 29 | No Improvement |
| Formaldehyde Releaser | Quaternium 15 | 5 mM | 52 | No Improvement |
| Formaldehyde Releaser | Quaternium 15 | 10 mM | 47 | No Improvement |
| Formaldehyde Releaser | Quaternium 15 | 20 mM | 50 | No Improvement |
| Preservatives | Sodium Nitrate | 5 mM | 70 | No Improvement |
| Preservatives | Sodium Nitrate | 10 mM | 65 | No Improvement |
| Preservatives | Sodium Nitrate | 20 mM | 56 | No Improvement |
| Preservatives | Sodium Nitrite | 5 mM | 64 | No Improvement |
| Preservatives | Sodium Nitrite | 10 mM | 65 | No Improvement |
| Preservatives | Sodium Nitrite | 20 mM | 62 | No Improvement |
| Substrates | Styrene Glycol | 5 mM | 56 | No Improvement |
| Substrates | Styrene Glycol | 10 mM | 58 | No Improvement |
| Substrates | Styrene Glycol | 20 mM | 48 | No Improvement |
| Substrates | Styrene Oxide | 5 mM | 57 | No Improvement |
| Substrates | Styrene Oxide | 10 mM | 42 | No Improvement |
| Substrates | Styrene Oxide | 20 mM | 31 | No Improvement |
| Enzyme Inhibitor | aurintircarboxylic acid ammonium salt | 0.1 mM | 52 | No Improvement |
| Enzyme Inhibitor | aurintircarboxylic acid ammonium salt | 1 mM | 63 | No Improvement |
| Enzyme Inhibitor | aurintircarboxylic acid ammonium salt | 10 mM | 35 | No Improvement |
| Polyvalent Ions/Metal Salts | Sodium Citrate | 0.1 mM | 61 | No Improvement |
| Polyvalent Ions/Metal Salts | Sodium Citrate | 1 mM | 60 | No Improvement |
| Polyvalent Ions/Metal Salts | Sodium Citrate | 10 mM | 55 | No Improvement |
| Vitamins | Vitamin B2 | 0.002 mM | 58 | No Improvement |
| Vitamins | Vitamin B2 | 0.02 mM | 48 | No Improvement |
| Vitamins | Vitamin B2 | 0.2 mM | 45 | No Improvement |
| Vitamins | Vitamin B3 | 0.1 mM | 53 | No Improvement |
| Vitamins | Vitamin B3 | 1 mM | 58 | No Improvement |
| Vitamins | Vitamin B3 | 10 mM | 42 | No Improvement |
| Vitamins | Vitamin B4 | 0.1 mM | 54 | No Improvement |
| Vitamins | Vitamin B4 | 1 mM | 57 | No Improvement |
| Vitamins | Vitamin B4 | 10 mM | 27 | No Improvement |
| Vitamins | Vitamin B9 | 0.1 mM | 58 | No Improvement |
| Vitamins | Vitamin B9 | 1 mM | 43 | No Improvement |
| Vitamins | Vitamin B9 | 10 mM | 37 | No Improvement |
| Vitamins | NAD + | 0.05 mM | 59 | No Improvement |
| Vitamins | NAD + | 0.5 mM | 54 | No Improvement |
| Vitamins | NAD + | 5 mM | 57 | No Improvement |
| Vitamins | NADH | 0.1 mM | 63 | No Improvement |
| Vitamins | NADH | 1 mM | 66 | No Improvement |
| Vitamins | NADH | 10 mM | 65 | No Improvement |
| Vitamins | Vitamin B12 | 0.01 mM | 53 | No Improvement |
| Vitamins | Vitamin B12 | 0.1 mM | 62 | No Improvement |
| Vitamins | Vitamin B12 | 1 mM | 59 | No Improvement |
| Vitamins | Vitamin B6 | 0.1 mM | 55 | No Improvement |
| Vitamins | Vitamin B6 | 1 mM | 53 | No Improvement |
| Vitamins | Vitamin B6 | 10 mM | 58 | No Improvement |
| HRP Stabilizer Components | HRP Conjugate Stabilizer (PN 85R-102) | 10% | 77 | Improvement in % Hb Recovery |
| HRP Stabilizer Components | HRP Conjugate Stabilizer (PN 85R-102) | 15% | 74 | Improvement in % Hb Recovery |
| HRP Stabilizer Components | HRP Conjugate Stabilizer (PN 85R-102) | 20% | 78 | Improvement in % Hb Recovery |
| HRP Stabilizer Components | HRP Conjugate Stabilizer (PN 85R-102) | 25% | 74 | Improvement in % Hb Recovery |
| Formaldehyde Releaser | BSA, Bronidox, Methylisothiazolone, Proclin 300 (10 mM MOPS) | 10% | 67 | No Improvement |
| Formaldehyde Releaser | BSA, Bronidox, Methylisothiazolone, Proclin 300 (10 mM MOPS) | 15% | 62 | No Improvement |
| Formaldehyde Releaser | BSA, Bronidox, Methylisothiazolone, Proclin 300 (10 mM MOPS) | 20% | 66 | No Improvement |

APPENDIX B

| Compound aassification | Additive | Additive Concentration | % Hb Recovery | Results |
|---|---|---|---|---|
| Formaldehyde Releaser | BSA, Bronidox, Methylisothiazolone, Proclin 300 (10 mM MOPS) | 25% | 61 | No Improvement |
| Formaldehyde Releaser | Bronidox, Methylisothiazolone, Prolin 300 (10 mM MOPS) | 0.002%, 0.002%, 0.0002% | 64 | No Improvement |
| Formaldehyde Releaser | Bronidox, Methylisothiazolone, Prolin 300 (10 mM MOPS) | 0.003%, 0.003%, 0.0003% | 57 | No Improvement |
| Formaldehyde Releaser | Bronidox, Methylisothiazolone, Prolin 300 (10 mM MOPS) | 0.004%, 0.004%, 0.0004% | 52 | No Improvement |
| Formaldehyde Releaser | Bronidox, Methylisothiazolone, Prolin 300 (10 mM MOPS) | 0.005%, 0.005%, 0.0005% | 45 | No Improvement |
| Formaldehyde Releaser | Bronidox, Methylisothiazolone (10 mM MOPS) | 0.002%, 0.002% | 64 | No Improvement |
| Formaldehyde Releaser | Bronidox, Methylisothiazolone (10 mM MOPS) | 0.003%, 0.003% | 58 | No Improvement |
| Formaldehyde Releaser | Bronidox, Methylisothiazolone (10 mM MOPS) | 0.004%, 0.004% | 56 | No Improvement |
| Formaldehyde Releaser | Bronidox, Methylisothiazolone (10 mM MOPS) | 0.005%, 0.005% | 53 | No Improvement |
| HRP Stabilizer Components | HRP Conjugate Stabilizer (PN 85R-102) | 10% | 75 | Improvement in % Hb Recovery |
| HRP Stabilizer Components | HRP Conjugate Stabilizer (PN 85R-102) | 15% | 72 | Improvement in % Hb Recovery |
| HRP Stabilizer Components | HRP Conjugate Stabilizer (PN 85R-102) | 20% | 75 | Improvement in % Hb Recovery |
| HRP Stabilizer Components | HRP Conjugate Stabilizer (PN 85R-102) | 25% | 63 | Improvement in % Hb Recovery |
| Formaldehyde Releaser | Bronidox | 0.002% | 67 | No Improvement |
| Formaldehyde Releaser | Bronidox | 0.003% | 65 | No Improvement |
| Formaldehyde Releaser | Bronidox | 0.004% | 69 | No Improvement |
| Formaldehyde Releaser | Bronidox | 0.005% | 65 | No Improvement |
| Enzyme Inhibitor | Methylisothiazolone | 0.002% | 54 | No Improvement |
| Enzyme Inhibitor | Methylisothiazolone | 0.003% | 58 | No Improvement |
| Enzyme Inhibitor | Methylisothiazolone | 0.004% | 56 | No Improvement |
| Enzyme Inhibitor | Methylisothiazolone | 0.005% | 47 | No Improvement |
| HRP Stabilizer Components | Proclin 300 | 0.0002% | 68 | No Improvement |
| HRP Stabilizer Components | Proclin 300 | 0.0003% | 68 | No Improvement |
| HRP Stabilizer Components | Proclin 300 | 0.0004% | 69 | No Improvement |
| HRP Stabilizer Components | Proclin 300 | 0.0005% | 63 | No Improvement |
| HRP Stabilizer Components | HRP Conjugate Stabilizer (PN 85R-102) | 10% | 81 | Improvement in % Hb Recovery |
| HRP Stabilizer Components | HRP Conjugate Stabilizer (PN 85R-102) | 15% | 74 | Improvement in % Hb Recovery |
| HRP Stabilizer Components | HRP Conjugate Stabilizer (PN 85R-102) | 20% | 70 | Improvement in % Hb Recovery |
| Formaldehyde Releaser | BSA, Bronidox, Methylisothiazolone, Proclin 300 (10 mM MOPS) | 10% (1%, 0.02%, 0.02%, 0.002%) | 47 | No Improvement |
| Formaldehyde Releaser | BSA, Bronidox, Methylisothiazolone, Proclin 300 (10 mM MOPS) | 15% (1%, 0.02%, 0.02%, 0.002%) | 43 | No Improvement |
| Formaldehyde Releaser | BSA, Bronidox, Methylisothiazolone, Proclin 300 (10 mM MOPS) | 20% (1%, 0.02%, 0.02%, 0.002%) | 39 | No Improvement |
| Formaldehyde Releaser | Bronidox, Methylisothiazolone, Prolin 300 (10mM MOPS) | 10% (0.02%, 0.02%, 0.002%) | 52 | No Improvement |
| Formaldehyde Releaser | Bronidox, Methylisothiazolone, Prolin 300 (10mM MOPS) | 15% (0.02%, 0.02%, 0.002%) | 42 | No Improvement |
| Formaldehyde Releaser | Bronidox, Methylisothiazolone, Prolin 300 (10mM MOPS) | 20% (0.02%, 0.02%, 0.002%) | 37 | No Improvement |
| Formaldehyde Releaser | Bronidox, Methylisothiazolone, Prolin 300 | 10% (0.02%, 0.02%, 0.002%) | 56 | No Improvement |
| Formaldehyde Releaser | Bronidox, Methylisothiazolone, Prolin 300 | 15% (0.02%, 0.02%, 0.002%) | 41 | No Improvement |
| Formaldehyde Releaser | Bronidox, Methylisothiazolone, Prolin 300 | 20% (0.02%, 0.02%, 0.002%) | 45 | No Improvement |
| Plasma | BSA (10 mM MOPS) | 1% | 76 | No Improvement |
| Polyvalent Ions/Metal Salts | Calcium Chloride | 10 mM | 75 | Calcium cation shows improvement in % Hb Recovery at 10 mM |
| Polyvalent Ions/Metal Salts | Magnesium Sulfate | 10 mM | 73 | Magnesium Cation shows improvement in % Hb Recovery around 10 mM |
| HRP Stabilizer Components | HRP Conjugate Stabilizer (PN ab171537) | 15% | 76 | Improvement in % Hb Recovery |
| HRP Stabilizer Components | HRP Conjugate Stabilizer (PN ab171537) + Calcium Chloride | 15% + 10 mM | 87 | Improvement in % Hb Recovery |

APPENDIX B

| Compound aassification | Additive | Additive Concentration | % Hb Recovery | Results |
| --- | --- | --- | --- | --- |
| HRP Stabilizer Components | HRP Conjugate Stabilizer (PN ab171537) + Magnesium Sulfate | 15% + 10 mM | 89 | Improvement in % Hb Recovery |
| HRP Stabilizer Components | HRP Conjugate Stabilizer (PN ab171537) + RD Hb Collection Buffer | 15% + 4% | 76 | Improvement in % Hb Recovery |
| HRP Stabilizer Components | HRP Conjugate Stabilizer (PN SZ02) | 15% | 75 | Improvement in % Hb Recovery |
| HRP Stabilizer Components | HRP Conjugate Stabilizer (PN SZ02) Calcium Chloride | 15% + 10 mM | 87 | Improvement in % Hb Recovery |
| HRP Stabilizer Components | HRPConjugate Stabilizer (PN SZ02) Magnesium Sulfate | 15% + 10 mM | 92 | Improvement in % Hb Recovery |
| HRP Stabilizer Components | HRP Conjugate Stabilizer (PN SZ02) + RD Hb Collection Buffer | 15% + 4% | 77 | Improvement in % Hb Recovery |
| HRP Stabilizer Components | HRP Conjugate Stabilizer (PN 85R-102) | 15% | 77 | Improvement in % Hb Recovery |
| HRP Stabilizer Components | HRP Conjugate Stabilizer (PN 85R-102) + Calcium Chloride | 15% + 10 mM | 92 | Improvement in % Hb Recovery |
| HRP Stabilizer Components | HRP Conjugate Stabilizer (PN 85R-102) + Magnesium Sulfate | 15% + 10 mM | 95 | Improvement in % Hb Recovery |
| HRP Stabilizer Components | HRP Conjugate Stabilizer (PN 85R-102) + RD Hb Collection Buffer | 15% + 4% | 77 | Improvement in % Hb Recovery |
| HRP Stabilizer Components | DEAE Dextran, Ethylene Glycol, Calcium Chloride | 0.5%, 10%, 10 mM | 63 | No Improvement |
| HRP Stabilizer Components | L.s. Dextran, Ethylene Glycol, Calcium Chloride | 0.5%, 10%, 10 mM | 52 | No Improvement |
| Sugars/Saccharides | Sucrose | 0.5M | 77 | Slight Improvement with Sugars. Needs further assay optimization |
| Sugars/Saccharides | Sucrose | 1M | 91 | Slight Improvement with Sugars. Needs further assay optimization |
| Sugars/Saccharides | Sucrose | 2M | 129 | Slight Improvement with Sugars. Needs further assay optimization |
| Sugars/Saccharides | Raffinose | 0.125M | 71 | Slight Improvement with Sugars. Needs further assay optimization |
| Sugars/Saccharides | Raffinose | 0.25M | 74 | Slight Improvement with Sugars. Needs further assay optimization |
| Sugars/Saccharides | Raffinose | 0.5M | 87 | Slight Improvement with Sugars. Needs further assay optimization |
| Sugars/Saccharides | Sucrose + Glucose | 0.25M + 0.25M | 78 | Slight Improvement with Sugars. Needs further assay optimization |
| Sugars/Saccharides | Sucrose + Glucose | 0.5M + 0.5M | 93 | Slight Improvement with Sugars. Needs further assay optimization |
| Sugars/Saccharides | Sucrose + Glucose | 1M + 1M | 100 | Slight Improvement with Sugars. Needs further assay optimization |
| Sugars/Saccharides | Sucrose + Trehalose | 0.25M + 0.125M | 74 | Slight Improvement with Sugars. Needs further assay optimization |
| Sugars/Saccharides | Sucrose + Trehalose | 0.5M + 0.25M | 75 | Slight Improvement with Sugars. Needs further assay optimization |
| Sugars/Saccharides | Sucrose + Trehalose | 1M + 0.5M | 141 | Slight Improvement with Sugars. Needs further assay optimization |
| Sugars/Saccharides | Sucrose + Raffinose | 0.25M + 0.0625M | 72 | Slight Improvement with Sugars. Needs further assay optimization |
| Sugars/Saccharides | Sucrose + Raffinose | 0.5M + 0.125M | 85 | Slight Improvement with Sugars. Needs further assay optimization |
| Sugars/Saccharides | Sucrose + Raffinose | 1M + 0.25M | 104 | Slight Improvement with Sugars. Needs further assay optimization |
| Sugars/Saccharides | Raffinose + Trehalose | 0.0625M + 0.125M | 71 | Slight Improvement with Sugars. Needs further assay optimization |

APPENDIX B

| Compound aassification | Additive | Additive Concentration | % Hb Recovery | Results |
| --- | --- | --- | --- | --- |
| Sugars/Saccharides | Raffinose + Trehalose | 0.125M + 0.25M | 88 | Slight Improvement with Sugars. Needs further assay optimization |
| Sugars/Saccharides | Raffinose + Trehalose | 0.25M + 0.5M | 79 | Slight Improvement with Sugars. Needs further assay optimization |
| Sugars/Saccharides | Raffinose + Glucose | 0.0625M + 0.25M | 70 | Slight Improvement with Sugars. Needs further assay optimization |
| Sugars/Saccharides | Raffinose + Glucose | 0.125M + 0.5M | 77 | Slight Improvement with Sugars. Needs further assay optimization |
| Sugars/Saccharides | Raffinose + Glucose | 0.25M + 1M | 90 | Slight Improvement with Sugars. Needs further assay optimization |
| Enzyme Inhibitor | aurintircarboxylic acid ammonium salt | 5% | 66 | No improvement |
| Enzyme Inhibitor | aurintircarboxylic acid ammonium salt | 10% | 61 | No improvement |
| Enzyme Inhibitor | aurintircarboxylic acid ammonium salt | 25% | 59 | No improvement |
| Sugars/Saccharides | Raffinose | 0.05M | 69 | Slight Improvement with Sugars. Needs further assay optimization |
| Sugars/Saccharides | Raffinose | 0.1M | 71 | Slight Improvement with Sugars. Needs further assay optimization |
| Sugars/Saccharides | Raffinose | 0.15M | 73 | Slight Improvement with Sugars. Needs further assay optimization |
| Sugars/Saccharides | Raffinose | 0.2M | 80 | Slight Improvement with Sugars. Needs further assay optimization |
| Sugars/Saccharides | Raffinose | 0.25M | 73 | Slight Improvement with Sugars. Needs further assay optimization |
| Sugars/Saccharides | Raffinose | 0.3M | 76 | Slight Improvement with Sugars. Needs further assay optimization |
| Sugars/Saccharides | Raffinose | 0.35M | 80 | Slight Improvement with Sugars. Needs further assay optimization |
| Sugars/Saccharides | Raffinose | 0.4M | 89 | Slight Improvement with Sugars. Needs further assay optimization |
| Sugars/Saccharides | Raffinose | 0.45M | 69 | Slight Improvement with Sugars. Needs further assay optimization |
| Sugars/Saccharides | Raffinose | 0.5M | 91 | Slight Improvement with Sugars. Needs further assay optimization |
| Sugars/Saccharides | Sucrose | 0.03M | 67 | Slight Improvement with Sugars. Needs further assay optimization |
| Sugars/Saccharides | Sucrose | 0.06M | 72 | Slight Improvement with Sugars. Needs further assay optimization |
| Sugars/Saccharides | Sucrose | 0.09M | 68 | Slight Improvement with Sugars. Needs further assay optimization |
| Sugars/Saccharides | Sucrose | 0.12M | 74 | Slight Improvement with Sugars. Needs further assay optimization |
| Sugars/Saccharides | Sucrose | 0.15M | 75 | Slight Improvement with Sugars. Needs further assay optimization |
| Sugars/Saccharides | Sucrose | 0.18M | 79 | Slight Improvement with Sugars. Needs further assay optimization |
| Sugars/Saccharides | Sucrose | 0.21M | 73 | Slight Improvement with Sugars. Needs further assay optimization |
| Sugars/Saccharides | Sucrose | 0.24M | 82 | Slight Improvement with Sugars. Needs further assay optimization |

APPENDIX B -continued

| Compound aassification | Additive | Additive Concentration | % Hb Recovery | Results |
|---|---|---|---|---|
| Sugars/Saccharides | Sucrose | 0.27M | 79 | Slight Improvement with Sugars. Needs further assay optimization |
| Sugars/Saccharides | Sucrose | 0.3M | 85 | Slight Improvement with Sugars. Needs further assay optimization |
| Sugars/Saccharides | Raffinose | 0.2M | 76 | Slight Improvement with Sugars. Needs further assay optimization |
| Sugars/Saccharides | Raffinose + Betaine | 0.2M + 0.125M | 83 | Slight Improvement with Sugars. Needs further assay optimization |
| Sugars/Saccharides | Raffinose + Betaine | 0.2M + 0.25M | 80 | Slight Improvement with Sugars. Needs further assay optimization |
| Sugars/Saccharides | Raffinose + Betaine | 0.2M + 0.5M | 85 | Slight Improvement with Sugars. Needs further assay optimization |
| Sugars/Saccharides | Raffinose + Calcium Chloride | 0.2M + 1 mM | 88 | Slight Improvement with Sugars. Needs further assay optimization |
| Sugars/Saccharides | Raffinose + Calcium Chloride | 0.2M + 5 mM | 77 | Slight Improvement with Sugars. Needs further assay optimization |
| Sugars/Saccharides | Raffinose + Calcium Chloride | 0.2M + 10 mM | 90 | Slight Improvement with Sugars. Needs further assay optimization |
| Sugars/Saccharides | Raffinose + Ectoine | 0.2M + 75 mM | 88 | Slight Improvement with Sugars. Needs further assay optimization |
| Sugars/Saccharides | Raffinose + Ectoine | 0.2M + 150 mM | 81 | Slight Improvement with Sugars. Needs further assay optimization |
| Sugars/Saccharides | Raffinose + Ectoine | 0.2M + 300 mM | 79 | Slight Improvement with Sugars. Needs further assay optimization |
| Sugars/Saccharides | Raffinose + Magnesium Sulfate | 0.2M + 1 mM | 90 | Slight Improvement with Sugars. Needs further assay optimization |
| Sugars/Saccharides | Raffinose + Magnesium Sulfate | 0.2M + 5 mM | 91 | Slight Improvement with Sugars. Needs further assay optimization |
| Sugars/Saccharides | Raffinose + Magnesium Sulfate | 0.2M + 10 mM | 87 | Slight Improvement with Sugars. Needs further assay optimization |
| Sugars/Saccharides | Raffinose + TMANO | 0.2M + 0.125 M | 81 | Slight Improvement with Sugars. Needs further assay optimization |
| Sugars/Saccharides | Raffinose + TMANO | 0.2M + 0.25 M | 98 | Slight Improvement with Sugars. Needs further assay optimization |
| Sugars/Saccharides | Raffinose + TMANO | 0.2M + 0.5M | 84 | Slight Improvement with Sugars. Needs further assay optimization |
| Sugars/Saccharides | Sucrose | 0.24M | 61 | Slight Improvement with Sugars. Needs further assay optimization |
| Sugars/Saccharides | Sucrose + Betaine | 0.24M + 0.125M | 87 | Slight Improvement with Sugars. Needs further assay optimization |
| Sugars/Saccharides | Sucrose + Betaine | 0.24M + 0.245M | 84 | Slight Improvement with Sugars. Needs further assay optimization |
| Sugars/Saccharides | Sucrose + Betaine | 0.24M + 0.5M | 84 | Slight Improvement with Sugars. Needs further assay optimization |
| Sugars/Saccharides | Sucrose + Calcium Chloride | 0.24M + 1 mM | 83 | Slight Improvement with Sugars. Needs further assay optimization |
| Sugars/Saccharides | Sucrose + Calcium Chloride | 0.24M + 5 mM | 87 | Slight Improvement with Sugars. Needs further assay optimization |

APPENDIX B

| Compound aassification | Additive | Additive Concentration | % Hb Recovery | Results |
| --- | --- | --- | --- | --- |
| Sugars/Saccharides | Sucrose + Calcium Chloride | 0.24M + 10 mM | 94 | Slight Improvement with Sugars. Needs further assay optimization |
| Sugars/Saccharides | Sucrose + Ectoine | 0.24M + 75 mM | 84 | Slight Improvement with Sugars. Needs further assay optimization |
| Sugars/Saccharides | Sucrose + Ectoine | 0.24M + 150 mM | 85 | Slight Improvement with Sugars. Needs further assay optimization |
| Sugars/Saccharides | Sucrose + Ectoine | 0.24M + 300 mM | 79 | Slight Improvement with Sugars. Needs further assay optimization |
| Sugars/Saccharides | Sucrose + Magnesium Sulfate | 0.24M + 1 mM | 74 | Slight Improvement with Sugars. Needs further assay optimization |
| Sugars/Saccharides | Sucrose + Magnesium Sulfate | 0.24M + 5 mM | 89 | Slight Improvement with Sugars. Needs further assay optimization |
| Sugars/Saccharides | Sucrose + Magnesium Sulfate | 0.24M + 10 mM | 79 | Slight Improvement with Sugars. Needs further assay optimization |
| Sugars/Saccharides | Sucrose + TMANO | 0.24M + 0.125M | 77 | Slight Improvement with Sugars. Needs further assay optimization |
| Sugars/Saccharides | Sucrose + TMANO | 0.24M + 0.245M | 87 | Slight Improvement with Sugars. Needs further assay optimization |
| Sugars/Saccharides | Sucrose + TMANO | 0.24M + 0.5M | 79 | Slight Improvement with Sugars. Needs further assay optimization |
| HRP Stabilizer Components | Phenol Red | 0.01% | 70 | No improvement |
| HRP Stabilizer Components | Phenol Red | 0.03% | 71 | No improvement |
| HRP Stabilizer Components | Phenol Red | 0.05% | 70 | No improvement |
| HRP Stabilizer Components | Sodium Benzoate | 0.10% | 67 | No improvement |
| HRP Stabilizer Components | Sodium Benzoate | 0.50% | 60 | No improvement |
| HRP Stabilizer Components | Sodium Benzoate | 1% | 54 | No improvement |
| HRP Stabilizer Components | Fisher HRP Sol | 5% | 71 | No improvement |
| HRP Stabilizer Components | Fisher HRP Sol | 10% | 70 | No improvement |
| HRP Stabilizer Components | Fisher HRP Sol | 25% | 68 | No improvement |
| HRP Stabilizer Components | HRP Conjugate Stabilizer (PN SZ02) (comp) | 5% | 83 | Improvement in % Hb Recovery |
| HRP Stabilizer Components | HRP Conjugate Stabilizer (PN SZ02) (spike) | 5% | 71 | Improvement in % Hb Recovery |
| Formaldehyde Releaser | Bronidox | 0.0002% | 69 | No improvement |
| Formaldehyde Releaser | Bronidox | 0.0010% | 68 | No improvement |
| Formaldehyde Releaser | Bronidox | 0.0020% | 70 | No improvement |
| Enzyme Inhibitor | Methylisothiazolone | 0.0002% | 71 | No improvement |
| Enzyme Inhibitor | Methylisothiazolone | 0.0010% | 68 | No improvement |
| Enzyme Inhibitor | Methylisothiazolone | 0.0020% | 63 | No improvement |
| Flavoniods | 7,8 dihydroxyflavone | 0.25 mM | 51 | No improvement |
| Flavoniods | 7,8 dihydroxyflavone | 0.5 mM | 39 | No improvement |
| Flavoniods | 7,8 dihydroxyflavone | 1 mM | 38 | No improvement |
| Flavoniods | Quercetin | 150 uM | 45 | No improvement |
| Flavoniods | Quercetin | 300 uM | 38 | No improvement |
| Flavoniods | Quercetin | 600 uM | 35 | No improvement |
| Flavoniods | Diadzein | 25 uM | 68 | No improvement |
| Flavoniods | Diadzein | 50 uM | 78 | No improvement |
| Flavoniods | Diadzein | 100 uM | 68 | No improvement |
| Redox/antioxidants | Ascorbic Acid | 0.5 mM | 65 | No improvement |
| Redox/antioxidants | Ascorbic Acid | 1 mM | 67 | No improvement |
| Redox/antioxidants | Ascorbic Acid | 5 mM | 57 | No improvement |
| Enzyme Inhibitor | Methylisothiazolone | 0.00005% | 68 | No improvement |
| Enzyme Inhibitor | Methylisothiazolone | 0.0001% | 68 | No improvement |
| Enzyme Inhibitor | Methylisothiazolone | 0.0002% | 67 | No improvement |
| Preservatives | Sodium Benzoate | 0.03% | 69 | No improvement |
| Preservatives | Sodium Benzoate | 0.05% | 73 | No improvement |
| Preservatives | Sodium Benzoate | 0.10% | 65 | No improvement |
| Flavoniods | Diadzein | 40 mM | 66 | No improvement |
| Flavoniods | Diadzein | 50 mM | 65 | No improvement |
| Flavoniods | Diadzein | 60 mM | 66 | No improvement |
| Substrates | Resveratrol | 5 mM | 48 | No improvement |
| Substrates | Resveratrol | 10 mM | 40 | No improvement |
| Substrates | Resveratrol | 20 mM | 38 | No improvement |
| Preservatives | Sodium Benzoate | 0.04% | 67 | No improvement |

APPENDIX B

| Compound aassification | Additive | Additive Concentration | % Hb Recovery | Results |
|---|---|---|---|---|
| Preservatives | Sodium Benzoate | 0.05% | 68 | No improvement |
| Preservatives | Sodium Benzoate | 0.06% | 67 | No improvement |
| Vitamins | Tocopherol | 0.10% | 71 | No improvement |
| Vitamins | Tocopherol | 1% | 73 | No improvement |
| Vitamins | Tocopherol | 10% | 65 | No improvement |
| Vitamins | Vitamin B6 | 0.5 mM | 68 | No improvement |
| Vitamins | Vitamin B6 | 1 mM | 67 | No improvement |
| Vitamins | Vitamin B6 | 2 mM | 66 | No improvement |
| Vitamins | Vitamine B6 in HCl | 0.5 mM | 68 | No improvement |
| Vitamins | Vitamine B6 in HCl | 1 mM | 41 | No improvement |
| Vitamins | Vitamine B6 in HCl | 2 mM | 40 | No improvement |
| Plasma | Fetal Bovine Serum | 1% | 58 | No improvement |
| Plasma | Fetal Bovine Serum | 10% | 63 | No improvement |
| Plasma | Fetal Bovine Serum | 50% | 68 | No improvement |
| Plasma | Gamma Globulins | 10 mg/mL | 85 | No improvement |
| Plasma | Gamma Globulins | 25 mg/mL | 89 | No improvement |
| Plasma | Gamma Globulins | 50 mg/mL | 88 | No improvement |
| Sugars/Saccharides | Glucose | 0.2M | 71 | Slight Improvement with Sugars. Needs further assay optimization |
| Sugars/Saccharides | Glucose | 0.4M | 72 | Slight Improvement with Sugars. Needs further assay optimization |
| Sugars/Saccharides | Glucose | 0.6M | 76 | Slight Improvement with Sugars. Needs further assay optimization |
| Sugars/Saccharides | Glucose | 0.8M | 73 | Slight Improvement with Sugars. Needs further assay optimization |
| Sugars/Saccharides | Glucose | 1.0M | 79 | Slight Improvement with Sugars. Needs further assay optimization |
| Sugars/Saccharides | Glucose | 1.2M | 78 | Slight Improvement with Sugars. Needs further assay optimization |
| Sugars/Saccharides | Glucose | 1.4M | 80 | Slight Improvement with Sugars. Needs further assay optimization |
| Sugars/Saccharides | Glucose | 1.6M | 76 | Slight Improvement with Sugars. Needs further assay optimization |
| Sugars/Saccharides | Glucose | 1.8M | 77 | Slight Improvement with Sugars. Needs further assay optimization |
| Sugars/Saccharides | Glucose | 2M | 79 | Slight Improvement with Sugars. Needs further assay optimization |
| Sugars/Saccharides | Trehalose | 0.1M | 72 | Slight Improvement with Sugars. Needs further assay optimization |
| Sugars/Saccharides | Trehalose | 0.2M | 74 | Slight Improvement with Sugars. Needs further assay optimization |
| Sugars/Saccharides | Trehalose | 0.3M | 78 | Slight Improvement with Sugars. Needs further assay optimization |
| Sugars/Saccharides | Trehalose | 0.4M | 77 | Slight Improvement with Sugars. Needs further assay optimization |
| Sugars/Saccharides | Trehalose | 0.5M | 82 | Slight Improvement with Sugars. Needs further assay optimization |
| Sugars/Saccharides | Trehalose | 0.6M | 82 | Slight Improvement with Sugars. Needs further assay optimization |
| Sugars/Saccharides | Trehalose | 0.7M | 83 | Slight Improvement with Sugars. Needs further assay optimization |
| Sugars/Saccharides | Trehalose | 0.8M | 82 | Slight Improvement with Sugars. Needs further assay optimization |
| Sugars/Saccharides | Trehalose | 0.9M | 85 | Slight Improvement with Sugars. Needs further assay optimization |

APPENDIX B -continued

| Compound aassification | Additive | Additive Concentration | % Hb Recovery | Results |
|---|---|---|---|---|
| Sugars/Saccharides | Trehalose | 1M | 86 | Slight Improvement with Sugars. Needs further assay optimization |
| Osmolytes | Betaine | 1M | 77 | Betaine shows improvement in % Hb Recovery at high concentrations |
| Osmolytes | Ectoine | 0.3M | 65 | No improvement |
| Polyvalent Ions/Metal Salts | Magnesium Sulfate | 10 mM | 78 | Magnesium Cation shows improvement in % Hb Recovery around 10 mM |
| Osmolytes | Trimethylamine N-oxide (TMANO) | 1M | 77 | Slight Improvement with Sugars. Needs further assay optimization |
| Sugars/Saccharides | Glucose | 0.6M | 74 | Slight Improvement with Sugars. Needs further assay optimization |
| Sugars/Saccharides | Glucose + Betaine | 0.6M + 0.125M | 74 | Slight Improvement with Sugars. Needs further assay optimization |
| Sugars/Saccharides | Glucose + Betaine | 0.6M + 0.25M | 71 | Slight Improvement with Sugars. Needs further assay optimization |
| Sugars/Saccharides | Glucose + Betaine | 0.6M + 0.5M | 77 | Slight Improvement with Sugars. Needs further assay optimization |
| Sugars/Saccharides | Glucose + Calcium Chloride | 0.6M + 1 mM | 71 | Slight Improvement with Sugars. Needs further assay optimization |
| Sugars/Saccharides | Glucose + Calcium Chloride | 0.6M + 5 mM | 73 | Slight Improvement with Sugars. Needs further assay optimization |
| Sugars/Saccharides | Glucose + Calcium Chloride | 0.6M + 10 mM | 84 | Slight Improvement with Sugars. Needs further assay optimization |
| Sugars/Saccharides | Glucose + Ectoine | 0.6M + 0.075M | 73 | Slight Improvement with Sugars. Needs further assay optimization |
| Sugars/Saccharides | Glucose + Ectoine | 0.6M + 0.15M | 72 | Slight Improvement with Sugars. Needs further assay optimization |
| Sugars/Saccharides | Glucose + Ectoine | 0.6M + 0.3M | 71 | Slight Improvement with Sugars. Needs further assay optimization |
| Sugars/Saccharides | Glucose + Magnesium Sulfate | 0.6M + 1 mM | 75 | Slight Improvement with Sugars. Needs further assay optimization |
| Sugars/Saccharides | Glucose + Magnesium Sulfate | 0.6M + 5 mM | 75 | Slight Improvement with Sugars. Needs further assay optimization |
| Sugars/Saccharides | Glucose + Magnesium Sulfate | 0.6M + 10 mM | 78 | Slight Improvement with Sugars. Needs further assay optimization |
| Sugars/Saccharides | Glucose + TMANO | 0.6M + 0.125M | 69 | Slight Improvement with Sugars. Needs further assay optimization |
| Sugars/Saccharides | Glucose + TMANO | 0.6M + 0.25M | 73 | Slight Improvement with Sugars. Needs further assay optimization |
| Sugars/Saccharides | Glucose + TMANO | 0.6M + 0.5M | 68 | Slight Improvement with Sugars. Needs further assay optimization |
| Sugars/Saccharides | Trehalose | 0.3M | 72 | Slight Improvement with Sugars. Needs further assay optimization |
| Sugars/Saccharides | Trehalose + Betaine | 0.3M + 0.125M | 73 | Slight Improvement with Sugars. Needs further assay optimization |
| Sugars/Saccharides | Trehalose + Betaine | 0.3M + 0.25M | 72 | Slight Improvement with Sugars. Needs further assay optimization |
| Sugars/Saccharides | Trehalose + Betaine | 0.3M + 0.5M | 81 | Slight Improvement with Sugars. Needs further assay optimization |

APPENDIX B

| Compound aassification | Additive | Additive Concentration | % Hb Recovery | Results |
| --- | --- | --- | --- | --- |
| Sugars/Saccharides | Trehalose + Calcium Chloride | 0.3M + 1 mM | 69 | Slight Improvement with Sugars. Needs further assay optimization |
| Sugars/Saccharides | Trehalose + Calcium Chloride | 0.3M + 5 mM | 68 | Slight Improvement with Sugars. Needs further assay optimization |
| Sugars/Saccharides | Trehalose + Calcium Chloride | 0.3M + 10 mM | 83 | Slight Improvement with Sugars. Needs further assay optimization |
| Sugars/Saccharides | Trehalose + Ectoine | 0.3M + 0.075M | 77 | Slight Improvement with Sugars. Needs further assay optimization |
| Sugars/Saccharides | Trehalose + Ectoine | 0.3M + 0.15M | 72 | Slight Improvement with Sugars. Needs further assay optimization |
| Sugars/Saccharides | Trehalose + Ectoine | 0.3M + 0.3M | 76 | Slight Improvement with Sugars. Needs further assay optimization |
| Sugars/Saccharides | Trehalose + Magnesium Sulfate | 0.3M + 1 mM | 68 | Slight Improvement with Sugars. Needs further assay optimization |
| Sugars/Saccharides | Trehalose + Magnesium Sulfate | 0.3M + 5 mM | 80 | Slight Improvement with Sugars. Needs further assay optimization |
| Sugars/Saccharides | Trehalose + Magnesium Sulfate | 0.3M + 10 mM | 76 | Slight Improvement with Sugars. Needs further assay optimization |
| Sugars/Saccharides | Trehalose + TMANO | 0.3M + 0.125M | 70 | Slight Improvement with Sugars. Needs further assay optimization |
| Sugars/Saccharides | Trehalose + TMANO | 0.3M + 0.25M | 79 | Slight Improvement with Sugars. Needs further assay optimization |
| Sugars/Saccharides | Trehalose + TMANO | 0.3M + 0.5M | 75 | Slight Improvement with Sugars. Needs further assay optimization |
| Sugars/Saccharides | Erlose | 1 mM | 72 | No improvement |
| Sugars/Saccharides | Erlose | 5 mM | 69 | No improvement |
| Sugars/Saccharides | Erlose | 10 mM | 76 | No improvement |
| Sugars/Saccharides | Fructose | 0.05M | 67 | No improvement |
| Sugars/Saccharides | Fructose | 0.1M | 69 | No improvement |
| Sugars/Saccharides | Fructose | 0.25M | 65 | No improvement |
| Sugars/Saccharides | Galactose | 0.1M | 71 | No improvement |
| Sugars/Saccharides | Galactose | 0.25M | 68 | No improvement |
| Sugars/Saccharides | Galactose | 0.5M | 76 | No improvement |
| Sugars/Saccharides | Kestose | 1 mM | 71 | No improvement |
| Sugars/Saccharides | Kestose | 5 mM | 68 | No improvement |
| Sugars/Saccharides | Kestose | 10 mM | 76 | No improvement |
| Sugars/Saccharides | Lactose | 0.025M | 66 | No Improvement |
| Sugars/Saccharides | Lactose | 0.05M | 71 | No Improvement |
| Sugars/Saccharides | Lactose | 0.1M | 65 | No Improvement |
| Sugars/Saccharides | Maltose | 0.1M | 72 | No Improvement |
| Sugars/Saccharides | Maltose | 0.25M | 69 | No Improvement |
| Sugars/Saccharides | Maltose | 0.5M | 76 | No Improvement |
| Sugars/Saccharides | Melezitose | 10 mM | 66 | No Improvement |
| Sugars/Saccharides | Melezitose | 50 mM | 71 | No Improvement |
| Sugars/Saccharides | Melezitose | 100 mM | 65 | No Improvement |
| Sugars/Saccharides | Stachyose | 1 mM | 67 | No Improvement |
| Sugars/Saccharides | Stachyose | 5 mM | 69 | No Improvement |
| Sugars/Saccharides | Stachyose | 7 mM | 65 | No Improvement |
| Formaldehyde Releaser | Diazolidinyl Urea, EDTA, Glycine | 1% (325 g/L, 90 g/L, 40 g/L) | 66 | No Improvement |
| Formaldehyde Releaser | Imidazolidinyl Urea, EDTA, Glycine | 1% (500 g/L, 90 g/L, 40 g/L) | 63 | No Improvement |
| Formaldehyde Releaser | Diazolidinyl Urea, Imidazolidinyl Urea, EDTA, Glycine | 1% (325 g/L, 500 g/L, 90 g/L, 40 g/L) | 62 | No Improvement |
| Formaldehyde Releaser | Diazolidinyl Urea, EDTA, Glycine | 5% (325 g/L, 90 g/L, 40 g/L) | 50 | No Improvement |
| Formaldehyde Releaser | Imidazolidinyl Urea, EDTA, Glycine | 5% (500 g/L, 90 g/L, 40 g/L) | 56 | No Improvement |
| Formaldehyde Releaser | Diazolidinyl Urea, Imidazolidinyl Urea, EDTA, Glycine | 5% (325 g/L, 500 g/L, 90 g/L, 40 g/L) | 48 | No Improvement |
| Formaldehyde Releaser | Diazolidinyl Urea, EDTA, Glycine | 10% (325 g/L, 90 g/L, 40 g/L) | 43 | No Improvement |
| Formaldehyde Releaser | Imidazolidinyl Urea, EDTA, Glycine | 10% (500 g/L, 90 g/L, 40 g/L) | 45 | No Improvement |
| Formaldehyde Releaser | Diazolidinyl Urea, Imidazolidinyl Urea, EDTA, Glycine | 10% (325 g/L, 500 g/L, 90 g/L, 40 g/L) | 35 | No Improvement |
| Formaldehyde Releaser | Diazolidinyl Urea, EDTA, Glycine | 1% (1.25%, 2.05%, 0.16%) | 64 | No Improvement |
| Formaldehyde Releaser | Imidazolidinyl Urea, EDTA, Glycine | 1% (2.10%, 2.05%, 0.16%) | 71 | No Improvement |

-continued

APPENDIX B

| Compound aassification | Additive | Additive Concentration | % Hb Recovery | Results |
|---|---|---|---|---|
| Formaldehyde Releaser | Diazolidinyl Urea, Imidazolidinyl Urea, EDTA, Glycine | 1% (1.25%, 2.10%, 2.05%, 0.16%) | 67 | No Improvement |
| Formaldehyde Releaser | Diazolidinyl Urea, EDTA, Glycine | 10% (1.25%, 2.05%, 0.16%) | 65 | No Improvement |
| Formaldehyde Releaser | Imidazolidinyl Urea, EDTA, Glycine | 10% (2.10%, 2.05%, 0.16%) | 65 | No Improvement |
| Formaldehyde Releaser | Diazolidinyl Urea, Imidazolidinyl Urea, EDTA, Glycine | 10% (1.25%, 2.10%, 2.05%, 0.16%) | 64 | No Improvement |
| Formaldehyde Releaser | Diazolidinyl Urea, EDTA, Glycine | 20% (1.25%, 2.05%, 0.16%) | 58 | No Improvement |
| Formaldehyde Releaser | Imidazolidinyl Urea, EDTA, Glycine | 20% (2.10%, 2.05%, 0.16%) | 63 | No Improvement |
| Formaldehyde Releaser | Diazolidinyl Urea, Imidazolidinyl Urea, EDTA, Glycine | 20% (1.25%, 2.10%, 2.05%, 0.16%) | 60 | NoImprovement |
| Formaldehyde Releaser | Diazolidinyl Urea | 400 g/L | 6 | No Improvement |
| Formaldehyde Releaser | Diazolidinyl Urea | 200 g/L | 20 | No Improvement |
| Formaldehyde Releaser | Diazolidinyl Urea | 100 g/L | 39 | No Improvement |
| Formaldehyde Releaser | Diazolidinyl Urea | 50 g/L | 55 | No Improvement |
| Formaldehyde Releaser | Diazolidinyl Urea | 25 g/L | 58 | No Improvement |
| Formaldehyde Releaser | Diazolidinyl Urea | 12.5 g/L | 62 | No Improvement |
| Formaldehyde Releaser | Imidazolidinyl Urea | 400 g/L | 14 | No Improvement |
| Formaldehyde Releaser | Imidazolidinyl Urea | 200 g/L | 32 | No Improvement |
| Formaldehyde Releaser | Imidazolidinyl Urea | 100 g/L | 45 | No Improvement |
| Formaldehyde Releaser | Imidazolidinyl Urea | 50 g/L | 55 | No Improvement |
| Formaldehyde Releaser | Imidazolidinyl Urea | 25 g/L | 57 | No Improvement |
| Formaldehyde Releaser | Imidazolidinyl Urea | 12.5 g/L | 65 | No Improvement |
| Formaldehyde Releaser | Diazolidinyl Urea, EDTA, Glycine | 10% (325 g/L, 90 g/L, 40 g/L) | 40 | No Improvement |
| Formaldehyde Releaser | Diazolidinyl Urea, EDTA, Glycine | 1% (325 g/L, 90 g/L, 40 g/L) | 67 | No Improvement |
| Formaldehyde Releaser | Imidazolidinyl Urea, EDTA, Glycine | 10% (500 g/L, 90 g/L, 40 g/L) | 51 | No Improvement |
| Formaldehyde Releaser | Imidazolidinyl Urea, EDTA, Glycine | 1% (500 g/L, 90g/L, 40 g/L) | 67 | No Improvement |
| Formaldehyde Releaser | Diazolidinyl Urea, Imidazolidinyl Urea, EDTA, Glycine | 10% (325 g/L, 500 g/L, 90 g/L, 40 g/L) | 42 | No Improvement |
| Formaldehyde Releaser | Diazolidinyl Urea, Imidazolidinyl Urea, EDTA, Glycine | 1% (325 g/L, 500 g/L, 90 g/L, 40 g/L) | 64 | No Improvement |
| Formaldehyde Releaser | Imidazolidinyl Urea, pH 6.5 (RT) | 0.1% | 66 | No Improvement |
| Formaldehyde Releaser | Imidazolidinyl Urea + Glycine, pH 6.5 (RT) | 0.1% + 0.1% | 67 | No Improvement |
| Formaldehyde Releaser | Imidazolidinyl Urea + Urea, pH 6.5 (RT) | 0.1% + 0.1% | 64 | No Improvement |
| Formaldehyde Releaser | Imidazolidinyl Urea + Ammonium Chloride, pH 6.5 (RT) | 0.1% + 0.1% | 67 | No Improvement |
| Formaldehyde Releaser | Imidazolidinyl Urea, pH 7.0 (RT) | 0.1% | 64 | No Improvement |
| Formaldehyde Releaser | Imidazolidinyl Urea + Glycine, pH 7.0 (RT) | 0.1% + 0.1% | 65 | No Improvement |
| Formaldehyde Releaser | Imidazolidinyl Urea + Urea, pH 7.0 (RT) | 0.1% + 0.1% | 66 | No Improvement |
| Formaldehyde Releaser | Imidazolidinyl Urea + Ammonium Chloride, pH 7.0 (RT) | 0.1% + 0.1% | 67 | No Improvement |
| Formaldehyde Releaser | Imidazolidinyl Urea, pH 7.5 (RT) | 0.1% | 64 | No Improvement |
| Formaldehyde Releaser | Imidazolidinyl Urea + Glycine, pH 7.5 (RT) | 0.1% + 0.1% | 66 | No Improvement |
| Formaldehyde Releaser | Imidazolidinyl Urea + Urea, pH 7.5 (RT) | 0.1% + 0.1% | 62 | No Improvement |
| Formaldehyde Releaser | Imidazolidinyl Urea + Ammonium Chloride, pH 7.5 (RT) | 0.1% + 0.1% | 67 | No Improvement |
| Formaldehyde Releaser | Diazolidinyl Urea, pH 6.5 (RT) | 0.1% | 65 | No Improvement |
| Formaldehyde Releaser | Diazolidinyl Urea + Glycine, pH 6.5 (RT) | 0.1% + 0.1% | 66 | No Improvement |
| Formaldehyde Releaser | Diazolidinyl Urea + Urea, pH 6.5 (RT) | 0.1% + 0.1% | 62 | No Improvement |
| Formaldehyde Releaser | Diazolidinyl Urea + Ammonium Chloride, pH 6.5 (RT) | 0.1% + 0.1% | 66 | No Improvement |
| Formaldehyde Releaser | Diazolidinyl Urea, pH 7.0 (RT) | 0.1% | 65 | No Improvement |
| Formaldehyde Releaser | Diazolidinyl Urea + Glycine, pH 7.0 (RT) | 0.1% + 0.1% | 66 | No Improvement |
| Formaldehyde Releaser | Diazolidinyl Urea + Urea, pH 7.0 (RT) | 0.1% + 0.1% | 64 | No Improvement |
| Formaldehyde Releaser | Diazolidinyl Urea + Ammonium Chloride, pH 7.0 (RT) | 0.1% + 0.1% | 66 | No Improvement |
| Formaldehyde Releaser | Diazolidinyl Urea, pH 7.5 (RT) | 0.1% | 65 | No Improvement |
| Formaldehyde Releaser | Diazolidinyl Urea + Glycine, pH 7.5 (RT) | 0.1% + 0.1% | 66 | No Improvement |
| Formaldehyde Releaser | Diazolidinyl Urea + Urea, pH 7.5 (RT) | 0.1% + 0.1% | 63 | No Improvement |
| Formaldehyde Releaser | Diazolidinyl Urea + Ammonium Chloride, pH 7.5 (RT) | 0.1% + 0.1% | 66 | No Improvement |
| Formaldehyde Releaser | 1-(cis-3-Chloroallyl)-3,5,7-triaza-1-azoniaadamantane chloride Urea, pH 6.5 (RT) | 0.1% | 59 | No Improvement |
| Formaldehyde Releaser | 1-(cis-3-Chloroallyl)-3,5,7-triaza-1-azoniaadamantane chloride Urea + Glycine, pH 6.5 (RT) | 0.1% + 0.1% | 59 | No Improvement |
| Formaldehyde Releaser | 1-(cis-3-Chloroallyl)-3,5,7-triaza-1-azoniaadamantane chloride Urea + Urea, pH 6.5 (RT) | 0.1% + 0.1% | 58 | No Improvement |
| Formaldehyde Releaser | 1-(cis-3-Chloroallyl)-3,5,7-triaza-1-azoniaadamantane chloride Urea + Ammonium Chloride, pH 6.5 (RT) | 0.1% + 0.1% | 59 | No Improvement |

APPENDIX B

| Compound aassification | Additive | Additive Concentration | % Hb Recovery | Results |
|---|---|---|---|---|
| Formaldehyde Releaser | 1-(cis-3-Chloroallyl)-3,5,7-triaza-1-azoniaadamantane chloride Urea, pH 7.0 (RT) | 0.1% | 56 | No Improvement |
| Formaldehyde Releaser | 1-(cis-3-Chloroallyl)-3,5,7-triaza-1-azoniaadamantane chloride Urea + Glycine, pH 7.0 (RT) | 0.1% + 0.1% | 59 | No Improvement |
| Formaldehyde Releaser | 1-(cis-3-Chloroallyl)-3,5,7-triaza-1-azoniaadamantane chloride Urea + Urea, pH 7.0 (RT) | 0.1% + 0.1% | 57 | No Improvement |
| Formaldehyde Releaser | 1-(cis-3-Chloroallyl)-3,5,7-triaza-1-azoniaadamantane chloride Urea + Ammonium Chloride, pH 7.0 (RT) | 0.1% + 0.1% | 59 | No Improvement |
| Formaldehyde Releaser | 1-(cis-3-ChloroallyI)-3,5,7-triaza-1-azoniaadamantane chloride Urea, pH 7.5 (RT) | 0.1% | 58 | No Improvement |
| Formaldehyde Releaser | 1-(cis-3-Chloroallyl)-3,5,7-triaza-1-azoniaadamantane chloride Urea + Glycine, pH 7.5 (RT) | 0.1% + 0.1% | 57 | No Improvement |
| Formaldehyde Releaser | 1-(cis-3-Chloroallyl)-3,5,7-triaza-1-azoniaadamantane chloride Urea + Urea, pH 7.5 (RT) | 0.1% + 0.1% | 55 | No Improvement |
| Formaldehyde Releaser | 1-(cis-3-Chloroallyl)-3,5,7-triaza-1-azoniaadamantane chloride Urea + Ammonium Chloride, pH 7.5 (RT) | 0.1% + 0.1% | 58 | No Improvement |
| Formaldehyde Releaser | Diazolidinyl Urea + Glycine, pH 7.5 (50 C.) | 0.1% + 0.1% | 62 | No Improvement |
| Formaldehyde Releaser | Diazolidinyl Urea + Glycine, pH 7.5 (50 C.) + methylisothiazolone | 0.1% + 0.1% + 0.2% | 42 | No Improvement |
| Formaldehyde Releaser | Diazolidinyl Urea + Glycine, pH 7.5 (50 C.) + methylisothiazolone | 0.1% + 0.1% + 0.1% | 43 | No Improvement |
| Formaldehyde Releaser | Diazolidinyl Urea + Glycine, pH 7.5 (50 C.) + methylisothiazolone | 0.1% + 0.1% + 0.05% | 41 | No Improvement |
| Formaldehyde Releaser | Diazolidinyl Urea + Glycine, pH 7.5 (50 C.) | 0.3% + 0.3% | 64 | No Improvement |
| Formaldehyde Releaser | Diazolidinyl Urea + Glycine, pH 7.5 (50 C.) + methylisothiazolone | 0.3% + 0.3% + 0.6% | 42 | No Improvement |
| Formaldehyde Releaser | Diazolidinyl Urea + Glycine, pH 7.5 (50 C.) + methylisothiazolone | 0.3% + 0.3% + 0.3% | 33 | No Improvement |
| Formaldehyde Releaser | Diazolidinyl Urea + Glycine, pH 7.5 (50 C.) + methylisothiazolone | 0.3% + 0.3% + 0.15% | 35 | No Improvement |
| Formaldehyde Releaser | Bronopol + ATA, pH 6.5 | 0.002% + 0.002% | 72 | No Improvement |
| Formaldehyde Releaser | Bronopol + ATA, pH 7.5 | 0.002% + 0.002% | 68 | No Improvement |
| Formaldehyde Releaser | Bronopol + ATA, pH 8.5 | 0.020% + 0.002% | 70 | No Improvement |
| Formaldehyde Releaser | Bronopol + ATA, pH 6.5 | 0.001% + 0.002% | 71 | No Improvement |
| Formaldehyde Releaser | Bronopol + ATA, pH 7.5 | 0.001% + 0.002% | 67 | No Improvement |
| Formaldehyde Releaser | Bronopol + ATA, pH 8.5 | 0.001% + 0.002% | 68 | No Improvement |
| Formaldehyde Releaser | Bronopol + ATA, pH 6.5 | 0.004% + 0.002% | 71 | No Improvement |
| Formaldehyde Releaser | Bronopol + ATA, pH 7.5 | 0.004% + 0.002% | 71 | No Improvement |
| Formaldehyde Releaser | Bronopol + ATA, pH 8.5 | 0.004% + 0.002% | 72 | No Improvement |
| Formaldehyde Releaser | Bronopol + Methylisothiazolone, pH 6.5 | 0.002% + 0.002% | 63 | No Improvement |
| Formaldehyde Releaser | Bronopol + Methylisothiazolone, pH 7.5 | 0.002% + 0.002% | 65 | No Improvement |
| Formaldehyde Releaser | Bronopol + Methylisothiazolone, pH 8.5 | 0.002% + 0.002% | 59 | No Improvement |
| Formaldehyde Releaser | Bronopol + Methylisothiazolone, pH 6.5 | 0.001% + 0.002% | 62 | No Improvement |
| Formaldehyde Releaser | Bronopol + Methylisothiazolone, pH 7.5 | 0.001% + 0.002% | 65 | No Improvement |
| Formaldehyde Releaser | Bronopol + Methylisothiazolone, pH 8.5 | 0.001% + 0.002% | 64 | No Improvement |
| Formaldehyde Releaser | Bronopol + Methylisothiazolone, pH 6.5 | 0.004% + 0.002% | 65 | No Improvement |
| Formaldehyde Releaser | Bronopol + Methylisothiazolone, pH 7.5 | 0.004% + 0.002% | 66 | No Improvement |
| Formaldehyde Releaser | Bronopol + Methylisothiazolone, pH 8.5 | 0.004% + 0.002% | 65 | No Improvement |
| Formaldehyde Releaser | Diazolidinyl Urea + ATA, pH 6.5 | 0.002% + 0.002% | 71 | No Improvement |
| Formaldehyde Releaser | Diazolidinyl Urea + ATA, pH 7.5 | 0.002% + 0.002% | 66 | No Improvement |
| Formaldehyde Releaser | Diazolidinyl Urea + ATA, pH 8.5 | 0.002% + 0.002% | 69 | No Improvement |
| Formaldehyde Releaser | Diazolidinyl Urea + ATA, pH 6.5 | 0.001% + 0.002% | 69 | No Improvement |
| Formaldehyde Releaser | Diazolidinyl Urea + ATA, pH 7.5 | 0.001% + 0.002% | 65 | No Improvement |
| Formaldehyde Releaser | Diazolidinyl Urea + ATA, pH 8.5 | 0.001% + 0.002% | 73 | No Improvement |
| Formaldehyde Releaser | Diazolidinyl Urea + ATA, pH 6.5 | 0.004% + 0.002% | 69 | No Improvement |
| Formaldehyde Releaser | Diazolidinyl Urea + ATA, pH 7.5 | 0.004% + 0.002% | 65 | No Improvement |
| Formaldehyde Releaser | Diazolidinyl Urea + ATA, pH 8.5 | 0.004% + 0.002% | 70 | No Improvement |
| Formaldehyde Releaser | Diazolidinyl Urea + Methylisothiazolone, pH 6.5 | 0.002% + 0.002% | 58 | No Improvement |
| Formaldehyde Releaser | Diazolidinyl Urea + Methylisothiazolone, pH 7.5 | 0.002% + 0.002% | 58 | No Improvement |
| Formaldehyde Releaser | Diazolidinyl Urea + Methylisothiazolone, pH 8.5 | 0.002% + 0.002% | 60 | No Improvement |
| Formaldehyde Releaser | Diazolidinyl Urea + Methylisothiazolone, pH 6.5 | 0.001% + 0.002% | 62 | No Improvement |

APPENDIX B

| Compound aassification | Additive | Additive Concentration | % Hb Recovery | Results |
| --- | --- | --- | --- | --- |
| Formaldehyde Releaser | Diazolidinyl Urea + Methylisothiazolone, pH 7.5 | 0.001% + 0.002% | 62 | No Improvement |
| Formaldehyde Releaser | Diazolidinyl Urea + Methylisothiazolone, pH 8.5 | 0.001% + 0.002% | 58 | No Improvement |
| Formaldehyde Releaser | Diazolidinyl Urea + Methylisothiazolone, pH 6.5 | 0.004% + 0.002% | 60 | No Improvement |
| Formaldehyde Releaser | Diazolidinyl Urea + Methylisothiazolone, pH 7.5 | 0.004% + 0.002% | 62 | No Improvement |
| Formaldehyde Releaser | Diazolidinyl Urea + Methylisothiazolone, pH 8.5 | 0.004% + 0.002% | 59 | No Improvement |
| Aldehydes | Formaldehyde | 0.10% | 58 | No Improvement |
| Aldehydes | Formaldehyde | 0.50% | 54 | No Improvement |
| Aldehydes | Formaldehyde | 1% | 25 | No Improvement |
| Aldehydes | Formaldehyde | 2% | 5 | No Improvement |
| Aldehydes | Formaldehyde | 3% | 4 | No Improvement |
| Aldehydes | Formaldehyde | 4% | 4 | No Improvement |
| Aldehydes | Formaldehyde | 5% | 6 | No Improvement |
| HRP Stabilizer Components | HRP Conjugate Stabilizer (PN 85R-102) + Calcium Chloride | 15% + 10 mM | 93 | Improvement in % Hb Recovery |
| HRP Stabilizer Components | HRP Conjugate Stabilizer (PN 85R-102) + Magnesium Sulfate | 15% + 10 mM | 99 | Improvement in % Hb Recovery |
| HRP Stabilizer Components | HRP Conjugate Stabilizer (PN 85R-102) + | 10% | 84 | Improvement in % Hb Recovery |
| HRP Stabilizer Components | HRP Conjugate Stabilizer (PN 85R-102) + | 15% | 85 | Improvement in % Hb Recovery |
| HRP Stabilizer Components | HRP Conjugate Stabilizer (PN 85R-102) + | 20% | 84 | Improvement in % Hb Recovery |
| HRP Stabilizer Components | Fetal Bovine Serum, Bronidox, Methyl isothiazolone, Proclin 300 in 10 mM MOPS, pH 6.3 | 10% (1%, 0.02%, 0.02%, 0.002%) | 53 | No Improvement |
| HRP Stabilizer Components | Fetal Bovine Serum, Bronidox, Methyl isothiazolone, Proclin 300 in 10 mM MOPS, pH 6.3 | 15% (1%, 0.02%, 0.02%, 0.002%) | 51 | No Improvement |
| HRP Stabilizer Components | Fetal Bovine Serum, Bronidox, Methyl isothiazolone, Proclin 300 in 10 mM MOPS, pH 6.3 | 20% (1%, 0.02%, 0.02%, 0.002%) | 54 | No Improvement |
| HRP Stabilizer Components | Fetal Bovine Serum, Bronidox, Methyl isothiazolone, Proclin 300 in 10 mM MOPS, pH 6.3 | 10% (1%, 0.02%, 0.02%, 0.002%) | 59 | No Improvement |
| HRP Stabilizer Components | Fetal Bovine Serum, Bronidox, Methyl isothiazolone, Proclin 300 in 10 mM MOPS, pH 6.3 | 15% (1%, 0.02%, 0.02%, 0.002%) | 61 | No Improvement |
| HRP Stabilizer Components | Fetal Bovine Serum, Bronidox, Methyl isothiazolone, Proclin 300 in 10 mM MOPS, pH 6.3 | 20% (1%, 0.02%, 0.02%, 0.002%) | 49 | No Improvement |
| HRP Stabilizer Components | Fetal Bovine Serum, Bronidox, Methyl isothiazolone, Proclin 300 Calcium Chloride in 10 mM MOPS, pH 6.3 | 10% (1%, 0.02%, 0.02%, 0.002%, 10 mM) | 54 | No Improvement |
| HRP Stabilizer Components | Fetal Bovine Serum, Bronidox, Methyl isothiazolone, Proclin 300 Calcium Chloride in 10 mM MOPS, pH 6.3 | 15% (1%, 0.02%, 0.02%, 0.002%, 10 mM) | 55 | No Improvement |
| HRP Stabilizer Components | Fetal Bovine Serum, Bronidox, Methyl isothiazolone, Proclin 300 Calcium Chloride in 10 mM MOPS, pH 6.3 | 20% (1%, 0.02%, 0.02%, 0.002%, 10 mM) | 56 | No Improvement |
| HRP Stabilizer Components | Fetal Bovine Serum, Bronidox, Methyl isothiazolone, Proclin 300, Magnesium Sulfate in 10 mM MOPS, pH 6.3 | 10% (1%, 0.02%, 0.02%, 0.002%, 10 mM) | 56 | No Improvement |
| HRP Stabilizer Components | Fetal Bovine Serum, Bronidox, Methyl isothiazolone, Proclin 300, Magnesium Sulfate in 10 mM MOPS, pH 6.3 | 15% (1%, 0.02%, 0.02%, 0.002%, 10 mM) | 54 | No Improvement |
| HRP Stabilizer Components | Fetal Bovine Serum, Bronidox, Methyl isothiazolone, Proclin 300, Magnesium Sulfate in 10 mM MOPS, pH 6.3 | 20% (1%, 0.02%, 0.02%, 0.002%, 10 mM) | 53 | No Improvement |
| Substrates | diphosphoglycerate | 1 mM | 68 | No Improvement |
| Metal Chelators | Phytic Acid | 1% | 33 | No Improvement |
| Formaldehyde Releaser | Diazolidinyl Urea, EDTA, Glycine in 10 mM MOPS, pH 7.5 | 1% (325 g/L, 90 g/L, 40 g/L) | 63 | No Improvement |
| Formaldehyde Releaser | Diazolidinyl Urea, EDTA, Glycinein 10 mM MOPS, pH 7.5 + Diphosphoglycerate | 1% (325 g/L, 90 g/L, 40 g/L, 1 mM) | 37 | No Improvement |
| Formaldehyde Releaser | Diazolidinyl Urea, EDTA, Glycine in 10 mM MOPS, pH 7.5 + Phytic Acid | 1% (325 g/L, 90 g/L, 40 g/L, 1%) | 38 | No Improvement |
| Formaldehyde Releaser | Diazolidinyl Urea, EDTA, Glycine in 10 mM MOPS, pH 8.5 | 1% (325 g/L, 90 g/L, 40 g/L) | 34 | No Improvement |

APPENDIX B

| Compound aassification | Additive | Additive Concentration | % Hb Recovery | Results |
|---|---|---|---|---|
| Formaldehyde Releaser | Diazolidinyl Urea, EDTA, Glycinein 10 mM MOPS, pH 8.5 + Diphosphoglycerate | 1% (325 g/L, 90 g/L, 40 g/L, 1 mM) | 58 | No Improvement |
| Formaldehyde Releaser | Diazolidinyl Urea, EDTA, Glycine in 10 mM MOPS, pH 8.5 + Phytic Acid | 1% (325 g/L, 90 g/L, 40 g/L, 1%) | 57 | No Improvement |
| Formaldehyde Releaser | Diazolidinyl Urea, EDTA, Glycine in 10 mM MOPS, pH 7.5 | 10% (325 g/L, 90 g/L, 40 g/L) | 65 | No Improvement |
| Formaldehyde Releaser | Diazolidinyl Urea, EDTA, Glycinein 10 mM MOPS, pH 7.5 + Diphosphoglycerate | 10% (325 g/L, 90 g/L, 40 g/L, 1 mM) | 39 | No Improvement |
| Formaldehyde Releaser | Diazolidinyl Urea, EDTA, Glycine in 10 mM MOPS, pH 7.5 + Phytic Acid | 10% (325 g/L, 90 g/L, 40 g/L, 1%) | 39 | No Improvement |
| Formaldehyde Releaser | Diazolidinyl Urea, EDTA, Glycine in 10 mM MOPS, pH 8.5 | 10% (325 g/L, 90 g/L, 40 g/L) | 51 | No Improvement |
| Formaldehyde Releaser | Diazolidinyl Urea, EDTA, Glycinein 10 mM MOPS, pH 8.5 + Diphosphoglycerate | 10% (325 g/L, 90 g/L, 40 g/L, 1 mM) | 70 | No Improvement |
| Formaldehyde Releaser | Diazolidinyl Urea, EDTA, Glycine in 10 mM MOPS, pH 8.5 + Phytic Acid | 10% (325 g/L, 90 g/L, 40 g/L, 1%) | 76 | No Improvement |
| Formaldehyde Releaser | Diazolidinyl Urea, EDTA, Glycine in 10 mM MOPS, pH 7.5 | 20% (325 g/L, 90 g/L, 40 g/L) | 57 | No Improvement |
| Formaldehyde Releaser | Diazolidinyl Urea, EDTA, Glycinein 10 mM MOPS, pH 7.5 + Diphosphoglycerate | 20% (325 g/L, 90 g/L, 40 g/L, 1 mM) | 52 | No Improvement |
| Formaldehyde Releaser | Diazolidinyl Urea, EDTA, Glycine in 10 mM MOPS, pH 7.5 + Phytic Acid | 20% (325 g/L, 90 g/L, 40 g/L, 1%) | 49 | No Improvement |
| Formaldehyde Releaser | Diazolidinyl Urea, EDTA, Glycine in 10 mM MOPS, pH 8.5 | 20% (325 g/L, 90 g/L, 40 g/L) | 24 | No Improvement |
| Formaldehyde Releaser | Diazolidinyl Urea, EDTA, Glycinein 10 mM MOPS, pH 8.5 + Diphosphoglycerate | 20% (325 g/L, 90 g/L, 40 g/L, 1 mM) | 46 | No Improvement |
| Formaldehyde Releaser | Diazolidinyl Urea, EDTA, Glycine in 10 mM MOPS, pH 8.5 + Phytic Acid | 20% (325 g/L, 90 g/L, 40 g/L, 1%) | 44 | No Improvement |
| HRP Stabilizer Components | HRP Conjugate Stabilizer (PN 85R-102) | 15% | 86 | Improvement in % Hb Recovery |
| HRP Stabilizer Components | HRP Conjugate Stabilizer (PN 85R-102) (diluted with water) | 15% (diluted 4% with water) | 82 | Improvement in % Hb Recovery |
| HRP Stabilizer Components | HRP Conjugate Stabilizer (PN 85R-102) + Calcium Chloride | 15% + 10 mM | 93 | Improvement in % Hb Recovery |
| Polyvalent Ions/Metal Salts | Calcium Chloride | 10 mM | 75 | Calcium cation shows improvement in % Hb Recovery at 10 mM |
| HRP Stabilizer Components | HRP Conjugate Stabilizer (PN 85R-102) + Magnesium Sulfate | 15% + 10 mM | 90 | Improvement in % Hb Recovery |
| Polyvalent Ions/Metal Salts | Magnesium Sulfate | 10 mM | 75 | Magnesium Cation shows improvement in % Hb Recovery around 10 mM |
| HRP Stabilizer Components | HRP Conjugate Stabilizer (PN 85R-102) | 15% | 82 | Improvement in % Hb Recovery |
| HRP Stabilizer Components | HRP Conjugate Stabilizer (PN 85R-102) (diluted with water) | 15% (diluted 4% with water) | 91 | Improvement in % Hb Recovery |
| HRP Stabilizer Components | HRP Conjugate Stabilizer (PN 85R-102) + Calcium Chloride (comp) | 15% + 10 mM | 90 | Improvement in % Hb Recovery |
| HRP Stabilizer Components | HRP Conjugate Stabilizer (PN 85R-102) + Calcium Chloride (spike) | 15% + 10 mM | 102 | Improvement in % Hb Recovery |
| HRP Stabilizer Components | HRP Conjugate Stabilizer (PN 85R-102) + Magnesium Sulfate (comp) | 15% + 10 mM | 92 | Improvement in % Hb Recovery |
| HRP Stabilizer Components | HRP Conjugate Stabilizer (PN 85R-102) + Magnesium Sulfate (spike) | 15% + 10 mM | 97 | Improvement in % Hb Recovery |
| HRP Stabilizer Components | HRP Conjugate Stabilizer (PN 85R-102) + Cobalt Chloride | 15% + 10 mM | 65 | Improvement in % Hb Recovery |
| HRP Stabilizer Components | HRP Conjugate Stabilizer (PN 85R-102) + Copper Chloride | 15% + 10 mM | 77 | Improvement in % Hb Recovery |
| HRP Stabilizer Components | HRP Conjugate Stabilizer (PN 85R-102) + Iron (III) Chloride | 15% + 10 mM | 75 | Improvement in % Hb Recovery |
| HRP Stabilizer Components | HRP Conjugate Stabilizer (PN 85R-102) + Nickel Chloride | 15% + 10 mM | 90 | Improvement in % Hb Recovery |
| HRP Stabilizer Components | HRP Conjugate Stabilizer (PN 85R-102) + Zinc Chloride | 15% + 10 mM | 91 | Improvement in % Hb Recovery |
| HRP Stabilizer Components | HRP Conjugate Stabilizer (PN 85R-102) | 15% | 87 | Improvement in % Hb Recovery |
| HRP Stabilizer Components | HRP Conjugate Stabilizer (PN 85R-102) (diluted with water) | 15% (diluted 4% with water) | 82 | Improvement in % Hb Recovery |
| HRP Stabilizer Components | HRP Conjugate Stabilizer (PN 85R-102) + Calcium Chloride | 15% + 10 mM | 100 | Improvement in % Hb Recovery |
| HRP Stabilizer Components | HRP Conjugate Stabilizer (PN 85R-102) + Magnesium Sulfate | 15% + 10 mM | 96 | Improvement in % Hb Recovery |
| HRP Stabilizer Components | HRP Conjugate Stabilizer (PN 85R-102) + Aluminum Chloride | 15% + 10 mM | 90 | Improvement in % Hb Recovery |

APPENDIX B

| Compound aassification | Additive | Additive Concentration | % Hb Recovery | Results |
| --- | --- | --- | --- | --- |
| HRP Stabilizer Components | HRP Conjugate Stabilizer (PN 85R-102) + Lithium Chloride | 15% + 10 mM | 118 | Improvement in % Hb Recovery |
| HRP Stabilizer Components | HRP Conjugate Stabilizer (PN 85R-102) + Sodium Chloride | 15% + 10 mM | 79 | Improvement in % Hb Recovery |
| Polyvalent Ions/Metal Salts | Calcium Chloride anhydrous | 0.1 mM | 73 | Calcium cation shows improvement in % Hb Recovery at 10 mM |
| Polyvalent Ions/Metal Salts | Calcium Chloride anhydrous | 1 mM | 71 | Calcium cation shows improvement in % Hb Recovery at 10 mM |
| Polyvalent Ions/Metal Salts | Calcium Chloride anhydrous | 2 mM | 72 | Calcium cation shows improvement in % Hb Recovery at 10 mM |
| Polyvalent Ions/Metal Salts | Calcium Chloride anhydrous | 4 mM | 73 | Calcium cation shows improvement in % Hb Recovery at 10 mM |
| Polyvalent Ions/Metal Salts | Calcium Chloride anhydrous | 6 mM | 77 | Calcium cation shows improvement in % Hb Recovery at 10 mM |
| Polyvalent Ions/Metal Salts | Calcium Chloride anhydrous | 8 mM | 75 | Calcium cation shows improvement in % Hb Recovery at 10 mM |
| Polyvalent Ions/Metal Salts | Calcium Chloride anhydrous | 10 mM | 79 | Calcium cation shows improvement in % Hb Recovery at 10 mM |
| Polyvalent Ions/Metal Salts | Calcium Chloride anhydrous | 20 mM | 76 | Calcium cation shows improvement in % Hb Recovery at 10 mM |
| Polyvalent Ions/Metal Salts | Calcium Chloride dihydrate | 0.1 mM | 71 | Calcium cation shows improvement in % Hb Recovery at 10 mM |
| Polyvalent Ions/Metal Salts | Calcium Chloride dihydrate | 1 mM | 70 | Calcium cation shows improvement in % Hb Recovery at 10 mM |
| Polyvalent Ions/Metal Salts | Calcium Chloride dihydrate | 2 mM | 71 | Calcium cation shows improvement in % Hb Recovery at 10 mM |
| Polyvalent Ions/Metal Salts | Calcium Chloride dihydrate | 4 mM | 74 | Calcium cation shows improvement in % Hb Recovery at 10 mM |
| Polyvalent Ions/Metal Salts | Calcium Chloride dihydrate | 6 mM | 74 | Calcium cation shows improvement in % Hb Recovery at 10 mM |
| Polyvalent Ions/Metal Salts | Calcium Chloride dihydrate | 8 mM | 72 | Calcium cation shows improvement in % Hb Recovery at 10 mM |
| Polyvalent Ions/Metal Salts | Calcium Chloride dihydrate | 10 mM | 77 | Calcium cation shows improvement in % Hb Recovery at 10 mM |
| Polyvalent Ions/Metal Salts | Calcium Chloride dihydrate | 20 mM | 73 | Calcium cation shows improvement in % Hb Recovery at 10 mM |
| Plasma | Human Plasma | 1% | 96 | No improvement. High Background Signals |
| Plasma | Human Plasma (no sample) | 1% | 99 | No improvement. High Background Signals |
| Plasma | Human Plasma | 5% | 97 | No improvement. High Background Signals |
| Plasma | Human Plasma (no sample) | 5% | 94 | No improvement. High Background Signals |
| Plasma | Human Plasma | 10% | 96 | No improvement. High Background Signals |
| Plasma | Human Plasma (no sample) | 10% | 98 | No improvement. High Background Signals |
| Plasma | Human Plasma | 25% | 98 | No improvement. High Background Signals |
| Plasma | Human Plasma (no sample) | 25% | 97 | No improvement. High Background Signals |
| Plasma | Human Plasma | 50% | 99 | No improvement. High Background Signals |
| Plasma | Human Plasma (no sample) | 50% | 97 | No improvement. High Background Signals |
| Plasma | Human Plasma | 0.005% | 81 | No improvement. High Background Signals |

-continued

APPENDIX B

| Compound aassification | Additive | Additive Concentration | % Hb Recovery | Results |
|---|---|---|---|---|
| Plasma | Human Plasma (no sample) | 0.005% | 103 | No improvement. High Background Signals |
| Plasma | Human Plasma | 0.005% | 77 | No improvement. High Background Signals |
| Plasma | Human Plasma (no sample) | 0.005% | 99 | No improvement. High Background Signals |
| Plasma | Human Plasma | 0.01% | 81 | No improvement. High Background Signals |
| Plasma | Human Plasma (no sample) | 0.01% | 106 | No improvement. High Background Signals |
| Plasma | Human Plasma | 0.01% | 80 | No improvement. High Background Signals |
| Plasma | Human Plasma (no sample) | 0.01% | 101 | No improvement. High Background Signals |
| Plasma | Human Plasma | 0.05% | 101 | No improvement. High Background Signals |
| Plasma | Human Plasma (no sample) | 0.05% | 100 | No improvement. High Background Signals |
| Plasma | Human Plasma | 0.05% | 95 | No improvement. High Background Signals |
| Plasma | Human Plasma (no sample) | 0.05% | 98 | No improvement. High Background Signals |
| Plasma | Human Plasma | 0.01% | 99 | No improvement. High Background Signals |
| Plasma | Human Plasma (no sample) | 0.01% | 99 | No improvement. High Background Signals |
| Plasma | Human Plasma | 0.01% | 99 | No improvement. High Background Signals |
| Plasma | Human Plasma (no sample) | 0.01% | 99 | No improvement. High Background Signals |
| Plasma | Human Albumin | 0.0025 mg/mL | 71 | No improvement. High Background Signals |
| Plasma | Human Albumin (no sample) | 0.0025 mg/mL | 105 | No improvement. High Background Signals |
| Plasma | Human Albumin | 0.025 mg/mL | 90 | No improvement. High Background Signals |
| Plasma | Human Albumin (no sample) | 0.025 mg/mL | 95 | No improvement. High Background Signals |
| Plasma | Human Albumin | 0.25 mg/mL | 98 | No improvement. High Background Signals |
| Plasma | Human Albumin (no sample) | 0.25 mg/mL | 95 | No improvement. High Background Signals |
| Plasma | Human Albumin | 2.5 mg/mL | 99 | No improvement. High Background Signals |
| Plasma | Human Albumin (no sample) | 2.5 mg/mL | 98 | No improvement. High Background Signals |
| Plasma | Human Albumin | 25 mg/mL | 98 | No improvement. High Background Signals |
| Plasma | Human Albumin (no sample) | 25 mg/mL | 96 | No improvement. High Background Signals |
| Plasma | Glycine | 0.0002 mg/mL | 68 | No improvement |
| Plasma | Glycine (no sample) | 0.0002 mg/mL | 88 | No improvement |
| Plasma | Glycine | 0.002 mg/mL | 68 | No improvement |
| Plasma | Glycine (no sample) | 0.002 mg/mL | 218 | No improvement |
| Plasma | Glycine | 0.02 mg/mL | 71 | No improvement |
| Plasma | Glycine (no sample) | 0.02 mg/mL | 132 | No improvement |
| Plasma | Crohn's Fraction II/III | 0.005 mg/mL | 70 | No improvement. High Background Signals |
| Plasma | Crohn's Fraction II/III (no sample) | 0.005 mg/mL | 106 | No improvement. High Background Signals |
| Plasma | Crohn's Fraction II/III | 0.05 mg/mL | 80 | No improvement. High Background Signals |
| Plasma | Crohn's Fraction II/III (no sample) | 0.05 mg/mL | 107 | No improvement. High Background Signals |
| Plasma | Crohn's Fraction II/III | 0.5 mg/mL | 99 | No improvement. High Background Signals |
| Plasma | Crohn's Fraction II/III (no sample) | 0.5 mg/mL | 103 | No improvement. High Background Signals |
| Plasma | Crohn's Fraction II/III | 5 mg/mL | 100 | No improvement. High Background Signals |
| Plasma | Crohn's Fraction II/III (no sample) | 5 mg/mL | 97 | No improvement. High Background Signals |
| Plasma | Crohn's Fraction II/III | 50 mg/mL | 97 | No improvement. High Background Signals |

APPENDIX B

| Compound aassification | Additive | Additive Concentration | % Hb Recovery | Results |
|---|---|---|---|---|
| Plasma | Crohn's Fraction II/III (no sample) | 50 mg/mL | 109 | No improvement. High Background Signals |
| Plasma | Crohn's Fraction IV | 0.005 mg/mL | 106 | No improvement. High Background Signals |
| Plasma | Crohn's Fraction IV (no sample) | 0.005 mg/mL | 93 | No improvement. High Background Signals |
| Plasma | Crohn's Fraction IV | 0.05 mg/mL | 100 | No improvement. High Background Signals |
| Plasma | Crohn's Fraction IV (no sample) | 0.05 mg/mL | 88 | No improvement. High Background Signals |
| Plasma | Crohn's Fraction IV | 0.5 mg/mL | 98 | No improvement. High Background Signals |
| Plasma | Crohn's Fraction IV (no sample) | 0.5 mg/mL | 94 | No improvement. High Background Signals |
| Plasma | Crohn's Fraction IV | 5 mg/mL | 96 | No improvement. High Background Signals |
| Plasma | Crohn's Fraction IV (no sample) | 5 mg/mL | 97 | No improvement. High Background Signals |
| Plasma | Crohn's Fraction IV | 50 mg/mL | 98 | No improvement. High Background Signals |
| Plasma | Crohn's Fraction IV (no sample) | 50 mg/mL | 98 | No improvement. High Background Signals |
| Plasma | HDL | 0.0025 mg/mL | 69 | No improvement |
| Plasma | HDL (no sample) | 0.0025 mg/mL | 128 | No improvement |
| Plasma | HDL | 0.025 mg/mL | 69 | No improvement |
| Plasma | HDL (no sample) | 0.025 mg/mL | 117 | No improvement |
| Plasma | HDL | 0.25 mg/mL | 70 | No improvement |
| Plasma | HDL (no sample) | 0.25 mg/mL | 106 | No improvement |
| Plasma | LDL | 0.0025 mg/mL | 69 | No improvement |
| Plasma | LDL (no sample) | 0.0025 mg/mL | 109 | No improvement |
| Plasma | LDL | 0.025 mg/mL | 70 | No improvement |
| Plasma | LDL (no sample) | 0.025 mg/mL | 93 | No improvement |
| Plasma | LDL | 0.25 mg/mL | 67 | No improvement |
| Plasma | LDL (no sample) | 0.25 mg/mL | 180 | No improvement |
| Plasma | phosphatidylcholine | 0.01 mg/mL | 67 | No improvement |
| Plasma | phosphatidylcholine (no sample) | 0.01 mg/mL | 80 | No improvement |
| Plasma | phosphatidylcholine | 0.1 mg/mL | 68 | No improvement |
| Plasma | phosphatidylcholine (no sample) | 0.1 mg/mL | 91 | No improvement |
| Plasma | phosphatidylcholine | 1 mg/mL | 62 | No improvement |
| Plasma | phosphatidylcholine (no sample) | 1 mg/mL | 118 | No improvement |
| Plasma | Bovine Serum | 0.001% | 71 | No improvement |
| Plasma | Bovine Serum (no sample) | 0.001% | 94 | No improvement |
| Plasma | Bovine Serum | 0.01% | 72 | No improvement |
| Plasma | Bovine Serum (no sample) | 0.01% | 62 | No improvement |
| Plasma | Bovine Serum | 0.10% | 61 | No improvement |
| Plasma | Bovine Serum (no sample) | 0.10% | 71 | No improvement |
| Plasma | Bovine Serum | 1% | 38 | No improvement |
| Plasma | Bovine Serum (no sample) | 1% | 126 | No improvement |
| Plasma | Lyopholized Human Plasma | 0.001% | 71 | No improvement. High Background Signals |
| Plasma | Lyopholized Human Plasma (no sample) | 0.001% | 96 | No improvement. High Background Signals |
| Plasma | Lyopholized Human Plasma | 0.01% | 79 | No improvement. High Background Signals |
| Plasma | Lyopholized Human Plasma (no sample) | 0.01% | 104 | No improvement. High Background Signals |
| Plasma | Lyopholized Human Plasma | 0.10% | 93 | No improvement. High Background Signals |
| Plasma | Lyopholized Human Plasma (no sample) | 0.10% | 99 | No improvement. High Background Signals |
| Plasma | Lyopholized Human Plasma | 1% | 95 | No improvement. High Background Signals |
| Plasma | Lyopholized Human Plasma (no sample) | 1% | 100 | No improvement. High Background Signals |
| Plasma | Pooled Human Plasma (22137) | 0.001% | 69 | No improvement. High Background Signals |
| Plasma | Pooled Human Plasma (22137) (no sample) | 0.001% | 118 | No improvement. High Background Signals |
| Plasma | Pooled Human Plasma (22137) | 0.01% | 80 | No improvement. High Background Signals |
| Plasma | Pooled Human Plasma (22137) (no sample) | 0.01% | 98 | No improvement. High Background Signals |
| Plasma | Pooled Human Plasma (22137) | 0.10% | 95 | No improvement. High Background Signals |

APPENDIX B

| Compound aassification | Additive | Additive Concentration | % Hb Recovery | Results |
|---|---|---|---|---|
| Plasma | Pooled Human Plasma (22137) (no sample) | 0.10% | 101 | No improvement. High Background Signals |
| Plasma | Pooled Human Plasma (22137) | 1% | 98 | No improvement. High Background Signals |
| Plasma | Pooled Human Plasma (22137) (no sample) | 1% | 99 | No improvement. High Background Signals |
| Plasma | Pooled Human Plasma (22355) | 0.001% | 78 | No improvement. High Background Signals |
| Plasma | Pooled Human Plasma (22355) (no sample) | 0.001% | 81 | No improvement. High Background Signals |
| Plasma | Pooled Human Plasma (22355) | 0.01% | 88 | No improvement. High Background Signals |
| Plasma | Pooled Human Plasma (22355) (no sample) | 0.01% | 119 | No improvement. High Background Signals |
| Plasma | Pooled Human Plasma (22355) | 0.10% | 98 | No improvement. High Background Signals |
| Plasma | Pooled Human Plasma (22355) (no sample) | 0.10% | 100 | No improvement. High Background Signals |
| Plasma | Pooled Human Plasma (22355) | 1% | 94 | No improvement. High Background Signals |
| Plasma | Pooled Human Plasma (22355) (no sample) | 1% | 99 | No improvement. High Background Signals |
| Plasma | SD Human Plasma (23 94459A) | 0.001% | 72 | No improvement. High Background Signals |
| Plasma | SD Human Plasma (23 94459A) (no sample) | 0.001% | 114 | No improvement. High Background Signals |
| Plasma | SD Human Plasma (23 94459A) | 0.01% | 91 | No improvement. High Background Signals |
| Plasma | SD Human Plasma (23 94459A) (no sample) | 0.01% | 96 | No improvement. High Background Signals |
| Plasma | SD Human Plasma (23 94459A) | 0.10% | 94 | No improvement. High Background Signals |
| Plasma | SD Human Plasma (23 94459A) (no sample) | 0.10% | 104 | No improvement. High Background Signals |
| Plasma | SD Human Plasma (23 94459A) | 1% | 101 | No improvement. High Background Signals |
| Plasma | SD Human Plasma (23 94459A) (no sample) | 1% | 106 | No improvement. High Background Signals |
| Plasma | SD Human Plasma (23 94460A) | 0.001% | 71 | No improvement. High Background Signals |
| Plasma | SD Human Plasma (23 94460A) (no sample) | 0.001% | 138 | No improvement. High Background Signals |
| Plasma | SD Human Plasma (23 94460A) | 0.01% | 87 | No improvement. High Background Signals |
| Plasma | SD Human Plasma (23 94460A) (no sample) | 0.01% | 137 | No improvement. High Background Signals |
| Plasma | SD Human Plasma (23 94460A) | 0.10% | 98 | No improvement. High Background Signals |
| Plasma | SD Human Plasma (23 94460A) (no sample) | 0.10% | 102 | No improvement. High Background Signals |
| Plasma | SD Human Plasma (23 94460A) | 1% | 96 | No improvement. High Background Signals |
| Plasma | SD Human Plasma (23 94460A) (no sample) | 1% | 104 | No improvement. High Background Signals |
| Plasma | SD Human Plasma (23 94460A), spun 2x | 0.001% | 73 | No improvement. High Background Signals |
| Plasma | SD Human Plasma (23 94460A), spun 2x (no sample) | 0.001% | 101 | No improvement. High Background Signals |
| Plasma | SD Human Plasma (23 94460A), spun 2x | 0.01% | 84 | No improvement. High Background Signals |
| Plasma | SD Human Plasma (23 94460A), spun 2x (no sample) | 0.01% | 89 | No improvement. High Background Signals |
| Plasma | SD Human Plasma (23 94460A), spun 2x | 0.10% | 99 | No improvement. High Background Signals |
| Plasma | SD Human Plasma (23 94460A), spun 2x (no sample) | 0.10% | 95 | No improvement. High Background Signals |
| Plasma | SD Human Plasma (23 94460A), spun 2x | 1% | 101 | No improvement. High Background Signals |
| Plasma | SD Human Plasma (23 94460A), spun 2x (no sample) | 1% | 105 | No improvement. High Background Signals |
| Plasma | SD Human Plasma (23 94464A) | 0.001% | 77 | No improvement. High Background Signals |
| Plasma | SD Human Plasma (23 94464A) (no sample) | 0.001% | 91 | No improvement. High Background Signals |

APPENDIX B

| Compound aassification | Additive | Additive Concentration | % Hb Recovery | Results |
| --- | --- | --- | --- | --- |
| Plasma | SD Human Plasma (23 94464A) | 0.01% | 91 | No improvement. High Background Signals |
| Plasma | SD Human Plasma (23 94464A) (no sample) | 0.01% | 114 | No improvement. High Background Signals |
| Plasma | SD Human Plasma (23 94464A) | 0.10% | 99 | No improvement. High Background Signals |
| Plasma | SD Human Plasma (23 94464A) (no sample) | 0.10% | 101 | No improvement. High Background Signals |
| Plasma | SD Human Plasma (23 94464A) | 1% | 99 | No improvement. High Background Signals |
| Plasma | SD Human Plasma (23 94464A) (no sample) | 1% | 103 | No improvement. High Background Signals |
| Plasma | SD Human Plasma (23 95813A) | 0.001% | 71 | No improvement. High Background Signals |
| Plasma | SD Human Plasma (23 95813A) (no sample) | 0.001% | 106 | No improvement. High Background Signals |
| Plasma | SD Human Plasma (23 95813A) | 0.01% | 75 | No improvement. High Background Signals |
| Plasma | SD Human Plasma (23 95813A) (no sample) | 0.01% | 96 | No improvement. High Background Signals |
| Plasma | SD Human Plasma (23 95813A) | 0.10% | 103 | No improvement. High Background Signals |
| Plasma | SD Human Plasma (23 95813A) (no sample) | 0.10% | 103 | No improvement. High Background Signals |
| Plasma | SD Human Plasma (23 95813A) | 1% | 100 | No improvement. High Background Signals |
| Plasma | SD Human Plasma (23 95813A) (no sample) | 1% | 105 | No improvement. High Background Signals |
| Plasma | SD Human Plasma (23 95819A) | 0.001% | 72 | No improvement. High Background Signals |
| Plasma | SD Human Plasma (23 95819A) (no sample) | 0.001% | 109 | No improvement. High Background Signals |
| Plasma | SD Human Plasma (23 95819A) | 0.01% | 77 | No improvement. High Background Signals |
| Plasma | SD Human Plasma (23 95819A) (no sample) | 0.01% | 136 | No improvement. High Background Signals |
| Plasma | SD Human Plasma (23 95819A) | 0.10% | 103 | No improvement. High Background Signals |
| Plasma | SD Human Plasma (23 95819A) (no sample) | 0.10% | 107 | No improvement. High Background Signals |
| Plasma | SD Human Plasma (23 95819A) | 1% | 101 | No improvement. High Background Signals |
| Plasma | SD Human Plasma (23 95819A) (no sample) | 1% | 108 | No improvement. High Background Signals |
| Non-covalent Hb interactions | MOPS + BSA | 15% (10 mM + 1%) | 76 | No improvement |
| Polyvalent Ions/Metal Salts | Calcium Chloride | 10 mM | 75 | Calcium cation shows improvement in % Hb Recovery at 10 mM |
| Polyvalent Ions/Metal Salts | Magnesium Sulfate | 10 mM | 73 | Magnesium Cation shows improvement in % Hb Recovery around 10 mM |
| HRP Stabilizer Components | HRP Conjugate Stabilizer (PN ab171537) | 15% | 76 | Improvement in % Hb Recovery |
| HRP Stabilizer Components | HRP Conjugate Stabilizer (PN ab171537) + Calcium Chloride | 15% + 10 mM | 87 | Improvement in % Hb Recovery |
| HRP Stabilizer Components | HRP Conjugate Stabilizer (PN ab171537) + Magnesium Sulfate | 15% + 10 mM | 89 | Improvement in % Hb Recovery |
| HRP Stabilizer Components | HRP Conjugate Stabilizer (PN ab171537) (diluted with water) | 15% + 4% | 76 | Improvement in % Hb Recovery |
| HRP Stabilizer Components | HRP Conjugate Stabilizer (PN SZ02) | 15% | 75 | Improvement in % Hb Recovery |
| HRP Stabilizer Components | HRP Conjugate Stabilizer (PN SZ02) Calcium Chloride | 15% + 10 mM | 87 | Improvement in % Hb Recovery |
| HRP Stabilizer Components | HRP Conjugate Stabilizer (PN SZ02) Magnesium Sulfate | 15% + 10 mM | 92 | Improvement in % Hb Recovery |
| HRP Stabilizer Components | HRP Conjugate Stabilizer (PN SZ02) (diluted with water) | 15% + 4% | 77 | Improvement in % Hb Recovery |
| HRP Stabilizer Components | HRP Conjugate Stabilizer (PN 85R-102) | 15% | 77 | Improvement in % Hb Recovery |
| HRP Stabilizer Components | HRP Conjugate Stabilizer (PN 85R-102) + Calcium Chloride | 15% + 10 mM | 92 | Improvement in % Hb Recovery |
| HRP Stabilizer Components | HRP Conjugate Stabilizer (PN 85R-102) + Magnesium Sulfate | 15% + 10 mM | 95 | Improvement in % Hb Recovery |

APPENDIX B

| Compound aassification | Additive | Additive Concentration | % Hb Recovery | Results |
|---|---|---|---|---|
| HRP Stabilizer Components | HRP Conjugate Stabilizer (PN 85R-102) (diluted with water) | 15% + 4% | 77 | Improvement in % Hb Recovery |
| Polyvalent Ions/Metal Salts | Calcium Chloride | 10 mM | 71 | No improvement |
| HRP Stabilizer Components | HRP Conjugate Stabilizer (PN 85R-102) | 15% | 79 | Improvement in % Hb Recovery |
| HRP Stabilizer Components | HRP Conjugate Stabilizer (PN 85R-102) + Calcium Chloride | 15% + 10 mM | 85 | Improvement in % Hb Recovery |
| Sugars/Saccharides | Galaturonic Acid | 1% | 37 | No improvement |
| Sugars/Saccharides | Galaturonic Acid | 1% + 10 mM | 41 | No improvement |
| Sugars/Saccharides | Galaturonic Acid | 0.10% | 75 | No improvement |
| Sugars/Saccharides | Galaturonic Acid | 0.1% + 10 mM | 72 | No improvement |
| Sugars/Saccharides | Galaturonic Acid | 0.01% | 69 | No improvement |
| Sugars/Saccharides | Galaturonic Acid | 0.01% + 10 mM | 73 | No improvement |
| Sugars/Saccharides | Polygalacturonic Acid | 0.20% | 70 | No improvement |
| Sugars/Saccharides | Polygalacturonic Acid + Calcium Chloride | 0.2% + 10 mM | 58 | No improvement |
| Sugars/Saccharides | Polygalacturonic Acid | 0.10% | 70 | No improvement |
| Sugars/Saccharides | Polygalacturonic Acid + Calcium Chloride | 0.1% + 10 mM | 83 | Improvement in % Hb Recovery |
| Sugars/Saccharides | Polygalacturonic Acid | 0.05% | 68 | No improvement |
| Sugars/Saccharides | Polygalacturonic Acid + Calcium Chloride | 0.05% + 10 mM | 75 | Improvement in % Hb Recovery |
| Sugars/Saccharides | Polygalacturonic Acid | 0.01% | 69 | No improvement |
| Sugars/Saccharides | Polygalacturonic Acid + Calcium Chloride | 0.01% + 10 mM | 74 | Improvement in % Hb Recovery |
| Polyvalent Ions/Metal Salts | Calcium Chloride | 10 mM | 72 | Improvement in % Hb Recovery |
| Polyvalent Ions/Metal Salts | Magnesium Sulfate | 10 mM | 76 | Improvement in % Hb Recovery |
| Polyvalent Ions/Metal Salts | Calcium Chloride + Magnesium Sulfate | 10 mM + 10 mM | 72 | Improvement in % Hb Recovery |
| HRP Stabilizer Components | HRP Conjugate Stabilizer (PN 85R-102) | 15% | 78 | Improvement in % Hb Recovery |
| HRP Stabilizer Components | HRP Conjugate Stabilizer (PN 85R-102) + Calcium Chloride | 15% + 10 mM | 83 | Improvement in % Hb Recovery |
| HRP Stabilizer Components | HRP Conjugate Stabilizer (PN 85R-102) + Magnesium Sulfate | 15% + 10 mM | 78 | Improvement in % Hb Recovery |
| HRP Stabilizer Components | HRP Conjugate Stabilizer (PN 85R-102) + CaCl2 + MgSO4 | 15% + 10 mM + 10 mM | 82 | Improvement in % Hb Recovery |
| HRP Stabilizer Components | HRP Conjugate Stabilizer (PN ab171537) | 15% | 72 | Improvement in % Hb Recovery |
| HRP Stabilizer Components | HRP Conjugate Stabilizer (PN ab171537) + Calcium Chloride | 15% + 10 mM | 78 | Improvement in % Hb Recovery |
| HRP Stabilizer Components | HRP Conjugate Stabilizer (PN ab171537) + Magnesium Sulfate | 15% + 10 mM | 76 | Improvement in % Hb Recovery |
| HRP Stabilizer Components | HRP Conjugate Buffer + CaCl2 + MgSO4 | 15% + 10 mM + 10 mM | 78 | Improvement in % Hb Recovery |
| HRP Stabilizer Components | HRP Conjugate Stabilizer (PN SZ02) | 15% | 71 | Improvement in % Hb Recovery |
| HRP Stabilizer Components | HRP Conjugate Stabilizer (PN SZ02) + Calcium Chloride | 15% + 10 mM | 77 | Improvement in % Hb Recovery |
| HRP Stabilizer Components | HRP Conjugate Stabilizer (PN SZ02) + Magnesium Sulfate | 15% + 10 mM | 79 | Improvement in % Hb Recovery |
| HRP Stabilizer Components | HRP Conjugate Stabilizer (PN SZ02) + CaCl2 + MgSO4 | 15% + 10 mM + 10 mM | 80 | Improvement in % Hb Recovery |
| Polyvalent Ions/Metal Salts | Calcium Chloride | 10 mM | 82 | Improvement in % Hb Recovery |
| Polyvalent Ions/Metal Salts | Magnesium Sulfate | 10 mM | 89 | Improvement in % Hb Recovery |
| Polyvalent Ions/Metal Salts | Calcium Chloride + Magnesium Sulfate | 10 mM + 10 mM | 81 | Improvement in % Hb Recovery |
| Polyvalent Ions/Metal Salts | Calcium Chloride + Magnesium Sulfate | 10 mM + 5 mM | 78 | Improvement in % Hb Recovery |
| Polyvalent Ions/Metal Salts | Calcium Chloride + Magnesium Sulfate | 5 mM + 10 mM | 90 | Improvement in % Hb Recovery |
| Polyvalent Ions/Metal Salts | Calcium Chloride + Magnesium Sulfate | 5 mM + 5 mm | 87 | Improvement in % Hb Recovery |
| HRP Stabilizer Components | HRP Conjugate Stabilizer (PN 85R-102) | 15% | 80 | Improvement in % Hb Recovery |
| HRP Stabilizer Components | HRP Conjugate Stabilizer (PN 85R-102) + Calcium Chloride | 15% + 10 mM | 87 | Improvement in % Hb Recovery |
| HRP Stabilizer Components | HRP Conjugate Stabilizer (PN 85R-102) + Magnesium Sulfate | 15% + 10 mM | 92 | Improvement in % Hb Recovery |
| HRP Stabilizer Components | HRP Conjugate Stabilizer (PN 85R-102) + CaCl2 + MgSO4 | 15% + 10 mM + 10 mM | 87 | Improvement in % Hb Recovery |

APPENDIX B

| Compound aassification | Additive | Additive Concentration | % Hb Recovery | Results |
|---|---|---|---|---|
| HRP Stabilizer Components | HRP Conjugate Stabilizer (PN 85R-102) + CaCl2 + MgSO4 | 15% + 10 mM + 5 mM | 89 | Improvement in % Hb Recovery |
| HRP Stabilizer Components | HRP Conjugate Stabilizer (PN 85R-102) + CaCl2 + MgSO4 | 15% + 5 mM + 10 mM | 90 | Improvement in % Hb Recovery |
| HRP Stabilizer Components | HRP Conjugate Stabilizer (PN 85R-102) + CaCl2 + MgSO4 | 15% + 5 mM + 5 mM | 89 | Improvement in % Hb Recovery |
| HRP Stabilizer Components | HRP Conjugate Stabilizer (PN SZ02) | 15% | 78 | Improvement in % Hb Recovery |
| HRP Stabilizer Components | HRP Conjugate Stabilizer (PN SZ02) + Calcium Chloride | 15% + 10 mM | 89 | Improvement in % Hb Recovery |
| HRP Stabilizer Components | HRP Conjugate Stabilizer (PN SZ02) + Magnesium Sulfate | 15% + 10 mM | 86 | Improvement in % Hb Recovery |
| HRP Stabilizer Components | HRP Conjugate Stabilizer (PN SZ02) + CaCl2 + MgSO4 | 15% + 10 mM + 10 mM | 90 | Improvement in % Hb Recovery |
| HRP Stabilizer Components | HRP Conjugate Stabilizer (PN SZ02) + CaCl2 + MgSO4 | 15% + 10 mM + 5 mM | 89 | Improvement in % Hb Recovery |
| HRP Stabilizer Components | HRP Conjugate Stabilizer (PN SZ02) + CaCl2 + MgSO4 | 15% + 5 mM + 10 mM | 82 | Improvement in % Hb Recovery |
| HRP Stabilizer Components | HRP Conjugate Stabilizer (PN SZ02) + CaCl2 + MgSO4 | 15% + 5 mM + 5 mM | 87 | Improvement in % Hb Recovery |
| pH Adjustments | Hb Collection Buffer, pH 6.5 | NA | 84 | Improvement in % Hb Recovery |
| Polyvalent Ions/Metal Salts | Calcium Chloride | 10 mM | 79 | Improvement in % Hb Recovery |
| HRP Stabilizer Components | HR Conjugate Stabilizer (PN 85R-102) Calcium Chloride | 15% + 10 mM | 89 | Improvement in % Hb Recovery |
| Sugars/Saccharides | Polygalacturonic Acid + Calcium Chloride | 0.01% + 10 mM | 83 | Improvement in % Hb Recovery |
| Sugars/Saccharides | Polygalacturonic Acid + Calcium Chloride | 0.025% + 10 mM | 91 | Improvement in % Hb Recovery |
| Sugars/Saccharides | Polygalacturonic Acid + Calcium Chloride | 0.05% + 10 mM | 86 | Improvement in % Hb Recovery |
| Sugars/Saccharides | Polygalacturonic Acid + Calcium Chloride | 0.075% + 10 mM | 79 | Improvement in % Hb Recovery |
| Sugars/Saccharides | Polygalacturonic Acid + Calcium Chloride | 0.1% + 10 mM | 64 | Improvement in % Hb Recovery |
| Sugars/Saccharides | Polygalacturonic Acid + Calcium Chloride | 0.125% + 10 mM | 86 | Improvement in % Hb Recovery |
| Sugars/Saccharides | Sodium Alginate (Medium Viscosity) | 0.01% | 58 | No Improvement |
| Sugars/Saccharides | Sodium Alginate (Medium Viscosity) CaCl2 | 0.01% + 10 mM | 62 | No Improvement |
| Sugars/Saccharides | Sodium Alginate (Medium Viscosity) | 0.05% | 56 | No Improvement |
| Sugars/Saccharides | Sodium Alginate (Medium Viscosity) + CaCl2 | 0.5% + 10 mM | 58 | No Improvement |
| Sugars/Saccharides | Sodium Alginate (Medium Viscosity) | 0.10% | 46 | No Improvement |
| Sugars/Saccharides | Sodium Alginate (Medium Viscosity) + CaCl2 | 0.1% + 10 mM | 45 | No Improvement |
| Sugars/Saccharides | Sodium Alginate (Medium Viscosity) | 0.20% | 29 | No Improvement |
| Sugars/Saccharides | Sodium Alginate (Medium Viscosity) + CaCl2 | 0.2% + 10 mM | 25 | No Improvement |
| Sugars/Saccharides | Sodium Alginate (Synthetic) | 0.01% | 61 | No Improvement |
| Sugars/Saccharides | Sodium Alginate (Synthetic) + CaCl2 | 0.01% + 10 mM | 62 | No Improvement |
| Sugars/Saccharides | Sodium Alginate (Synthetic) | 0.05% | 50 | No Improvement |
| Sugars/Saccharides | Sodium Alginate (Synthetic) + CaCl2 | 0.05% + 10 mM | 57 | No Improvement |
| Sugars/Saccharides | Sodium Alginate (Synthetic) | 0.10% | 57 | No Improvement |
| Sugars/Saccharides | Sodium Alginate (Synthetic) + CaCl2 | 0.1% + 10 mM | 52 | No Improvement |
| Sugars/Saccharides | Sodium Alginate (Synthetic) | 0.20% | 56 | No Improvement |
| Sugars/Saccharides | Sodium Alginate (Synthetic) + CaCl2 | 0.2% + 10 mM | 50 | No Improvement |
| HRP Stabilizer Components | HRP Conjugate Stabilizer (PN 85R-102) | 15% | 78 | Improvement in % Hb Recovery |
| HRP Stabilizer Components | HRP Conjugate Stabilizer (PN 85R-102) Calcium Chloride | 15% + 10 mM | 80 | Improvement in % Hb Recovery |
| Sugars/Saccharides | Sodium Alginate (Low Viscosity) | 0.01% | 59 | No Improvement |
| Sugars/Saccharides | Sodium Alginate (Low Viscosity) + CaCl2 | 0.01% + 10 mM | 61 | No Improvement |
| Sugars/Saccharides | Sodium Alginate (Low Viscosity) | 0.05% | 53 | No Improvement |
| Sugars/Saccharides | Sodium Alginate (Low Viscosity) + CaCl2 | 0.05% + 10 mM | 59 | No Improvement |
| Sugars/Saccharides | Sodium Alginate (Low Viscosity) | 0.10% | 54 | No Improvement |
| Sugars/Saccharides | Sodium Alginate (Low Viscosity) + CaCl2 | 0.1% + 10 mM | 64 | No Improvement |
| Sugars/Saccharides | Sodium Alginate (Low Viscosity) | 0.20% | 48 | No Improvement |
| Sugars/Saccharides | Sodium Alginate (Low Viscosity) + CaCl2 | 0.2% + 10 mM | 54 | No Improvement |
| HRP Stabilizer Components | HRP Conjugate Stabilizer (PN 85R-102) | 15% | 79 | Improvement in % Hb Recovery |
| HRP Stabilizer Components | HRP Conjugate Stabilizer (PN 85R-102) + Calcium Chloride | 15% + 10 mM | 81 | Improvement in % Hb Recovery |

APPENDIX B

| Compound aassification | Additive | Additive Concentration | % Hb Recovery | Results |
|---|---|---|---|---|
| HRP Stabilizer Components | HRP Conjugate Stabilizer (PN 85R-102) | 100% | 78 | Improvement in % Hb Recovery |
| HRP Stabilizer Components | HRP Conjugate Stabilizer (PN 85R-102) + CaCl2 | 100% + 10 mM | 83 | Improvement in % Hb Recovery |
| HRP Stabilizer Components | HRP Conjugate Stabilizer (PN 85R-102) + MgSO4 | 100% + 10 mM | 78 | Improvement in % Hb Recovery |
| HRP Stabilizer Components | HRP Conjugate Stabilizer (PN 85R-102) + CaCl2 + MgSO4 | 100% + 10 mM + 10 mM | 82 | Improvement in % Hb Recovery |
| HRP Stabilizer Components | HRP Conjugate Stabilizer (PN ab171537) | 100% | 72 | Improvement in % Hb Recovery |
| HRP Stabilizer Components | HRP Conjugate Stabilizer (PN ab171537) + CaCl2 | 100% + 10 mM | 78 | Improvement in % Hb Recovery |
| HRP Stabilizer Components | HRP Conjugate Stabilizer (PN ab171537) + MgSO4 | 100% + 10 mM | 76 | Improvement in % Hb Recovery |
| HRP Stabilizer Components | HRP Conjugate Stabilizer (PN ab171537) + CaCl2 + MgSO4 | 100% + 10 mM + 10 mM | 78 | Improvement in % Hb Recovery |
| HRP Stabilizer Components | HRP Conjugate Stabilizer (PN SZ02) | 100% | 71 | Improvement in % Hb Recovery |
| HRP Stabilizer Components | HRP Conjugate Stabilizer (PN SZ02) + CaCl2 | 100% + 10 mM | 77 | Improvement in % Hb Recovery |
| HRP Stabilizer Components | HRP Conjugate Stabilizer (PN SZ02) + MgSO4 | 100% + 10 mM | 79 | Improvement in % Hb Recovery |
| HRP Stabilizer Components | HRP Conjugate Stabilizer (PN SZ02) + CaCl2 + MgSO4 | 100% + 10 mM + 10 mM | 80 | Improvement in % Hb Recovery |
| Polyvalent Ions/Metal Salts | Calcium Chloride, pH 6.5 | 10 mM | 72 | No Improvement |
| HRP Stabilizer Components | HRP Conjugate Stabilizer (PN 85R-102), pH 6.5 | 15% | 87 | Improvement in % Hb Recovery |
| HRP Stabilizer Components | HRP Conjugate Stabilizer (PN 85R-102) + CaCl2, pH 6.5 | 15% + 10 mM | 86 | Improvement in % Hb Recovery |
| HRP Stabilizer Components | BSA | 10% | 66 | No Improvement |
| HRP Stabilizer Components | BSA, pH 6.5 | 10% | 69 | No Improvement |
| HRP Stabilizer Components | BSA + HRP Conjugate Stabilizer (PN 85R-102), pH 6.5 | 10% + 15% | 80 | Improvement in % Hb Recovery |
| HRP Stabilizer Components | BSA | 5% | 67 | No Improvement |
| HRP Stabilizer Components | BSA, pH 6.5 | 5% | 67 | No Improvement |
| HRP Stabilizer Components | BSA + HRP Conjugate Stabilizer (PN 85R-102), pH 6.5 | 5% + 15% | 74 | Improvement in % Hb Recovery |
| HRP Stabilizer Components | BSA | 1% | 56 | No Improvement |
| HRP Stabilizer Components | BSA, pH 6.5 | 1% | 60 | No Improvement |
| HRP Stabilizer Components | BSA + HRP Conjugate Stabilizer (PN 85R-102), pH 6.5 | 1% + 15% | 75 | Improvement in % Hb Recovery |
| HRP Stabilizer Components | BSA | 0.50% | 50 | No Improvement |
| HRP Stabilizer Components | BSA, pH 6.5 | 0.50% | 56 | No Improvement |
| HRP Stabilizer Components | BSA + HRP Conjugate Stabilizer (PN 85R-102), pH 6.5 | 0.5% + 15% | 80 | Improvement in % Hb Recovery |
| HRP Stabilizer Components | BSA | 0% | 47 | No Improvement |
| HRP Stabilizer Components | BSA, pH 6.5 | 0% | 51 | No Improvement |
| HRP Stabilizer Components | BSA + HRP Conjugate Stabilizer (PN 85R-102), pH 6.5 | 0% + 15% | 83 | Improvement in % Hb Recovery |
| Protoporphyrin | Protoporphyrin IX | 1 uM | 68 | No Improvement |
| Protoporphyrin | Protoporphyrin IX | 10 uM | 70 | No Improvement |
| Protoporphyrin | Protoporphyrin IX | 100 uM | 66 | No Improvement |
| Protoporphyrin | Protoporphyrin IX Zinc | 1 uM | 96 | Improvement in % Hb Recovery |
| Protoporphyrin | Protoporphyrin IX Zinc | 10 uM | 72 | Improvement in % Hb Recovery |
| Protoporphyrin | Protoporphyrin IX Zinc | 100 uM | 73 | Improvement in % Hb Recovery |
| Protoporphyrin | Protoporphyrin IX + Zinc Chloride | 1 uM + 1 uM | 92 | Improvement in % Hb Recovery |
| Protoporphyrin | Protoporphyrin IX + Zinc Chloride | 10 uM + 10 uM | 87 | Improvement in % Hb Recovery |
| Protoporphyrin | Protoporphyrin IX + Zinc Chloride | 100 uM + 100 uM | 83 | Improvement in % Hb Recovery |
| Protoporphyrin | Protoporphyrin IX + Iron (II) Chloride | 1 uM + 1 uM | 71 | No Improvement |
| Protoporphyrin | Protoporphyrin IX + Iron (II) Chloride | 10 uM + 10 uM | 65 | No Improvement |
| Protoporphyrin | Protoporphyrin IX + Iron (II) Chloride | 100 uM + 100 uM | 71 | No Improvement |
| Protoporphyrin | Protoporphyrin IX + Iron (III) Chloride | 1 uM + 1 uM | 65 | No Improvement |
| Protoporphyrin | Protoporphyrin IX + Iron (III) Chloride | 10 uM + 10 uM | 66 | No Improvement |
| Protoporphyrin | Protoporphyrin IX + Iron (III) Chloride | 100 uM + 100 uM | 60 | No Improvement |
| HRP Stabilizer Components | HRP Conjugate Stabilizer (PN SZ02) | 0.15 | 70 | No Improvement |
| Protoporphyrin | Protoporphyrin IX | 0.001 uM | 54 | No Improvement |
| Protoporphyrin | Protoporphyrin IX | 0.01 uM | 50 | No Improvement |
| Protoporphyrin | Protoporphyrin IX | 0.1 uM | 50 | No Improvement |

-continued

| Compound aassification | Additive | Additive Concentration | % Hb Recovery | Results |
|---|---|---|---|---|
| Protoporphyrin | Protoporphyrin IX | 1 uM | 74 | Improvement in % Hb Recovery |
| Protoporphyrin | Protoporphyrin IX Zinc | 0.001 uM | 51 | No Improvement |
| Protoporphyrin | Protoporphyrin IX Zinc | 0.01 uM | 73 | Improvement in % Hb Recovery |
| Protoporphyrin | Protoporphyrin IX Zinc | 0.1 uM | 88 | Improvement in % Hb Recovery |
| Protoporphyrin | Protoporphyrin IX Zinc | 1 uM | 66 | Improvement in % Hb Recovery |
| Protoporphyrin | Protoporphyrin IX + Zinc Chloride | 0.001 uM + 0.001 uM | 59 | No Improvement |
| Protoporphyrin | Protoporphyrin IX + Zinc Chloride | 0.01 uM + 0.01 uM | 51 | No Improvement |
| Protoporphyrin | Protoporphyrin IX + Zinc Chloride | 0.1 uM + 0.1 uM | 57 | No Improvement |
| Protoporphyrin | Protoporphyrin IX + Zinc Chloride | 1 uM + 1 uM | 53 | No Improvement |
| HRP Stabilizer Components | HRP Conjugate Stabilizer (PN 85R-102) | 15% | 66 | Improvement in % Hb Recovery |
| HRP Stabilizer Components | HRP Conjugate Stabilizer (PN 85R-102), pH 6.5 | 15% | 93 | Improvement in % Hb Recovery |
| Protoporphyrin | Protoporphyrin IX | 0.1 uM | 68 | No Improvement |
| Protoporphyrin | Protoporphyrin IX | 1 uM | 69 | No Improvement |
| Protoporphyrin | Protoporphyrin IX | 10 uM | 63 | No Improvement |
| Protoporphyrin | Protoporphyrin IX Copper | 0.1 uM | 70 | No Improvement |
| Protoporphyrin | Protoporphyrin IX Copper | 1 uM | 67 | No Improvement |
| Protoporphyrin | Protoporphyrin IX Copper | 10 uM | 66 | No Improvement |
| Protoporphyrin | Protoporphyrin IX Magnesium | 0.1 uM | 65 | No Improvement |
| Protoporphyrin | Protoporphyrin IX Magnesium | 1 uM | 69 | No Improvement |
| Protoporphyrin | Protoporphyrin IX Magnesium | 10 uM | 73 | No Improvement |
| Protoporphyrin | Protoporphyrin IX Tin | 0.1 uM | 69 | No Improvement |
| Protoporphyrin | Protoporphyrin IX Tin | 1 uM | 66 | No Improvement |
| Protoporphyrin | Protoporphyrin IX Tin | 10 uM | 66 | No Improvement |
| Protoporphyrin | Protoporphyrin IX Zinc | 0.1 uM | 83 | Improvement in % Hb Recovery |
| Protoporphyrin | Protoporphyrin IX Zinc | 1 uM | 90 | Improvement in % Hb Recovery |
| Protoporphyrin | Protoporphyrin IX Zinc | 10 uM | 90 | Improvement in % Hb Recovery |
| HRP Stabilizer Components | HRP Conjugate Stabilizer (PN 85R-102), pH 6.5 | 15% | 89 | Improvement in % Hb Recovery |
| Protoporphyrin | Hemin, pH 6.5 | 0.0003% | 101 | Improvement in % Hb Recovery |
| Protoporphyrin | Hemin + BSA | 1.5 mM + 1.5 mM | 80 | Improvement in % Hb Recovery |
| Protoporphyrin | Hemin + BSA | 22.5 mM + 22.5 mM | 88 | Improvement in % Hb Recovery |
| Protoporphyrin | Hemin + BSA | 3 mM + 1.5 mM | 81 | Improvement in % Hb Recovery |
| Protoporphyrin | Hemin + BSA | 45 mM + 22.5 mM | 92 | Improvement in % Hb Recovery |
| Protoporphyrin | Hemin + BSA | 4.5 mM + 1.5 mM | 85 | Improvement in % Hb Recovery |
| Protoporphyrin | Hemin + BSA | 67.5 mM + 22.5 mM | 88 | Improvement in % Hb Recovery |
| Protoporphyrin | Protoporphyrin IX Tin + BSA | 1.5 mM + 1.5 mM | 69 | No Improvement |
| Protoporphyrin | Protoporphyrin IX Tin + BSA | 22.5 mM + 22.5 mM | 69 | No Improvement |
| Protoporphyrin | Protoporphyrin IX Tin + BSA | 3 mM + 1.5 mM | 68 | No Improvement |
| Protoporphyrin | Protoporphyrin IX Tin + BSA | 45 mM + 22.5 mM | 70 | No Improvement |
| Protoporphyrin | Protoporphyrin IX Tin + BSA | 4.5 mM + 1.5 mM | 71 | No Improvement |
| Protoporphyrin | Protoporphyrin IX Tin + BSA | 67.5 mM + 22.5 mM | 70 | No Improvement |
| Protoporphyrin | Protoporphyrin IX Zinc + BSA | 1.5 mM + 1.5 mM | 88 | Improvement in % Hb Recovery |
| Protoporphyrin | Protoporphyrin IX Zinc + BSA | 22.5 mM + 22.5 mM | 86 | Improvement in % Hb Recovery |
| Protoporphyrin | Protoporphyrin IX Zinc + BSA | 3 mM + 1.5 mM | 90 | Improvement in % Hb Recovery |
| Protoporphyrin | Protoporphyrin IX Zinc + BSA | 45 mM + 22.5 mM | 87 | Improvement in % Hb Recovery |
| Protoporphyrin | Protoporphyrin IX Zinc + BSA | 4.5 mM + 1.5 mM | 82 | Improvement in % Hb Recovery |
| Protoporphyrin | Protoporphyrin IX Zinc + BSA | 67.5 mM + 22.5 mM | 78 | Improvement in % Hb Recovery |
| Protoporphyrin | Protoporphyrin IX + BSA | 1.5 mM + 1.5 mM | 66 | No Improvement |
| Protoporphyrin | Protoporphyrin IX + BSA | 22.5 mM + 22.5 mM | 63 | No Improvement |
| Protoporphyrin | Protoporphyrin IX + BSA | 3 mM + 1.5 mM | 64 | No Improvement |
| Protoporphyrin | Protoporphyrin IX + BSA | 45 mM + 22.5 mM | 69 | No Improvement |
| Protoporphyrin | Protoporphyrin IX + BSA | 4.5 mM + 1.5 mM | 66 | No Improvement |

APPENDIX B

| Compound aassification | Additive | Additive Concentration | % Hb Recovery | Results |
| --- | --- | --- | --- | --- |
| Protoporphyrin | Protoporphyrin IX + BSA | 67.5 mM + 22.5 mM | 65 | No Improvement |
| HRP Stabilizer Components | HRP Conjugate Stabilizer (PN SZ02), pH 6.5 | 15% | 95 | Improvement in % Hb Recovery |
| Protoporphyrin | Protoporphyrin IX | 0.1 uM | 67 | No Improvement |
| Protoporphyrin | Protoporphyrin IX | 1 uM | 74 | No Improvement |
| Protoporphyrin | Protoporphyrin IX | 10 uM | 64 | No Improvement |
| Protoporphyrin | Protoporphyrin IX Cobalt | 0.1 uM | 72 | No Improvement |
| Protoporphyrin | Protoporphyrin IX Cobalt | 1 uM | 78 | No Improvement |
| Protoporphyrin | Protoporphyrin IX Cobalt | 10 uM | 116 | Improvement in % Hb Recovery |
| Protoporphyrin | Protoporphyrin IX Chromium | 0.1 uM | 71 | No Improvement |
| Protoporphyrin | Protoporphyrin IX Chromium | 1 uM | 82 | Improvement in % Hb Recovery |
| Protoporphyrin | Protoporphyrin IX Chromium | 10 uM | 117 | Improvement in % Hb Recovery |
| Protoporphyrin | Protoporphyrin IX Mangansese | 0.1 uM | 74 | No Improvement |
| Protoporphyrin | Protoporphyrin IX Mangansese | 1 uM | 72 | No Improvement |
| Protoporphyrin | Protoporphyrin IX Mangansese | 10 uM | 68 | No Improvement |
| Protoporphyrin | Protoporphyrin IX Zinc | 0.1 uM | 89 | Improvement in % Hb Recovery |
| Protoporphyrin | Protoporphyrin IX Zinc | 1 uM | 95 | Improvement in % Hb Recovery |
| Protoporphyrin | Protoporphyrin IX Zinc | 10 uM | 93 | Improvement in % Hb Recovery |
| HRP Stabilizer Components | HRP Conjugate Stabilizer (PN SZ02), pH 6.5 | 15% | 91 | No Improvement |
| Protoporphyrin | Protoporphyrin IX Cobalt | 1 uM | 75 | Improvement in % Hb Recovery |
| Protoporphyrin | Protoporphyrin IX Cobalt | 2.5 uM | 70 | No Improvement |
| Protoporphyrin | Protoporphyrin IX Cobalt | 5 uM | 90 | Improvement in % Hb Recovery |
| Protoporphyrin | Protoporphyrin IX Chromium | 1 uM | 83 | Improvement in % Hb Recovery |
| Protoporphyrin | Protoporphyrin IX Chromium | 2.5 uM | 96 | Improvement in % Hb Recovery |
| Protoporphyrin | Protoporphyrin IX Chromium | 5 uM | 93 | Improvement in % Hb Recovery |
| Protoporphyrin | Protoporphyrin IX Magnesium | 10 uM | 61 | No Improvement |
| Protoporphyrin | Protoporphyrin IX Magnesium | 25 uM | 66 | No Improvement |
| Protoporphyrin | Protoporphyrin IX Magnesium | 50 uM | 76 | No Improvement |
| Protoporphyrin | Protoporphyrin IX Mangansese | 0.025 uM | 54 | No Improvement |
| Protoporphyrin | Protoporphyrin IX Mangansese | 0.05 uM | 69 | No Improvement |
| Protoporphyrin | Protoporphyrin IX Mangansese | 0.1 uM | 63 | No Improvement |
| Protoporphyrin | Hemin, pH 6.5 | 0.00% | 82 | Improvement in % Hb Recovery |
| HRP Stabilizer Components | HRP Conjugate Stabilizer (PN 85R-102), pH 6.5 | 15% | 91 | Improvement in % Hb Recovery |
| Protoporphyrin | Protoporphyrin IX Cobalt | 5 uM | 103 | Improvement in % Hb Recovery |
| Protoporphyrin | Protoporphyrin IX Chromium | 2.5 uM | 109 | Improvement in % Hb Recovery |
| Protoporphyrin | Protoporphyrin IX Zinc | 0.1 uM | 82 | Improvement in % Hb Recovery |
| Protoporphyrin | Protoporphyrin IX Zinc, pH 6.5 | 0.1 uM | 83 | Improvement in % Hb Recovery |
| Protoporphyrin | Protoporphyrin IX Zinc | 1 uM | 85 | Improvement in % Hb Recovery |
| Protoporphyrin | Protoporphyrin IX Zinc, pH 6.5 | 1 uM | 95 | Improvement in % Hb Recovery |
| Protoporphyrin | Protoporphyrin IX Zinc | 0.1 uM | 84 | Improvement in % Hb Recovery |
| Protoporphyrin | Protoporphyrin IX Zinc, pH 6.5 | 0.1 uM | 82 | Improvement in % Hb Recovery |
| Protoporphyrin | Protoporphyrin IX Zinc | 1 uM | 89 | Improvement in % Hb Recovery |
| Protoporphyrin | Protoporphyrin IX Zinc, pH 6.5 | 1 uM | 103 | Improvement in % Hb Recovery |
| Protoporphyrin | Protoporphyrin IX Zinc | 0.1 uM | 79 | Improvement in % Hb Recovery |
| Protoporphyrin | Protoporphyrin IX Zinc, pH 6.5 | 0.1 uM | 87 | Improvement in % Hb Recovery |
| Protoporphyrin | Protoporphyrin IX Zinc | 1 uM | 81 | Improvement in % Hb Recovery |

-continued

APPENDIX B

| Compound aassification | Additive | Additive Concentration | % Hb Recovery | Results |
|---|---|---|---|---|
| Protoporphyrin | Protoporphyrin IX Zinc, pH 6.5 | 1 uM | 90 | Improvement in % Hb Recovery |
| Protoporphyrin | Protoporphyrin IX Zinc | 0.1 uM | 85 | Improvement in % Hb Recovery |
| Protoporphyrin | Protoporphyrin IX Zinc, pH 6.5 | 0.1 uM | 77 | Improvement in % Hb Recovery |
| Protoporphyrin | Protoporphyrin IX Zinc | 1 uM | 86 | Improvement in % Hb Recovery |
| Protoporphyrin | Protoporphyrin IX Zinc, pH 6.5 | 1 uM | 82 | Improvement in % Hb Recovery |
| Polyvalent Ions/Metal Salts | Calcium Chloride | 10 mM | 71 | No Improvement |
| HRP Stabilizer Components | HRP Conjugate Stabilizer (PN 85R-102) | 15% | 79 | No Improvement |
| HRP Stabilizer Components | HRP Conjugate Stabilizer (PN 85R-102) CaCl2 | 15% + 10 mM | 85 | No Improvement |
| Saccharides/Sugars | Galaturonic Acid | 1% | 37 | No Improvement |
| Saccharides/Sugars | Galaturonic Acid + CaCl2 | 1% + 10 mM | 41 | No Improvement |
| Saccharides/Sugars | Galaturonic Acid | 0.10% | 75 | No Improvement |
| Saccharides/Sugars | Galaturonic Acid + CaCl2 | 0.1% + 10 mM | 72 | No Improvement |
| Saccharides/Sugars | Galaturonic Acid | 0.01% | 69 | No Improvement |
| Saccharides/Sugars | Galaturonic Acid + CaCl2 | 0.01% + 10 mM | 73 | No Improvement |
| Saccharides/Sugars | Polygalacturonic Acid | 0.20% | 70 | No Improvement |
| Saccharides/Sugars | Polygalacturonic Acid + CaCl2 | 0.2% + 10 mM | 58 | No Improvement |
| Saccharides/Sugars | Polygalacturonic Acid | 0.10% | 70 | No Improvement |
| Saccharides/Sugars | Polygalacturonic Acid + CaCl2 | 0.1% + 10 mM | 83 | Improvement in % Hb Recovery |
| Saccharides/Sugars | Polygalacturonic Acid | 0.05% | 68 | No Improvement |
| Saccharides/Sugars | Polygalacturonic Acid + CaCl2 | 0.05% + 10 mM | 75 | No Improvement |
| Saccharides/Sugars | Polygalacturonic Acid | 0.01% | 69 | No Improvement |
| Saccharides/Sugars | Polygalacturonic Acid + CaCl2 | 0.01% + 10 mM | 74 | No Improvement |
| HRP Stabilizer Components | HRP Conjugate Stabilizer (PN 85R-102) | 15% | 84 | Improvement in % Hb Recovery |
| Protoporphyrin | Hemin (DMSO) | 0.0003% | 88 | Improvement in % Hb Recovery |
| Protoporphyrin | Hemin (H2O:NaOH) | 0.0003% | 84 | Improvement in % Hb Recovery |
| Protoporphyrin | Hemin (NaHCO3) | 0.0003% | 90 | Improvement in % Hb Recovery |
| Protoporphyrin | BSA + Hemin (DMSO) | 0.15% + 0.0003% | 90 | Improvement in % Hb Recovery |
| Protoporphyrin | BSA + Hemin (H2O:NaOH) | 0.15% + 0.0003% | 87 | Improvement in % Hb Recovery |
| Protoporphyrin | BSA + Hemin (NaHCO3) | 0.15% + 0.0003% | 90 | Improvement in % Hb Recovery |
| Protoporphyrin | BSA + Hemin (DMSO) | 0.001% + 0.0001% | 85 | Improvement in % Hb Recovery |
| Protoporphyrin | BSA + Hemin (DMSO) | 0.01% + 0.001% | 93 | Improvement in % Hb Recovery |
| Protoporphyrin | BSA + Hemin (DMSO) | 0.1% + 0.01% | 85 | Improvement in % Hb Recovery |
| Protoporphyrin | BSA + Hemin (H2O:NaOH) | 0.001% + 0.0001% | 85 | Improvement in % Hb Recovery |
| Protoporphyrin | BSA + Hemin (H2O:NaOH) | 0.01% + 0.001% | 90 | Improvement in % Hb Recovery |
| Protoporphyrin | BSA + Hemin (H2O:NaOH) | 0.1% + 0.01% | 83 | Improvement in % Hb Recovery |
| Protoporphyrin | BSA + Hemin (NaHCO3) | 0.001% + 0.0001% | 85 | Improvement in % Hb Recovery |
| Protoporphyrin | BSA + Hemin (NaHCO3) | 0.01% + 0.001% | 91 | Improvement in % Hb Recovery |
| Protoporphyrin | BSA + Hemin (NaHCO3) | 0.1% + 0.01% | 72 | Improvement in % Hb Recovery |
| HRP Stabilizer Components | HRP Conjugate Stabilizer (PN 85R-102), pH 6.5 | 15% | 93 | Improvement in % Hb Recovery |
| HRP Stabilizer Components | HRP Conjugate Stabilizer (PN 85R-102) | 15% | 83 | Improvement in % Hb Recovery |
| Protoporphyrin | Hemin (H2O:NaOH) | 0.0003% | 86 | Improvement in % Hb Recovery |
| Protoporphyrin | Hemin (H2O:NaOH) | 0.00005% | 82 | Improvement in % Hb Recovery |
| Protoporphyrin | Hemin (H2O:NaOH) | 0.00009% | 87 | Improvement in % Hb Recovery |
| Protoporphyrin | Hemin (H2O:NaOH) | 0.00018% | 86 | Improvement in % Hb Recovery |

-continued

APPENDIX B

| Compound aassification | Additive | Additive Concentration | % Hb Recovery | Results |
|---|---|---|---|---|
| Protoporphyrin | Hemin (H2O:NaOH) | 0.00037% | 85 | Improvement in % Hb Recovery |
| Protoporphyrin | Hemin (H2O:NaOH) | 0.00075% | 88 | Improvement in % Hb Recovery |
| Protoporphyrin | Hemin (H2O:NaOH) | 0.00015% | 87 | Improvement in % Hb Recovery |
| Protoporphyrin | Hemin (H2O:NaOH) | 0.003% | 90 | Improvement in % Hb Recovery |
| Protoporphyrin | Hemin (H2O:NaOH), pH 6.5 | 0.00005% | 90 | Improvement in % Hb Recovery |
| Protoporphyrin | Hemin (H2O:NaOH), pH 6.5 | 0.00009% | 88 | Improvement in % Hb Recovery |
| Protoporphyrin | Hemin (H2O:NaOH), pH 6.5 | 0.00018% | 92 | Improvement in % Hb Recovery |
| Protoporphyrin | Hemin (H2O:NaOH), pH 6.5 | 0.00037% | 95 | Improvement in % Hb Recovery |
| Protoporphyrin | Hemin (H2O:NaOH), pH 6.5 | 0.00075% | 91 | Improvement in % Hb Recovery |
| Protoporphyrin | Hemin (H2O:NaOH), pH 6.5 | 0.00015% | 94 | Improvement in % Hb Recovery |
| Protoporphyrin | Hemin (H2O:NaOH), pH 6.5 | 0.003% | 89 | Improvement in % Hb Recovery |
| HRP Stabilizer Components | HRP Conjugate Stabilizer (PN 85R-102) | 15% | 95 | Improvement in % Hb Recovery |
| Protoporphyrin | Hemin (H2O:NaOH) | 0.0003% | 90 | Improvement in % Hb Recovery |
| Alternate Hb CB Formulation | Hb CB 10% BSA | NA | 75 | NA |
| Alternate Hb CB Formulation | Hb CB 5% BSA | NA | 73 | NA |
| Alternate Hb CB Formulation | Hb CB 1% BSA | NA | 66 | NA |
| Alternate Hb CB Formulation | Hb CB 0% BSA | NA | 53 | NA |
| Protoporphyrin | Hemin + Hb CB 10% BSA | 0.00003% | 75 | Improvement in % Hb Recovery |
| Protoporphyrin | Hemin + Hb CB 5% BSA | 0.00003% | 80 | Improvement in % Hb Recovery |
| Protoporphyrin | Hemin + Hb CB 1% BSA | 0.00003% | 74 | Improvement in % Hb Recovery |
| Protoporphyrin | Hemin + Hb CB 0% BSA | 0.00003% | 65 | No Improvement |
| Protoporphyrin | Hemin + Hb CB 10% BSA | 0.0003% | 88 | Improvement in % Hb Recovery |
| Protoporphyrin | Hemin + Hb CB 5% BSA | 0.0003% | 90 | Improvement in % Hb Recovery |
| Protoporphyrin | Hemin + Hb CB 1% BSA | 0.0003% | 86 | Improvement in % Hb Recovery |
| Protoporphyrin | Hemin + Hb CB 0% BSA | 0.0003% | 71 | No Improvement |
| Protoporphyrin | Hemin + Hb CB 10% BSA | 0.003% | 84 | Improvement in % Hb Recovery |
| Protoporphyrin | Hemin + Hb CB 5% BSA | 0.003% | 85 | Improvement in % Hb Recovery |
| Protoporphyrin | Hemin + Hb CB 1% BSA | 0.003% | 68 | No Improvement |
| Protoporphyrin | Hemin + Hb CB 0% BSA | 0.003% | 62 | No Improvement |
| HRP Stabilizer Components | HRP Conjugate Stabilizer (PN 85R-102) | 15% | 91 | Improvement in % Hb Recovery |
| Protoporphyrin | Hemin (H2O:NaOH) | 0.0003% | 87 | Improvement in % Hb Recovery |
| Protoporphyrin | Hemin + CaCl2 | 0.0003% + 10 mM | 88 | Improvement in % Hb Recovery |
| Protoporphyrin | Hemin + MgSO4 | 0.0003% + 10 mM | 88 | Improvement in % Hb Recovery |
| Protoporphyrin | Hemin + FeCl2 | 0.0003% + 4.8 uM | 89 | Improvement in % Hb Recovery |
| Protoporphyrin | Hemin + FeCl2 | 0.0003% + 9.6 uM | 87 | Improvement in % Hb Recovery |
| Protoporphyrin | Hemin + FeCl2 | 0.0003% + 2.4 uM | 88 | Improvement in % Hb Recovery |
| Protoporphyrin | Hemin + FeCl3 | 0.0003% + 4.8 uM | 91 | Improvement in % Hb Recovery |
| Protoporphyrin | Hemin + FeCl3 | 0.0003% + 9.6 uM | 91 | Improvement in % Hb Recovery |
| Protoporphyrin | Hemin + FeCl3 | 0.0003% + 2.4 uM | 90 | Improvement in % Hb Recovery |
| Protoporphyrin | BSA + Hemin | 1% + 0.0003% | 90 | Improvement in % Hb Recovery |
| Protoporphyrin | BSA + Hemin + CaCl2 | 1% + 0.0003% + 10 mM | 90 | Improvement in % Hb Recovery |

-continued

APPENDIX B

| Compound aassification | Additive | Additive Concentration | % Hb Recovery | Results |
|---|---|---|---|---|
| Protoporphyrin | BSA + Hemin + MgSO4 | 1% + 0.0003% + 10 mM | 90 | Improvement in % Hb Recovery |
| Protoporphyrin | BSA + Hemin + FeCl2 | 1% + 0.0003% + 4.8 uM | 87 | Improvement in % Hb Recovery |
| Protoporphyrin | BSA + Hemin + FeCl2 | 1% + 0.0003% + 9.6 uM | 90 | Improvement in % Hb Recovery |
| Protoporphyrin | BSA + Hemin + FeCl2 | 1% + 0.0003% + 2.4 uM | 91 | Improvement in % Hb Recovery |
| Protoporphyrin | BSA + Hemin + FeCl3 | 1% + 0.0003% + 4.8 uM | 90 | Improvement in % Hb Recovery |
| Protoporphyrin | BSA + Hemin + FeCl3 | 1% + 0.0003% + 9.6 uM | 89 | Improvement in % Hb Recovery |
| Protoporphyrin | BSA + Hemin + FeCl3 | 1% + 0.0003% + 2.4 uM | 88 | Improvement in % Hb Recovery |
| HRP Stabilizer Components | HRP Conjugate Stabilizer (PN 85R-102) | 15% | 94 | Improvement in % Hb Recovery |
| Protoporphyrin | Hemin, pH 6.4 | 0.0003% | 88 | Improvement in % Hb Recovery |
| Protoporphyrin | Hemin, pH 6.5 | 0.0003% | 88 | Improvement in % Hb Recovery |
| Protoporphyrin | Hemin, pH 6.6 | 0.0003% | 91 | Improvement in % Hb Recovery |
| Protoporphyrin | Hemin, pH 6.7 | 0.0003% | 88 | Improvement in % Hb Recovery |
| Protoporphyrin | Hemin, pH 6.8 | 0.0003% | 89 | Improvement in % Hb Recovery |
| Protoporphyrin | Hemin, pH 6.9 | 0.0003% | 85 | Improvement in % Hb Recovery |
| Protoporphyrin | Hemin, pH 7.0 | 0.0003% | 87 | Improvement in % Hb Recovery |
| Protoporphyrin | Hemin, pH 7.1 | 0.0003% | 88 | Improvement in % Hb Recovery |
| Protoporphyrin | Hemin, pH 7.2 | 0.0003% | 83 | Improvement in % Hb Recovery |
| Protoporphyrin | Hemin, pH 7.3 | 0.0003% | 81 | Improvement in % Hb Recovery |
| Protoporphyrin | Hemin, pH 7.4 | 0.0003% | 81 | Improvement in % Hb Recovery |
| Protoporphyrin | Hemin, pH 7.5 | 0.0003% | 79 | Improvement in % Hb Recovery |
| HRP Stabilizer Components | HRP Conjugate Stabilizer (PN SZ02), pH 6.5 | 15% | 93 | Improvement in % Hb Recovery |
| Protoporphyrin | Hemin (H2O:NaOH) | 0.0003% | 95 | Improvement in % Hb Recovery |
| Alternate Hb CB Formulation | BSA | 22.5 uM | 80 | Improvement in % Hb Recovery |
| Protoporphyrin | Hemin | 4.5 uM | 92 | Improvement in % Hb Recovery |
| Protoporphyrin | Hemin + Sodium Azide | 4.5 uM + 0.0072% | 92 | Improvement in % Hb Recovery |
| Protoporphyrin | Hemin + Sodium Azide | 4.5 uM + 0.014% | 92 | Improvement in % Hb Recovery |
| Protoporphyrin | Hemin + Sodium Azide | 4.5 uM + 0.029% | 92 | Improvement in % Hb Recovery |
| Alternate Hb CB Formulation | Sodium Azide | 0.0072% | 72 | No Improvement |
| Alternate Hb CB Formulation | Sodium Azide | 0.014% | 72 | No Improvement |
| Alternate Hb CB Formulation | Sodium Azide | 0.029% | 73 | No Improvement |
| Protoporphyrin | Hemin + BSA | 4.5 uM + 22.5 uM | 92 | Improvement in % Hb Recovery |
| Protoporphyrin | Hemin + BSA + Sodium Azide | 4.5 uM + 22.5 uM + 0.0072% | 92 | Improvement in % Hb Recovery |
| Protoporphyrin | Hemin + BSA + Sodium Azide | 4.5 uM + 22.5 uM + 0.014% | 89 | Improvement in % Hb Recovery |
| Protoporphyrin | Hemin + BSA + Sodium Azide | 4.5 uM + 22.5 uM + 0.029% | 93 | Improvement in % Hb Recovery |
| Protoporphyrin | Hemin | 4.8 uM | 81 | Improvement in % Hb Recovery |
| Protoporphyrin | Protoporphyrin IX Chromium | 2.5 uM | 105 | Improvement in % Hb Recovery |
| Protoporphyrin | Protoporphyrin IX Cobalt (Vendor 1) | 1.25 uM | 76 | Improvement in % Hb Recovery |
| Protoporphyrin | Protoporphyrin IX Cobalt (Vendor 1) | 2.5 uM | 85 | Improvement in % Hb Recovery |

APPENDIX B

| Compound aassification | Additive | Additive Concentration | % Hb Recovery | Results |
|---|---|---|---|---|
| Protoporphyrin | Protoporphyrin IX Cobalt (Vendor 1) | 5 uM | 103 | Improvement in % Hb Recovery |
| Protoporphyrin | Protoporphyrin IX Cobalt (Vendor 1) | 6.5 uM | 102 | Improvement in % Hb Recovery |
| Protoporphyrin | Protoporphyrin IX Cobalt (Vendor 2) | 1.25 uM | 75 | Improvement in % Hb Recovery |
| Protoporphyrin | Protoporphyrin IX Cobalt (Vendor 2) | 2.5 uM | 89 | Improvement in % Hb Recovery |
| Protoporphyrin | Protoporphyrin IX Cobalt (Vendor 2) | 5 uM | 97 | Improvement in % Hb Recovery |
| Protoporphyrin | Protoporphyrin IX Cobalt (Vendor 2) | 6.5 uM | 108 | Improvement in % Hb Recovery |
| Protoporphyrin | Protoporphyrin IX Cobalt (Vendor 3) | 1.25 uM | 71 | Improvement in % Hb Recovery |
| Protoporphyrin | Protoporphyrin IX Cobalt (Vendor 3) | 2.5 uM | 83 | Improvement in % Hb Recovery |
| Protoporphyrin | Protoporphyrin IX Cobalt (Vendor 3) | 5 uM | 103 | Improvement in % Hb Recovery |
| Protoporphyrin | Protoporphyrin IX Cobalt (Vendor 3) | 6.5 uM | 112 | Improvement in % Hb Recovery |
| Protoporphyrin | Protoporphyrin IX Gallium | 1.25 uM | 68 | No Improvement |
| Protoporphyrin | Protoporphyrin IX Gallium | 2.5 uM | 69 | No Improvement |
| Protoporphyrin | Protoporphyrin IX Gallium | 5 uM | 71 | No Improvement |
| Protoporphyrin | Protoporphyrin IX Gallium | 6.5 uM | 70 | No Improvement |
| Protoporphyrin | Protoporphyrin IX Cobalt | 5 uM | 87 | Improvement in % Hb Recovery |
| Protoporphyrin | Protoporphyrin IX Chromium (Vendor 1) | 1.25 uM | 91 | Improvement in % Hb Recovery |
| Protoporphyrin | Protoporphyrin IX Chromium (Vendor 1) | 2.5 uM | 78 | Improvement in % Hb Recovery |
| Protoporphyrin | Protoporphyrin IX Chromium (Vendor 1) | 5 uM | 92 | Improvement in % Hb Recovery |
| Protoporphyrin | Protoporphyrin IX Chromium (Vendor 1) | 6.5 uM | 104 | Improvement in % Hb Recovery |
| Protoporphyrin | Protoporphyrin IX Chromium (Vendor 2) | 1.25 uM | 72 | Improvement in % Hb Recovery |
| Protoporphyrin | Protoporphyrin IX Chromium (Vendor 2) | 2.5 uM | 71 | Improvement in % Hb Recovery |
| Protoporphyrin | Protoporphyrin IX Chromium (Vendor 2) | 5 uM | 82 | Improvement in % Hb Recovery |
| Protoporphyrin | Protoporphyrin IX Chromium (Vendor 2) | 6.5 uM | 91 | Improvement in % Hb Recovery |
| Protoporphyrin | Protoporphyrin IX Cobalt | 5 uM | 84 | Improvement in % Hb Recovery |
| Protoporphyrin | Protoporphyrin IX Chromium | 2.5 uM | 91 | Improvement in % Hb Recovery |
| Protoporphyrin | Hemin, Bovine | 2.4 uM | 92 | Improvement in % Hb Recovery |
| Protoporphyrin | Hemin, Bovine | 4.8 uM | 89 | Improvement in % Hb Recovery |
| Protoporphyrin | Hemin, Bovine | 9.6 uM | 91 | Improvement in % Hb Recovery |
| Protoporphyrin | Hematin | 2.4 uM | 87 | Improvement in % Hb Recovery |
| Protoporphyrin | Hematin | 3.6 uM | 84 | Improvement in % Hb Recovery |
| Protoporphyrin | Hematin | 4.8 uM | 89 | Improvement in % Hb Recovery |
| Protoporphyrin | Hematin | 6 uM | 89 | Improvement in % Hb Recovery |
| Protoporphyrin | Hematin | 7.2 uM | 87 | Improvement in % Hb Recovery |
| Protoporphyrin | Hematin | 8.4 uM | 92 | Improvement in % Hb Recovery |
| Protoporphyrin | Hematin | 9.6 uM | 90 | Improvement in % Hb Recovery |
| Protoporphyrin | Hemin, Porcine (Vendor 1) | 2.4 uM | 91 | Improvement in % Hb Recovery |
| Protoporphyrin | Hemin, Porcine (Vendor 1) | 4.8 uM | 104 | Improvement in % Hb Recovery |
| Protoporphyrin | Hemin, Porcine (Vendor 1) | 9.6 uM | 92 | Improvement in % Hb Recovery |
| Protoporphyrin | Hemin, Porcine (Vendor 2) | 2.4 uM | 86 | Improvement in % Hb Recovery |

APPENDIX B

| Compound aassification | Additive | Additive Concentration | % Hb Recovery | Results |
| --- | --- | --- | --- | --- |
| Protoporphyrin | Hemin, Porcine (Vendor 2) | 4.8 uM | 90 | Improvement in % Hb Recovery |
| Protoporphyrin | Hemin, Porcine (Vendor 2) | 9.6 uM | 92 | Improvement in % Hb Recovery |
| Non covalent Hb interactions | Polyvinylpyrrolidone (10,000 Da) | 1% | 68 | No Improvement |
| Non covalent Hb interactions | Polyvinylpyrrolidone (10,000 Da) | 0.50% | 65 | No Improvement |
| Non covalent Hb interactions | Polyvinylpyrrolidone (10,000 Da) | 0.10% | 70 | No Improvement |
| Non covalent Hb interactions | Polyvinylpyrrolidone (10,000 Da) | 0.05% | 67 | No Improvement |
| Non covalent Hb interactions | Polyvinylpyrrolidone (10,000 Da) + CaCl2 | 0.1% + 10 mM | 77 | No Improvement |
| Non covalent Hb interactions | Polyvinylpyrrolidone (40,000 Da) | 1% | 68 | No Improvement |
| Non covalent Hb interactions | Polyvinylpyrrolidone (40,000 Da) | 0.50% | 67 | No Improvement |
| Non covalent Hb interactions | Polyvinylpyrrolidone (40,000 Da) | 0.10% | 65 | No Improvement |
| Non covalent Hb interactions | Polyvinylpyrrolidone (40,000 Da) | 0.05% | 68 | No Improvement |
| Non covalent Hb interactions | Polyvinylpyrrolidone (40,000 Da) + CaCl2 | 0.1% + 10 mM | 75 | No Improvement |
| Non covalent Hb interactions | Propylene Glycol | 1% | 67 | No Improvement |
| Non covalent Hb interactions | Propylene Glycol | 0.50% | 65 | No Improvement |
| Non covalent Hb interactions | Propylene Glycol | 0.10% | 69 | No Improvement |
| Protoporphyrin | Bilirubin | 0.00003% | 70 | No Improvement |
| Protoporphyrin | Bilirubin | 0.00030% | 68 | No Improvement |
| Protoporphyrin | Bilirubin | 0.00300% | 68 | No Improvement |
| Protoporphyrin | Bilirubin | 0.03000% | 66 | No Improvement |
| Protoporphyrin | Biliverdin | 0.00003% | 68 | No Improvement |
| Protoporphyrin | Biliverdin | 0.00030% | 66 | No Improvement |
| Protoporphyrin | Biliverdin | 0.00300% | 67 | No Improvement |
| Protoporphyrin | Biliverdin | 0.03000% | 60 | No Improvement |
| Non covalent Hb interactions | Polyvinylpyrrolidone (350,000 Da) | 0.10% | 71 | No Improvement |
| Non covalent Hb interactions | Polyvinylpyrrolidone (350,000 Da) | 0.50% | 69 | No Improvement |
| Non covalent Hb interactions | Polyvinylpyrrolidone (350,000 Da) | 1% | 77 | No Improvement |
| Non covalent Hb interactions | Polyvinylpyrrolidone (350,000 Da) | 2% | 54 | No Improvement |
| Non covalent Hb interactions | Polyvinylpyrrolidone (350,000 Da) + CaCl2 | 0.5% + 10 mM | 76 | No Improvement |

APPENDIX C

| Compound Classification | Additive | Additive Concentration | % Hb Recovery | Results |
| --- | --- | --- | --- | --- |
|  | Hb Collection Buffer - No additive | NA | 70 | Current Buffer Formulation |
|  | Polymedco Buffer - No Additive | NA | 80 |  |
| Preservatives with thiol groups | Sodium Thiosulfate | 0.02% | 52 | No Improvement |
| Preservatives with thiol groups | Sodium Thiosulfate | 0.01% | 59 | No Improvement |
| Preservatives with thiol groups | Sodium Thiosulfate | 0.005% | 62 | No Improvement |
| Preservatives with thiol groups | Sodium Thiosulfate | 0.0025% | 65 | No Improvement |
| Redox/antioxidants | (±)-α-Lipoic acid | 0.0126% | 64 | No Improvement |
| Redox/antioxidants | (±)-α-Lipoic acid | 0.0063% | 69 | No Improvement |
| Redox/antioxidants | (±)-α-Lipoic acid | 0.0032% | 69 | No Improvement |
| Redox/antioxidants | (±)-α-Lipoic acid | 0.0016% | 70 | No Improvement |
| Metal Chelators | Ethylenediamine-N,N'-disuccinic acid (EDDS) | 1 mM | 68 | No Improvement |
| Metal Chelators | Ethylenediamine-N,N'-disuccinic acid (EDDS) | 10 mM | 58 | No Improvement |
| Crosslinkers | Poly (acrylic acid) | 0.1 mM | 66 | No Improvement |
| Crosslinkers | Poly (acrylic acid) | 1 mM | 56 | No Improvement |
| Similar to Drabkin's Reagent (cyanide) | Imidazole | 0.25 mM | 68 | No Improvement |
| Similar to Drabkin's Reagent (cyanide) | Imidazole | 0.5 mM | 63 | No Improvement |
| Similar to Drabkin's Reagent (cyanide) | Hydroxylamine | 0.25 mM | 66 | No Improvement |
| Similar to Drabkin's Reagent (cyanide) | Hydroxylamine | 0.5 mM | 66 | No Improvement |
| Non-covalent Hb interactions | Dextran Sulphate | 0.25 mM | 69 | No Improvement |
| Non-covalent Hb interactions | Dextran Sulphate | 0.5 mM | 65 | No Improvement |
| Redox/antioxidants | mPEG2K-Lipoic Acid | 0.1 mM | 67 | No Improvement |
| Redox/antioxidants | mPEG2K-Lipoic Acid | 0.5 mM | 64 | No Improvement |

APPENDIX C-continued

| Compound Classification | Additive | Additive Concentration | | % Hb Recovery | Results |
|---|---|---|---|---|---|
| Redox/antioxidants | Urea | 50 | mM | 60 | No Improvement |
| Redox/antioxidants | Urea | 100 | mM | 63 | No Improvement |
| Formaldehyde Releaser | Imidazolidinyl Urea | 1 | mM | 65 | No Improvement |
| Formaldehyde Releaser | Imidazolidinyl Urea | 10 | mM | 62 | No Improvement |
| Metal Chelators | N,N-is-(Carboxymethyl)-L-glutamic acid tetrasodiumn salt (GLDA) | 1 | mM | 65 | No Improvement |
| Metal Chelators | N,N-is-(Carboxymethyl)-L-glutamic acid tetrasodiumn salt (GLDA) | 10 | mM | 40 | No Improvement |
| Preservatives with thiol groups | Cysteine | 1 | mM | 46 | No Improvement |
| Preservatives with thiol groups | Cysteine | 10 | mM | 36 | No Improvement |
| Preservatives with thiol groups | Glutathione | 1 | mM | 62 | No Improvement |
| Preservatives with thiol groups | Glutathione | 3 | mM | 62 | No Improvement |
| Preservatives with thiol groups | Dithiothreitol | 0.1 | mM | 63 | No Improvement |
| Preservatives with thiol groups | Dithiothreitol | 1 | mM | 59 | No Improvement |
| Preservatives with thiol groups | TCEP | 0.1 | mM | 64 | No Improvement |
| Preservatives with thiol groups | TCEP | 1 | mM | 70 | No Improvement |
| Sugars/Saccharides | Raffinose | 5 | mM | 69 | No Improvement |
| Sugars/Saccharides | Raffinose | 24 | mM | 65 | No improvement |
| Redox/antioxidants | Ascorbic Acid | 10 | mM | 38 | No Improvement |
| Redox/antioxidants | Ascorbic Acid | 25 | mM | 22 | No Improvement |
| Metal Chelators | Deferoxamine Mesylate Salt | 1 | mM | 67 | No Improvement |
| Metal Chelators | Deferoxamine Mesylate Salt | 5 | mM | 58 | No Improvement |
| Formaldehyde Releaser | Diazolidinyl Urea | 1 | mM | 65 | No Improvement |
| Formaldehyde Releaser | Diazolidinyl Urea | 10 | mM | 62 | No Improvement |
| Substrates | Diphosphoglycerate (DPG) | 1 | mM | 68 | No Improvement |
| Crosslinkers | Poly (acrylic acid) | 0.01 | mM | 65 | No Improvement |
| Crosslinkers | Poly (acrylic acid) | 0.001 | mM | 68 | No Improvement |
| Preservatives with thiol groups | Cysteine | 0.01 | mM | 68 | No Improvement |
| Preservatives with thiol groups | Cysteine | 0.1 | mM | 61 | No Improvement |
| Non-covalent Hb interactions | Dextran Sulphate | 0.0025 | mM | 69 | No Improvement |
| Non-covalent Hb interactions | Dextran Sulphate | 0.025 | mM | 66 | No Improvement |
| Substrates | Diphosphoglycerate (DPG) | 0.0005 | mM | 70 | No Improvement |
| Substrates | Diphosphoglycerate (DPG) | 0.002 | mM | 66 | No Improvement |
| Metal Chelators | N,N-is-(Carboxymethyl)-L-glutamic acid tetrasodiumn salt (GLDA) | 0.01 | mM | 70 | No Improvement |
| Metal Chelators | N,N-is-(Carboxymethyl)-L-glutamic acid tetrasodiumn salt (GLDA) | 0.1 | mM | 67 | No Improvement |
| Preservatives with thiol groups | TCEP | 0.005 | mM | 59 | No Improvement |
| Preservatives with thiol groups | TCEP | 0.01 | mM | 28 | No Improvement |
| Metal Chelators | EDTA: Disodium Salt | 5 | mM | 66 | No Improvement |
| Metal Chelators | EDTA: Disodium Salt | 10 | mM | 63 | No Improvement |
| Metal Chelators | EDTA: Disodium Salt | 30 | mM | 59 | No Improvement |
| Non-covalent Hb interactions | Heparin | 2.5 | uM | 68 | No Improvement |
| Non-covalent Hb interactions | Heparin | 25 | uM | 65 | No Improvement |
| Non-covalent Hb interactions | Heparin | 250 | uM | 66 | No Improvement |
| Sulfonic Acids | Methanedisulfonic acid dipotassium salt | 0.114 | mM | 66 | No Improvement |
| Sulfonic Acids | Methanedisulfonic acid dipotassium salt | 1.14 | mM | 67 | No Improvement |
| Sulfonic Acids | Methanedisulfonic acid dipotassium salt | 10.69 | mM | 66 | No Improvement |
| Non-covalent Hb interactions | PEG20000 | 0.024 | mM | 66 | No Improvement |
| Non-covalent Hb interactions | PEG20000 | 0.24 | mM | 68 | No Improvement |

APPENDIX C-continued

| Compound Classification | Additive | Additive Concentration | | % Hb Recovery | Results |
|---|---|---|---|---|---|
| Non-covalent Hb interactions | PEG20000 | 24 | mM | 62 | No Improvement |
| Sulfonic Acids | Propanedisulfonic acid disodium salt | 0.4 | mM | 64 | No Improvement |
| Sulfonic Acids | Propanedisulfonic acid disodium salt | 4 | mM | 66 | No Improvement |
| Sulfonic Acids | Propanedisulfonic acid disodium salt | 40 | mM | 66 | No Improvement |
| Flavoniods | Quercetin | 0.6 | uM | 64 | No Improvement |
| Flavoniods | Quercetin | 6 | uM | 67 | No Improvement |
| Flavoniods | Quercetin | 60 | uM | 59 | No Improvement |
| Redox/antioxidants | Uric Acid | 0.6 | uM | 67 | No Improvement |
| Redox/antioxidants | Uric Acid | 6 | uM | 65 | No Improvement |
| Redox/antioxidants | Uric Acid | 60 | uM | 65 | No Improvement |
| Redox/antioxidants | Ascorbic Acid | 10 | uM | 68 | No Improvement |
| Redox/antioxidants | Ascorbic Acid | 100 | uM | 65 | No Improvement |
| Osmolytes | Betaine | 50 | uM | 56 | No Improvement |
| Osmolytes | Betaine | 500 | uM | 63 | No Improvement |
| Metal Chelators | Deferoxamine Mesylate Salt | 10 | uM | 63 | No Improvement |
| Metal Chelators | Deferoxamine Mesylate Salt | 100 | uM | 59 | No Improvement |
| Formaldehyde Releaser | Diazolidinyl Urea | 10 | uM | 68 | No Improvement |
| Formaldehyde Releaser | Diazolidinyl Urea | 100 | uM | 62 | No Improvement |
| Preservatives with thiol groups | Dithiothreitol | 1 | uM | 65 | No Improvement |
| Preservatives with thiol groups | Dithiothreitol | 10 | uM | 61 | No Improvement |
| Metal Chelators | Ethylenediamine-N,N'-disuccinic acid (EDDS) | 10 | uM | 66 | No Improvement |
| Metal Chelators | Ethylenediamine-N,N'-disuccinic acid (EDDS) | 100 | uM | 64 | No Improvement |
| Preservatives with thiol groups | Glutathione | 10 | uM | 65 | No Improvement |
| Preservatives with thiol groups | Glutathione | 100 | uM | 56 | No Improvement |
| Similar to Drabkin's Reagent (cyanide) | Hydroxylamine | 2.5 | uM | 63 | No Improvement |
| Similar to Drabkin's Reagent (cyanide) | Hydroxylamine | 25 | uM | 63 | No Improvement |
| Similar to Drabkin's Reagent (cyanide) | Imidazole | 2.5 | uM | 70 | No Improvement |
| Similar to Drabkin's Reagent (cyanide) | Imidazole | 25 | uM | 66 | No Improvement |
| Formaldehyde Releaser | Imidazolidinyl Urea | 10 | uM | 68 | No Improvement |
| Formaldehyde Releaser | Imidazolidinyl Urea | 100 | uM | 65 | No Improvement |
| Redox/antioxidants | mPEG2K-Lipoic Acid | 10 | uM | 66 | No Improvement |
| Redox/antioxidants | mPEG2K-Lipoic Acid | 100 | uM | 65 | No Improvement |
| Sugars/Saccharides | Raffinose | 5 | uM | 66 | No Improvement |
| Sugars/Saccharides | Raffinose | 50 | uM | 64 | No Improvement |
| Osmolytes | Trimethylamine N-oxide (TMANO) | 500 | uM | 64 | No Improvement |
| Osmolytes | Trimethylamine N-oxide (TMANO) | 5 | mM | 63 | No Improvement |
| Redox/antioxidants | Urea | 500 | uM | 66 | No Improvement |
| Redox/antioxidants | Urea | 5 | mM | 62 | No Improvement |
| Metal Chelators | N,N-is-(Carboxymethyl)-L-glutamic acid tetrasodiumn salt (GLDA) | 10 | mM | 42 | No Improvement |
| Metal Chelators | Iminodisuccinic acid | 10 | mM | 59 | No Improvement |
| Preservatives with thiol groups | Cysteine | 0.1 | uM | 65 | No Improvement |
| Preservatives with thiol groups | Cysteine | 1 | uM | 67 | No Improvement |
| Preservatives with thiol groups | Cysteine | 5 | uM | 65 | No Improvement |
| Non-covalent Hb interactions | Dextran Sulphate | 0.2 | uM | 69 | No Improvement |
| Non-covalent Hb interactions | Dextran Sulphate | 1 | uM | 65 | No Improvement |
| Non-covalent Hb interactions | Dextran Sulphate | 2 | uM | 67 | No Improvement |
| Substrates | Diphosphoglycerate (DPG) | 0.5 | uM | 67 | No Improvement |
| Substrates | Diphosphoglycerate (DPG) | 5 | uM | 68 | No Improvement |
| Substrates | Diphosphoglycerate (DPG) | 50 | uM | 66 | No Improvement |
| Metal Chelators | N,N-is-(Carboxymethyl)-L-glutamic acid tetrasodiumn salt (GLDA) | 0.1 | uM | 67 | No Improvement |

APPENDIX C-continued

| Compound Classification | Additive | Additive Concentration | % Hb Recovery | Results |
| --- | --- | --- | --- | --- |
| Metal Chelators | N,N-is-(Carboxymethyl)-L-glutamic acid tetrasodiumn salt (GLDA) | 1 uM | 65 | No Improvement |
| Metal Chelators | N,N-is-(Carboxymethyl)-L-glutamic acid tetrasodiumn salt (GLDA) | 5 uM | 68 | No Improvement |
| Non-covalent Hb interactions | PEG2000 | 0.033 uM | 68 | No Improvement |
| Non-covalent Hb interactions | PEG2000 | 0.33 uM | 66 | No Improvement |
| Non-covalent Hb interactions | PEG2000 | 3.3 uM | 66 | No Improvement |
| Redox/antioxidants | mPEG2K-Lipoic Acid | 0.1 uM | 67 | No Improvement |
| Redox/antioxidants | mPEG2K-Lipoic Acid | 1 uM | 65 | No Improvement |
| Redox/antioxidants | mPEG2K-Lipoic Acid | 5 uM | 66 | No Improvement |
| Preservatives with thiol groups | TCEP | 250 uM | 62 | No Improvement |
| Preservatives with thiol groups | TCEP | 500 uM | 66 | No Improvement |
| Preservatives with thiol groups | TCEP | 750 uM | 68 | No Improvement |
| Redox/antioxidants | Ascorbic Acid | 0.2 uM | 69 | No Improvement |
| Redox/antioxidants | Ascorbic Acid | 1 uM | 68 | No Improvement |
| Redox/antioxidants | Ascorbic Acid | 5 uM | 64 | No Improvement |
| Formaldehyde Releaser | Diazolidinyl Urea + Imidazolidinyl Urea | 10 uM and 10 uM | 65 | No Improvement |
| Formaldehyde Releaser | Diazolidinyl Urea + Imidazolidinyl Urea | 100 uM and 100 uM | 56 | No Improvement |
| Formaldehyde Releaser | Diazolidinyl Urea + Imidazolidinyl Urea | 1 mM and 1 mM | 61 | No Improvement |
| Sugars/Saccharides | Glucose | 72 uM | 67 | No Improvement |
| Sugars/Saccharides | Glucose | 720 uM | 69 | No Improvement |
| Sugars/Saccharides | Glucose | 7.2 mM | 67 | No Improvement |
| Crosslinkers | Magnesium Gluconate | 1.2 uM | 68 | No Improvement |
| Crosslinkers | Magnesium Gluconate | 12 uM | 63 | No Improvement |
| Crosslinkers | Magnesium Gluconate | 120 uM | 71 | No Improvement |
| Enzyme inhibitors | Sodium Fluoride | 8.5 uM | 68 | No Improvement |
| Enzyme Inhibitors | Sodium Fluoride | 85 uM | 67 | No Improvement |
| Enzyme Inhibitors | Sodium Fluoride | 850 uM | 70 | No Improvement |
| Enzyme Inhibitors | Sodium Fluoride and Glucose | 950 uM and 7.2 mM | 65 | No Improvement |
| Enzyme Inhibitors | Sodium Fluoride and Glucose | 950 uM and 72 uM | 67 | No Improvement |
| Enzyme Inhibitors | Sodium Fluoride and Glucose | 950 uM and 720 uM | 65 | No Improvement |
| Redox/antioxidants | Urea | 2.5 uM | 70 | No Improvement |
| Redox/antioxidants | Urea | 25 uM | 69 | No Improvement |
| Redox/antioxidants | Urea | 250 uM | 70 | No Improvement |
| Formaldehyde + Ammonium Salt Complexes | Ammonium Acetate + Formaldehyde | 10 mM + 0.02% | 66 | No Improvement |
| Formaldehyde + Ammonium Salt Complexes | Ammonium Acetate + Formaldehyde | 100 mM + 0.1% | 58 | No Improvement |
| Formaldehyde + Ammonium Salt Complexes | Ammonium Acetate + Formaldehyde | 767 mM + 1% | 37 | No Improvement |
| Formaldehyde + Ammonium Salt Complexes | Ammonium Chloride + Formaldehyde | 10 mM + 0.02% | 63 | No Improvement |
| Formaldehyde + Ammonium Salt Complexes | Ammonium Chloride + Formaldehyde | 50 mM + 0.1% | 56 | No Improvement |
| Formaldehyde + Ammonium Salt Complexes | Ammonium Chloride + Formaldehyde | 95 mM + 1% | 17 | No Improvement |
| Formaldehyde + Ammonium Salt Complexes | Ammonium Oxalate + Formaldehyde | 0.1 mM + 0.2% | 65 | No Improvement |
| Formaldehyde + Ammonium Salt Complexes | Ammonium Oxalate + Formaldehyde | 1 mM + 0.1% | 55 | No Improvement |
| Formaldehyde + Ammonium Salt Complexes | Ammonium Oxalate + Formaldehyde | 4.8 mM + 1% | 19 | No Improvement |
| Formaldehyde + Ammonium Salt Complexes | Ammonium Sulfate + Formaldehyde | 1 mM + 0.02% | 65 | No Improvement |
| Formaldehyde + Ammonium Salt Complexes | Ammonium Sulfate + Formaldehyde | 10 mM + 0.1% | 58 | No Improvement |
| Formaldehyde + Ammonium Salt Complexes | Ammonium Sulfate + Formaldehyde | 243 mM + 1% | 11 | No Improvement |

APPENDIX C-continued

| Compound Classification | Additive | Additive Concentration | % Hb Recovery | Results |
|---|---|---|---|---|
| Metal Chelators | ATMP | 0.02 mM | 65 | No Improvement |
| Metal Chelators | ATMP | 0.2 mM | 67 | No Improvement |
| Metal Chelators | ATMP | 2 mM | 42 | No Improvement |
| Crosslinkers | Cysteamine | 0.016 mM | 66 | No Improvement |
| Crosslinkers | Cysteamine | 0.16 mM | 62 | No Improvement |
| Crosslinkers | Cysteamine | 1.6 mM | 45 | No Improvement |
| Formaldehyde + Ammonium Salt Complexes | Hexamethylenetetramine | 14 mM | 63 | No Improvement |
| Formaldehyde + Ammonium Salt Complexes | Hexamethylenetetramine | 140 mM | 55 | No Improvement |
| Formaldehyde + Ammonium Salt Complexes | Hexamethylenetetramine | 500 mM | 52 | No Improvement |
| Osmolytes | Betaine | 50 mM | 55 | No Improvement |
| Osmolytes | Betaine | 96 mM | 49 | No Improvement |
| Osmolytes | Trimethylamine N-oxide (TMANO) | 50 mM | 65 | No Improvement |
| Osmolytes | Trimethylamine N-oxide (TMANO) | 87 mM | 65 | No Improvement |
| Metal Chelators | Trisodium N-(1-Carboxylatoethyl)iminodiacetate Hydrate (MGDA) | 0.1 mM | 69 | No Improvement |
| Metal Chelators | Trisodium N-(1-Carboxylatoethyl)iminodiacetate Hydrate (MGDA) | 1 mM | 65 | No Improvement |
| Metal Chelators | Trisodium N-(1-Carboxylatoethyl)iminodiacetate Hydrate (MGDA) | 10 mM | 49 | No Improvement |
| Flavoniods | 7,8 dihydroxyflavone hydrate | 0.01 mM | 60 | No Improvement |
| Flavoniods | 7,8 dihydroxyflavone hydrate | 0.1 mM | 59 | no improvement |
| Flavoniods | 7,8 dihydroxyflavone hydrate | 1 mM | 36 | No Improvement |
| Crosslinkers | Bis(3,5-dibromosalilcyl)fumarate | 5 uM | 65 | No Improvement |
| Crosslinkers | Bis(3,5-dibromosalilcyl)fumarate | 10 uM | 59 | No Improvement |
| Crosslinkers | Bis(3,5-dibromosalilcyl)fumarate | 100 uM | 43 | No Improvement |
| Flavoniods | Daidzein | 0.01 mM | 66 | No Improvement |
| Flavoniods | Daidzein | 0.1 mM | 62 | No Improvement |
| Flavoniods | Daidzein | 1 mM | 42 | No Improvement |
| Substrates | Arginine | 0.058 mM | 66 | No Improvement |
| Substrates | Arginine | 0.58 mM | 68 | No Improvement |
| Substrates | Arginine | 5.8 mM | 59 | No Improvement |
| Flavoniods | Chrysin | 0.0254 mM | 67 | No Improvement |
| Flavoniods | Chrysin | 0.254 mM | 56 | No Improvement |
| Flavoniods | Chrysin | 2.54 mM | 44 | No Improvement |
| Crosslinkers | Dimethyl 3,3'-dithioproprionimidate dihydrochloride | 0.0032 mM | 67 | No Improvement |
| Crosslinkers | Dimethyl 3,3'-dithioproprionimidate dihydrochloride | 0.032 mM | 63 | No Improvement |
| Crosslinkers | Dimethyl 3,3'-dithioproprionimidate dihydrochloride | 0.32 mM | 52 | No Improvement |
| Substrates | Lysine | 0.0687 mM | 67 | No Improvement |
| Substrates | Lysine | 0.687 mM | 67 | No Improvement |
| Substrates | Lysine | 6.87 mM | 59 | No Improvement |
| Substrates | Sodium Bicarbonate | 0.0895 mM | 71 | No Improvement |
| Substrates | Sodium Bicarbonate | 0.895 mM | 66 | No Improvement |
| Substrates | Sodium Bicarbonate | 8.95 mM | 61 | No Improvement |
| Sugars/Saccharides | Trehalose | 0.0174 mM | 65 | No Improvement |
| Sugars/Saccharides | Trehalose | 0.174 mM | 68 | No Improvement |
| Sugars/Saccharides | Trehalose | 1.74 mM | 66 | No Improvement |
| Ionic Liquid | 1-Allyl-3-methylimidazolium Chloride | 0.01 mM | 69 | No Improvement |
| Ionic Liquid | 1-Allyl-3-methylimidazolium Chloride | 0.1 mM | 64 | No Improvement |
| Ionic Liquid | 1-Allyl-3-methylimidazolium Chloride | 1 mM | 70 | No Improvement |
| Ionic Liquid | 1-Allyl-3-methylimidazolium Chloride + NaBr | 0.01 mM + 0.01 mM | 68 | No Improvement |

APPENDIX C-continued

| Compound Classification | Additive | Additive Concentration | % Hb Recovery | Results |
|---|---|---|---|---|
| Ionic Liquid | 1-Allyl-3-methylimidazolium Chloride + NaBr | 0.1 mM + 0.1 mM | 66 | No Improvement |
| Ionic Liquid | 1-Allyl-3-methylimidazolium Chloride + NaBr | 1 mM + 1 mM | 68 | No Improvement |
| Ionic Liquid | 1-Butyl-3-methylimidazoium Chloride | 0.01 mM | 66 | No Improvement |
| Ionic Liquid | 1-Butyl-3-methylimidazoium Chloride | 0.1 mM | 67 | No Improvement |
| Ionic Liquid | 1-Butyl-3-methylimidazoium Chloride | 1 mM | 65 | No Improvement |
| Ionic Liquid | 1-Butyl-3-methylimidazoium Chloride + NaBr | 0.01 mM + 0.01 mM | 66 | No Improvement |
| Ionic Liquid | 1-Butyl-3-methylimidazoium Chloride + NaBr | 0.1 mM + 0.1 mM | 63 | No Improvement |
| Ionic Liquid | 1-Butyl-3-methylimidazoium Chloride + NaBr | 1 mM + 1 mM | 67 | No Improvement |
| Osmolytes | Ectoine | 0.072 mM | 61 | No Improvement |
| Osmolytes | Ectoine | 0.718 mM | 64 | No Improvement |
| Osmolytes | Ectoine | 5 mM | 45 | No Improvement |
| Osmolytes | Firoin | 0.038 mM | 68 | No Improvement |
| Osmolytes | Firoin | 0.377 mM | 68 | No Improvement |
| Osmolytes | Firoin | 1 mM | 69 | No Improvement |
| Substrates | Arginine | 0.0058 mM | 69 | No Improvement |
| Substrates | Arginine | 0.058 mM | 68 | No Improvement |
| Substrates | Arginine | 0.25 mM | 66 | No Improvement |
| Flavoniods | Chrysin | 0.0000254 mM | 68 | No Improvement |
| Flavoniods | Chrysin | 0.0000254 mM | 70 | No Improvement |
| Flavoniods | Chrysin | 0.00254 mM | 68 | No Improvement |
| Crosslinkers | Dimethyl 3,3'-dithioproprionimidate dihydrochloride | 0.0000032 mM | 69 | No Improvement |
| Crosslinkers | Dimethyl 3,3'-dithioproprionimidate dihydrochloride | 0.000032 mM | 68 | No Improvement |
| Crosslinkers | Dimethyl 3,3'-dithioproprionimidate dihydrochloride | 0.00032 mM | 68 | No Improvement |
| Similar to Drabkin's Reagent (cyanide) | Histidine | 0.0028 mM | 66 | No Improvement |
| Similar to Drabkin's Reagent (cyanide) | Histidine | 0.0228 mM | 71 | No Improvement |
| Similar to Drabkin's Reagent (cyanide) | Histidine | 0.228 mM | 68 | No Improvement |
| Substrates | Sodium Bicarbonate | 0.0000895 mM | 67 | No Improvement |
| Substrates | Sodium Bicarbonate | 0.000895 mM | 67 | No Improvement |
| Substrates | Sodium Bicarbonate | 0.00895 mM | 67 | No Improvement |
| Sugars/Saccharides | Trehalose | 1.74 mM | 70 | No Improvement |
| Sugars/Saccharides | Trehalose | 10 mM | 70 | No Improvement |
| Sugars/Saccharides | Trehalose | 16.76 mM | 71 | No Improvement |
| HRP Stabilizer Components | HRP Conjugate Stabilizer (PN SZ02) | 5% | 79 | Improvement |
| Polyvalent Ions/Metal Salts | Calcium Chloride | 10 mM | 76 | Improvement |
| Polyvalent Ions/Metal Salts | Magnesium Sulfate | 10 mM | 74 | Improvement |
| HRP Stabilization Components | HRP Conjugate Stabilizer (PN 85R-102) | 15% | 70 | Improvement |
| Osmolytes | Betaine | 3.5M | 78 | Improvement |
| HRP Stabilizer Components | HRP Conjugate Stabilizer (PN SZ02) | 15% | 79 | Improvement |
| Sugars/Saccharides | Sucrose | 0.24M | 75 | Improvement |
| Sugars/Saccharides | Trehalose | 0.3M | 77 | Improvement |
| Protoporphyrin | Hemin, pH 6.5 | 0.0003% | 90 | Improvement |
| Protoporphyrin | Protoporphyrin IX Zinc, pH 6.5 | 1 uM | 89 | Improvement |
| Protoporphyrin | Protoporphyrin IX Zinc, pH 7.4 | 1 uM | 75 | Improvement |
| Protoporphyrin | Protoporphyrin IX Chromium, pH 6.5 | 2.5 uM | 117 | Improvement |
| Protoporphyrin | Protoporphyrin IX Chromium, pH 7.4 | 2.5 uM | 102 | Improvement |
| Protoporphyrin | Protoporphyrin IX Cobalt, pH 6.5 | 5 uM | 109 | Improvement |
| Protoporphyrin | Protoporphyrin IX Cobalt, pH 7.4 | 5 uM | 111 | Improvement |

APPENDIX D

| Compound Classification | Compound Combinations |
|---|---|
| Crosslinkers | 4arm-PEG2K-Maleimide + Iminothiolane hydrochloride |
| | mPEG-Mal, 5K + Iminothiolane hydrochloride |
| Sugars/Saccharides | Trehlose + Glycine |
| | Trehalose + Glycerol |
| | Glucose + Glycine |
| | Glucose + Glycerol |
| | Trehalose + Glucose |
| | DEAE-Dextrose + Ethylene Glycol + Calcium Chloride |
| | Sucrose + Glucose |
| | Sucrose + Trehalose |
| | Sucrose + Raffinose |
| | Raffinose + Trehalose |
| | Raffinose + Glucose |
| | Raffinose + Betaine |
| | Raffinose + CaCl2 |
| | Raffinose + Ectoine |
| | Raffinose + MgSO4 |
| | Raffinose + TMANO |
| | Sucrose + Betaine |
| | Sucrose + CaCl2 |
| | Sucrose + Ectoine |
| | Sucrose + MgSO4 |
| | Sucrose + TMANO |
| | Trehalose + Betaine |
| | Trehalose + CaCl2 |
| | Trehalose + Ectoine |
| | Trehalose + MgSO4 |
| | Trehalose + TMANO |
| | Glucose + Betaine |
| | Glucose + CaCl2 |
| | Glucose + Ectoine |
| | Glucose + MgSO4 |
| | Glucose + TMANO |
| | Sodium Fluoride + Glucose |
| | Polygalacturonic Acid + CaCl2 |
| | Galacturonic Acid + CaCl2 |
| | Sodium Alginate (synthetic) + CaCl2 |
| | Sodium Alginate (Medium Viscosity) + CaCl2 |
| | Sodium Alginate (Low Viscosity) + CaCl2 |
| Formaldehyde Releasers | Diazolidinyl Urea + Glycine + Formaldehyde |
| | Diazolidinyl Urea + Glycine |
| | Diazolidinyl Urea + Zinc |
| | Imidazolidinyl Urea + Glycine + Formaldehyde |
| | Imidazolidinyl Urea + Glycine |
| | Imidazolidinyl Urea + Diazolidinyl Urea |
| Protoporphyrins | Protoporphyrin IX + Iron Chloride |
| | Hemin + BSA |
| | Protoporphyrin IX Tin + BSA |
| | Protoporphyrin IX Zinc + BSA |
| | Protoporphyrin IX + BSA |
| | Protoporphyrin IX + Zinc Chloride |
| | Hemin + CaCl2 |
| | Hemin + MgSO4 |
| | Hemin + FeCl2 |
| | Hemin + FeCl3 |
| | BSA + Hemin |
| | BSA + Hemin + CaCl2 |
| | BSA + Hemin + MgSO4 |
| | BSA + Hemin + FeCl2 |
| | BSA + Hemin + FeCl3 |
| | Hemin + Sodium Azide |
| | Hemin + BSA + Sodium Azide |
| Formaldehyde + Ammonium Salt Complexes | Ammonium Chloride + Formaldehyde |
| | Ammonium Oxalate + Formaldehyde |
| | Ammonium Sulfate + Formaldehyde |
| | Ammonium Acetate + Formaldehyde |
| Ionic Liquids | 1-Allyl-3-methylimidazolium chloride + Sodium Bromide |
| | 1-Butyl-3-methylimidazolium chloride + Sodium Bromide |
| Polyvalent Ions/ Metal Salts | Copper Chloride + Sucrose |
| | Iron Chloride + Sucrose |
| | Nickel Chloride + Sucrose |
| | Zinc Chloride + Sucrose |
| | Cobalt Chloride + Sucrose |
| | Magnesium Sulfate + Sucrose |
| | Calcium Propoinate + PEG 8000 |
| | Calcium Propoinate + PEG 8000 + Calcium Chloride |
| | Calcium + Cobalt |
| | Calcium + Copper |
| | Calcium + Iron |
| | Calcium + Magnesium |
| | Calcium + Nickel |
| | Calcium + Zinc |
| | Cobalt + Copper |
| | Cobalt + Iron |
| | Cobalt + Magnesium |
| | Cobalt + Nickel |
| | Cobalt + Zinc |
| | Copper + Magnesium |
| | Copper + Nickel |
| | Copper + Zinc |
| | Iron + Magnesium |
| | Iron + Nickel |
| | Iron + Zinc |
| | Magnesium + Nickel |
| | Magnesium + Zinc |
| | Calcium Chloride + PEG 8000 |
| | Calcium Chloride + PEG 20000 |
| | Calcium Chloride + PEG 2000 |
| | Nickel + Zinc |
| | Iron Chloride + EDTA |
| | Iron Chloride + IDA |
| | Iron Chloride + GLDA |
| HRP Stabilizer Components | Surmodics HRP Stabilization Buffer + Magnesium Sulfate |
| | Surmodics HRP Stabilization Buffer + Calcium Chloride |
| | Fitzgerald HRP Conjugate Buffer + Magnesium Sulfate |
| | Fitzgerald HRP Conjugate Buffer + Calcium Chloride |
| | Fitzgerald HRP Conjugate Buffer + Cobalt Chloride |
| | Fitzgerald HRP Conjugate Buffer + Copper Chloride |
| | Fitzgerald HRP Conjugate Buffer + Nickel Chloride |
| | Fitzgerald HRP Conjugate Buffer + Zinc Chloride |
| | Fitzgerald HRP Conjugate Buffer + Iron (III) Chloride |
| | Fitzgerald HRP Conjugate Buffer + Aluminum Chloride |
| | Fitzgerald HRP Conjugate Buffer + Lithium Chloride |
| | Fitzgerald HRP Conjugate Buffer + Sodium Chloride |

We claim:

1. A method of stabilizing hemoglobin (Hb) in a stool sample, comprising:
   combining the stool sample with a stool resuspension solution comprising a protoporphyrin complexed with $Cr^{3+}$ or $Co^{3+}$ to produce a suspension,
   wherein the protoporphyrin complexed with $Cr^{3+}$ or $Co^{3+}$ stabilizes Hb in the stool sample.

2. The method of claim 1, further comprising maintaining the suspension for a period of 3, 4, 5, 6, or 7 days at ambient temperature.

3. The method of claim 1, further comprising shipping the suspension to a remote location.

4. The method of claim 2, further comprising shipping the suspension to a remote location.

5. The method of claim 1, wherein the stool resuspension solution comprises protoporphyrin complexed with $Cr^{3+}$.

6. The method of claim 1, wherein the stool resuspension solution comprises protoporphyrin complexed with $Co^{3+}$.

7. The method of claim 1, wherein the protoporphyrin is protoporphyrin IX.

8. The method of claim 5, wherein the protoporphyrin is protoporphyrin IX.

9. The method of claim 6, wherein the protoporphyrin is protoporphyrin IX.

10. The method of claim 1, wherein the stool resuspension solution has a pH in the range of pH 6.5 to pH 7.4.

11. The method of claim 8, wherein the concentration of protoporphyrin IX complexed with $Cr^{3+}$ is 1.25-5 µM.

12. The method of claim 11, wherein the stool resuspension solution has a pH in the range of pH 6.9 to pH 7.4.

13. The method of claim 8, wherein the concentration of protoporphyrin IX complexed with $Cr^{3+}$ is 1.5-4.5 µM.

14. The method of claim 8, wherein the concentration of protoporphyrin IX complexed with $Cr^{3+}$ is 2.5 µM.

15. The method of claim 14, wherein the stool resuspension solution has a pH in the range of pH 6.9 to pH 7.4.

16. The method of claim 9, wherein the concentration of protoporphyrin IX complexed with $Co^{3+}$ is 2.5-10 µM.

17. The method of claim 16, wherein the stool resuspension solution has a pH in the range of pH 6.5 to pH 7.4.

18. The method of claim 9, wherein the concentration of protoporphyrin IX complexed with $Co^{3+}$ is 3-5 µM.

19. The method of claim 1, wherein the stool resuspension solution comprises a buffer, bovine serum albumin, polysorbate 20, sodium azide, sodium chloride, ethylenediaminetetraacetic acid, and gentamicin.

20. The method of claim 19, wherein the buffer is Tris buffer.

* * * * *